(12) United States Patent
Schnapp et al.

(10) Patent No.: US 8,178,091 B2
(45) Date of Patent: May 15, 2012

(54) COMPOSITIONS AND METHODS FOR THE TREATMENT OF RESPIRATORY DISORDERS

(75) Inventors: Lynn M. Schnapp, Seattle, WA (US); Jung-eun Choi, Seachu-Gu (KR)

(73) Assignee: University of Washington, Seattle, WA (US)

( * ) Notice: Subject to any disclaimer, the term of this patent is extended or adjusted under 35 U.S.C. 154(b) by 366 days.

(21) Appl. No.: 12/124,494

(22) Filed: May 21, 2008

(65) Prior Publication Data

US 2009/0016967 A1    Jan. 15, 2009

Related U.S. Application Data

(60) Provisional application No. 60/931,136, filed on May 21, 2007.

(51) Int. Cl.
*A61K 39/395* (2006.01)
*A61K 38/16* (2006.01)
*A61K 38/30* (2006.01)

(52) U.S. Cl. ............... 424/130.1; 424/143.1; 424/198.1; 514/8.6

(58) Field of Classification Search ........................ None
See application file for complete search history.

(56) References Cited

U.S. PATENT DOCUMENTS

| 7,557,190 | B2 * | 7/2009 | Barbosa et al. | ............ 530/387.1 |
| 7,566,721 | B2 * | 7/2009 | Ji et al. | ...................... 514/260.1 |
| 2005/0054638 | A1 | 3/2005 | Barlaam et al. | |
| 2007/0032512 | A1 | 2/2007 | Ji et al. | |

FOREIGN PATENT DOCUMENTS

| WO | 2005016970 A2 | 2/2005 |
| WO | 2006/008639 A1 | 1/2006 |
| WO | 2007/099171 A1 | 9/2007 |

OTHER PUBLICATIONS

Krein et al. (2003), American J. of Respiratory and Critical Care Medicine, vol. 167, pp. 83-90.*
Adams et al., Cell. Mol. Life Sci., 57:1050-1093 (2000). "Structure and Function of the Type 1 Insulin-like Growth Factor Receptor."
American Thoracic Society, Am J Respir Crit Care Med, 161:646-664 (2000). "Idiopathic Pulmonary Fibrosis: Diagnosis and Treatment."
Ashbaugh et al., The Lancet, 2:319-323 (1967). "Acute Respiratory Distress in Adults."
Baserga, R., Oncogene, 19:5574-5581 (2000). "The Contradictions of the Insulin-like Growth Factor 1 Receptor."
Bernard et al., Journal of Critical Care, 9(1):72-81 (1994). "Report of the American-European Consensus Conference on Acute Respiratory Distress Syndrome: Definitions, Mechanisms, Relevant Outcomes, and Clinical Trial Coordination."
Byrd et al., The Journal of Biological Chemistry, 274(34):24408-24416 (1999). "Disruption of Ligand Binding to the Insulin-like Growth Factor II/Mannose 6-Phosphate Receptor by Cancer-associated Missense Mutations."
Mapel et al., Chest, 110:1058-1067 (1996). "Corticosteroids and the Treatment of Idiopathic Pulmonary Fibrosis."
Oates et al., Breast Cancer Research and Treatment, 47:269-281 (1998). "The Mannose 6-Phosphate/Insulin-Like Growth Factor 2 Receptor (M6P/IGF2R), a Putative Breast Tumor Suppressor Gene."
Pandini et al., Clinical Cancer Research, 5:1935-1944 (1999). "Insulin and Insulin-like Growth Factor-I (IGF-I) Receptor Overexpression in Breast Cancers Leads to Insulin/IGF-I Hybrid Receptor Overexpression: Evidence for a Second Mechanism of IGF-I Signaling."
Pittet et al., Am J Respir Crit Care Med, 155:1187-1205 (1997). "Biological Markers of Acute Lung Injury: Prognostic and Pathogenetic Significance."
Raghu, G. et al., Am Rev Respir Dis, 144:291-296 (1991). "Azathioprine Combined with Prednisone in the Treatment of Idiopathic Pulmonary Fibrosis: A Prospective Double-blind, Randomized, Placebo-controlled Clinical Trial."
Siddle et al., Contemporary Endocrinology: The IGF System, pp. 199-225 (1999). "Alternative IGF-Related Receptors."
International Search Report for International Patent Application PCT/US2008/064338 (Nov. 13, 2008).
Sarma et al., "Progress in the Development of Small Molecule Inhibitors of Insulin-like Growth Factor-1 Receptor Kinase," Expert Opin. Ther. Patents 17(1):25-35 (2007).
Schnapp et al., "Mining the Acute Respiratory Distress Syndrome Proteome: Identification of the Insulin-Like Growth Factor (IGF)/IGF-Binding Protein-3 Pathway in Acute Lung Injury," American Journal of Pathology 169(1):86-95 (2006).
Zhang et al., "The Therapeutic Potential of Agents Targeting the Type I Insulin-like Growth Factor Receptor," Expert Opin. Investig. Drugs 13(12):1569-77 (2004).
Burtrum et al, Cancer Res. 63:8912-8921 (2003).
Dunn et al., Cancer Res. 58: 3353-3361 (1988).
Frankel et al., Am J Physiol Lung Cell Mol Physiol 288: 805-812 (2005).
Goetsch et al, Intl. J. Cancer 113:316-328 (2005).
Hill et al., Infect. Immun. 74:3068-3070 (2006).
James et al, J. Surg. Res. 163: 86-95 (2010).
Lee et al., Cancer Gene Therapy 10: 57-63 (2003).
Maloney et al., Cancer Res. 63: 5073-5083 (2003).
Muguerza et al., Biochim. Biophys. Acta 1536: 185-195 (2001).
Oldroyd et al., Am. J. Physiol. Renal Physiol 290: 695-702 (2006).
Pautsch et al., Structure: 955-965a (2001).
Raab, et al., Biochim Biophys Acta 1333:F179-F199 (1997).
Ullrich et al., EMBO J. 5: 2503-2512 (1986).
Wagener et al., J Pediatr. 133(4):486-491 (1998).
Xu et al., Am. J. Respir. Crit. Care Med. 178(1): 60-73 (2008).

* cited by examiner

*Primary Examiner* — Christine J Saoud
*Assistant Examiner* — Jegatheesan Seharaseyon
(74) *Attorney, Agent, or Firm* — Nixon Peabody LLP; Mark J. FitzGerald

(57) ABSTRACT

Methods and compositions are provided for the treatment of acute lung injury and pulmonary fibrosis by administering inhibitors of IGF-1R signaling activity.

8 Claims, 22 Drawing Sheets

COMPOSITIONS AND METHODS FOR THE TREATMENT OF RESPIRATORY DISORDERS

This application claims priority under 35 U.S.C. §119(e) to U.S. Provisional Application Ser. No. 60/931,136, filed May 21, 2007, the entirety of which is incorporated herein by reference.

GOVERNMENT SUPPORT

This invention was made with government support under 5 P50 HL073996 awarded by the National Institutes of Health. The government has certain rights in the invention.

FIELD OF THE INVENTION

The present invention relates to methods for the treatment of respiratory disorders using inhibitors of IGF-1R activity or expression.

BACKGROUND OF THE INVENTION

Pulmonary diseases or disorders frequently involve or trigger both inflammation and fibrosis. For example, Acute Respiratory Distress Syndrome (ARDS) is characterized by an acute pulmonary inflammatory process with epithelial apoptosis and interstitial and inter-alveolar edema, followed by fibroblast proliferation, migration and fibrosis. Similarly, acute lung injury, induced, for example, by inhalation of toxic substances, infection, or as a side effect of drug therapy (e.g., chemotherapy with bleomycin), can result in inflammation and fibrosis.

Pulmonary fibrosis of unknown etiology is known as Idiopathic Pulmonary Fibrosis (IPF). It is of insidious onset with nonproductive cough and dyspnea. The estimated five year survival is 30-50%, with a mean survival from the time of diagnosis of 2-4 years (*Am. J. Resp. Crit. Care. Med.* 161: 646-664 (2000)).

The pathology of IPF is multifactorial. Bronchoalveolar lavage shows an increase in PMNs, eosinophils, alveolar macrophages, and lymphocytes, as well as increased levels of cytokines, growth factors, and immune complexes. The common final pathway is fibrosis of lung parenchyma with increasing respiratory insufficiency and eventual respiratory failure.

Corticosteroids and cytotoxic agents have been a mainstay of therapy, with only 10-30% of patients showing an initial transient response, suggesting the need for long-term therapy (Mapel et al., *Chest* 110: 1058-1067 (1996); Raghu et al., *Am. Rev. Respir. Dis.* 144:291-296 (1991)).

The insulin-like growth factor receptor (IGF-1R) is a ubiquitous transmembrane tyrosine kinase receptor that is essential for normal fetal and post-natal growth and development. IGF-1R can stimulate cell proliferation, cell differentiation, changes in cell size, and protect cells from apoptosis. It has also been considered to be quasi-obligatory for cell transformation (reviewed in Adams et al., *Cell. Mol. Life. Sci.* 57:1050-93 (2000); Baserga, *Oncogene* 19:5574-81 (2000)). The IGF-1R is located on the cell surface of most cell types and serves as the signaling molecule for growth factors IGF-I and IGF-II (collectively termed henceforth IGFs). IGF-1R also binds insulin, albeit at three orders of magnitude lower affinity than it binds to IGFs. IGF-1R is a pre-formed heterotetramer containing two alpha and two beta chains covalently linked by disulfide bonds. The receptor subunits are synthesized as part of a single polypeptide chain of 180 kd, which is then proteolytically processed into alpha (130 kd) and beta (95 kd) subunits. The entire alpha chain is extracellular and contains the site for ligand binding. The beta chain possesses the transmembrane domain, the tyrosine kinase domain, and a C-terminal extension that is necessary for cell differentiation and transformation, but is dispensable for mitogen signaling and protection from apoptosis.

IGF-1R is highly similar to the insulin receptor (IR), particularly within the beta chain sequence (70% homology). Because of this homology, recent studies have demonstrated that these receptors can form hybrids containing one IR dimer and one IGF-1R dimer (Pandini et al., *Clin. Canc. Res.* 5:1935-19 (1999)). The formation of hybrids occurs in both normal and transformed cells and the hybrid content is dependent upon the concentration of the two homodimer receptors (IR and IGF-1R) within the cell. Although hybrid receptors are composed of IR and IGF-1R pairs, the hybrids bind selectively to IGFs, with affinity similar to that of IGF-1R, and only weakly bind insulin (Siddle and Soos, The IGF System. Humana Press. pp. 199-225 (1999)). These hybrids therefore can bind IGFs and transduce signals in both normal and transformed cells.

A second IGF receptor, IGF-IIR, or mannose-6-phosphate (M6P) receptor, also binds IGF-II ligand with high affinity, but lacks tyrosine kinase activity (Oates et al., *Breast Cancer Res. Treat.* 47:269-81 (1998)). Because it results in the degradation of IGF-II, it is considered a sink for IGF-II, antagonizing the growth promoting effects of this ligand. Loss of the IGF-IIR in tumor cells can enhance growth potential through release of its antagonistic effect on the binding of IGF-II with the IGF-1R (Byrd et al., *J. Biol. Chem.* 274:24408-16 (1999)).

IGF-1R blockade has been described as a tumor treatment; see, e.g., WO06138729, which describes methods of treating bone cancer, particularly metastatic bone cancer, by administering an IGF-1R antagonist and/or a PDGFR antagonist.

Acute respiratory distress syndrome (ARDS), first described in 1967 by Ashbaugh and colleagues (Ashbaugh D. G., et al., *Lancet* 2:319-323 (1967)) remains an important cause of morbidity and mortality in critically ill patients. ARDS is characterized by an acute pulmonary inflammatory process with epithelial apoptosis and interstitial and intra-alveolar edema, followed by fibroblast proliferation, migration, and fibrosis. The diagnosis of ARDS is based on clinical and radiographical criteria, including acute onset, bilateral infiltrates on chest radiograph, absence of congestive heart failure, and hypoxemia (Bernard G. R., et al., *J Crit. Care* 9:72-81 (1994)). This consensus definition has improved the standardization of clinical research and trials; however, it does not take into account the cause or mechanism of disease.

Much work has focused on the identification of humoral or cellular biological markers of ARDS in hopes that such markers may provide insight into the mechanisms of ARDS and improve the prediction of ARDS in high risk patients and prediction of outcome in ARDS patients (Pittet J. F., et al., *Am J Respir Crit. Care Med* 155:1187-1205 (1997)). To date, no single protein marker identified by traditional laboratory methods has demonstrated the specificity or sensitivity to serve as a reliable predictor of outcome.

SUMMARY OF THE INVENTION

The instant invention provides methods and compositions for treatment of acute lung injury, such as but not limited to lung injury resulting from bacterial sepsis, hemorrhagic shock, toxic inhalation, and bleomycin and other drug-induced lung injury. Methods and compositions for the treatment of pulmonary fibrosis are also provided. Additionally, the compositions of the invention are useful in the treatment of fibrosis in epithelial organs, such as lung, liver, kidney, bladder, and esophagus.

One aspect of the present invention is directed to a method for the treatment or prevention of acute lung injury in an individual in need thereof, the method comprising administering an inhibitor of IGF-1R signaling activity to the individual.

Another aspect of the present invention is directed to a method of inhibiting or treating pulmonary fibrosis, the method comprising administering an inhibitor of IGF-1R signaling activity to an individual in need thereof.

Another aspect of the present invention is directed to a pharmaceutical composition comprising an inhibitor of IGF-1R signaling activity formulated for delivery as an aerosol.

Another aspect of the present invention is directed to an aerosol suspension comprising an inhibitor of IGF-1R signaling activity.

Another aspect of the present invention is directed to a composition comprising an inhibitor of IGF-1R signaling activity and a compound selected from the group consisting of a corticosteroid, pirfenidone, IFN-γ, IFN-β, suramin, relaxin, PGE2, indomethacin, an angiotensin II receptor antagonist, captopril, cyclosporine, an anti-oxidant, N-acetyl cysteine, thalidomide, and an endothelin receptor antagonist.

Another aspect of the present invention is directed to the use of an inhibitor of IGF-1R signalling activity for the treatment or prevention of acute lung injury.

Another aspect of the present invention is directed to the use of an inhibitor of IGF-1R for the inhibition or treatment of pulmonary fibrosis, the method comprising administering an inhibitor of IGF-1R signaling activity to an individual in need thereof.

Another aspect of the present invention is directed to the use of an inhibitor of IGF-1R signaling for the inhibition or treatment of pulmonary fibrosis associated with or secondary to a disease or disorder selected from the group consisting of: acute lung injury; ARDS; idiopathic pulmonary fibrosis; interstitial pneumonia; usual interstitial pneumonia; obstructive bronchiolar interstitial pneumonia; desquamative interstitial pneumonia; lymphoid interstitial pneumonia; giant cell interstitial pneumonia; pneumoconiosis; hypersensitivity pneumonitis; radiation pneumonitis; infectious disease; sarcoidosis; histiocytosis X; and a collagen disease.

Another aspect of the present invention is directed to the use of an inhibitor of IGF-1R signaling activity for the treatment or prevention of fibrosis in an epithelial tissue.

Another aspect of the present invention is directed to the use of a soluble IGF-1R or a dominant negative IGF-1R for the treatment or prevention of acute lung injury.

Another aspect of the present invention is directed to the use of an inhibitor of IGF-1R signalling activity in the preparation of a medicament for the treatment or prevention of acute lung injury.

Another aspect of the present invention is directed to the use of an inhibitor of IGF-1R in the preparation of a medicament for the inhibition or treatment of pulmonary fibrosis.

Another aspect of the present invention is directed to the use of an inhibitor of IGF-1R signaling in the preparation of a medicament for the inhibition or treatment of pulmonary fibrosis associated with or secondary to a disease or disorder selected from the group consisting of: acute lung injury; ARDS; idiopathic pulmonary fibrosis; interstitial pneumonia; usual interstitial pneumonia; obstructive bronchiolar interstitial pneumonia; desquamative interstitial pneumonia; lymphoid interstitial pneumonia; giant cell interstitial pneumonia; pneumoconiosis; hypersensitivity pneumonitis; radiation pneumonitis; infectious disease; sarcoidosis; histiocytosis X; and a collagen disease.

Another aspect of the present invention is directed to the use of an inhibitor of IGF-1R signaling activity in the preparation of a medicament for the treatment or prevention of fibrosis in an epithelial tissue.

Another aspect of the present invention is directed to the use of a soluble IGF-1R or a dominant negative IGF-1R in the preparation of a medicament for the treatment or prevention of acute lung injury.

DETAILED DESCRIPTION OF THE INVENTION

Figure 1A:
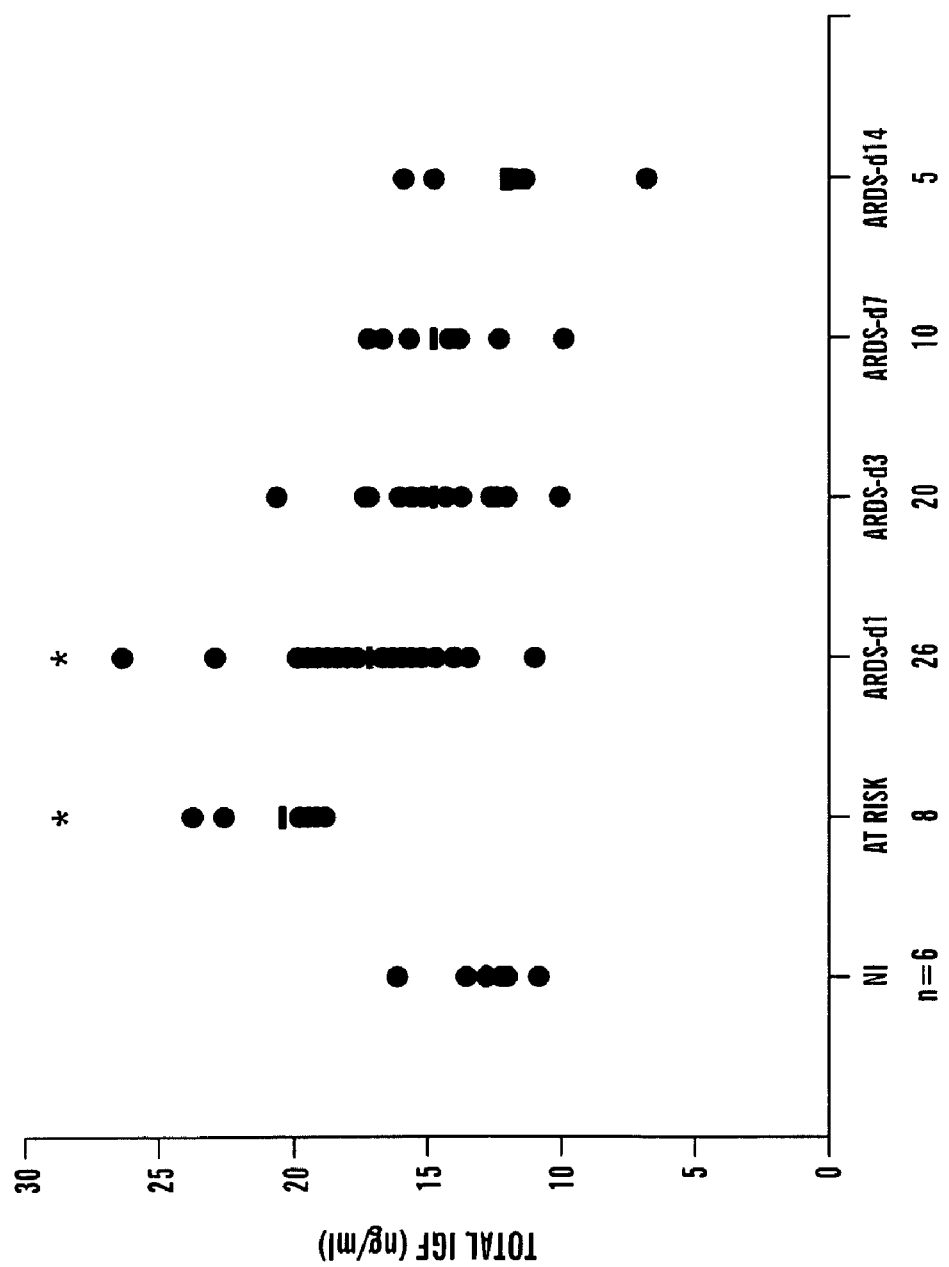
FIG. 1 shows total IGF (A) and free IGF (B) protein concentrations (black circles) in BAL from normal volunteers, patients at-risk for ARDS, and patients with established ARDS studied at sequential times. Total and free IGF was quantified by ELISA kit (Diagnostic Standards Laboratory Systems) per the manufacturer's direction. The concentration of IGF in the samples was determined by interpolation from the standard curve generated with recombinant IGF. All samples were run in duplicate and repeated at least twice. Median (black bars) values are indicated. *, Time points significantly different ($P<0.05$) from controls.

One aspect of the present invention is directed to a method for the treatment or prevention of acute lung injury in an individual in need thereof, the method comprising administering an inhibitor of IGF-1R signaling activity to the individual.

In this and all other aspects described herein, the inhibitor can comprise, for example, a small molecule, an antibody or antigen-binding fragment thereof or a nucleic acid.

In this and all other aspects described herein, an inhibitor that comprises an antibody or antigen-binding fragment thereof can comprise an antibody or antigen-binding fragment thereof that binds the IGF-1R. Such an antibody or antigen-binding fragment thereof can neutralize IGF-1R signaling activity. The antibody or antigen-binding fragment thereof can, for example, bind to the external domain of IGF-1R and inhibit binding of IGF-I or IGF-II to the IGF-1R. The antibody or antigen-binding fragment thereof can alternatively, for example, down-modulate IGF-1R. The antibody or antigen-binding fragment thereof can comprise an antigen-binding domain of the antibody IMC-A12. The antibody or antigen-binding fragment thereof can, for example, bind an epitope bound by the antibody IMC-A12. An antibody inhibitor of IGF-1R signaling can alternatively bind the ligand IGF itself.

In this and all other aspects described herein, nucleic acid inhibitors of IGF-1R signaling can comprise an siRNA that directs the cleavage of IGF-1R mRNA.

In this and all other aspects described herein, the inhibitor(s) of IGF-1R activity can be administered systemically, or, for example, directly to the lung as an aerosol suspension.

Another aspect of the present invention is directed to a method of inhibiting or treating pulmonary fibrosis, the method comprising administering an inhibitor of IGF-1R signaling activity to an individual in need thereof.

In this and all other aspects described herein, the inhibitor can comprise, for example, a small molecule, an antibody or antigen-binding fragment thereof or a nucleic acid.

In this and all other aspects described herein, an inhibitor that comprises an antibody or antigen-binding fragment thereof can comprise an antibody or antigen-binding fragment thereof that binds the IGF-1R. Such an antibody or antigen-binding fragment thereof can neutralize IGF-1R signaling activity. The antibody or antigen-binding fragment thereof can, for example, bind to the external domain of IGF-1R and inhibit binding of IGF-I or IGF-II to the IGF-1R. The antibody or antigen-binding fragment thereof can alternatively, for example, down-modulate IGF-1R. The antibody or antigen-binding fragment thereof can comprise an antigen-binding domain of the antibody IMC-A12. The antibody or antigen-binding fragment thereof can, for example, bind an epitope bound by the antibody IMC-A12. The antibody or antigen-binding fragment thereof can alternatively bind the ligand IGF itself.

In this and all other aspects described herein, nucleic acid inhibitors of IGF-1R signaling can comprise an siRNA that directs the cleavage of IGF-1R mRNA.

In this and all other aspects described herein, the inhibitor of IGF-1R activity can be administered systemically, or, in the alternative, it can be delivered directly to the lung as an aerosol suspension.

Another aspect of the present invention is directed to a pharmaceutical composition comprising an inhibitor of IGF-1R signaling activity formulated for delivery as an aerosol.

In this and all other aspects described herein, the inhibitor can comprise, without limitation, a small molecule, an antibody or antigen-binding fragment thereof or a nucleic acid.

Another aspect of the present invention is directed to an aerosol suspension comprising an inhibitor of IGF-1R signaling activity.

In this and all other aspects described herein, the inhibitor can comprise, without limitation, a small molecule, an antibody or antigen-binding fragment thereof or a nucleic acid.

Another aspect of the present invention is directed to a composition comprising an inhibitor of IGF-1R signaling activity and another composition administered for the treatment of pulmonary fibrosis. For example, the composition can comprise an inhibitor of IGF-1R signaling and a composition selected from the group consisting of a corticosteroid, pirfenidone, IFN-γ, IFN-β, suramin, relaxin, PGE2, indomethacin, an angiotensin II receptor antagonist, captopril, cyclosporine, an anti-oxidant, N-acetyl cysteine, thalidomide, and an endothelin receptor antagonist.

The composition of this and all other aspects can further comprise a pharmaceutically acceptable excipient.

The composition of this and all other aspects can be formulated for administration systemically or, for example, as an aerosol. Thus, the composition of this aspect encompasses an aerosol suspension of the composition.

In this and all other aspects described herein, the inhibitor can comprise, for example, a small molecule, an antibody or antigen-binding fragment thereof or a nucleic acid.

In this and all other aspects described herein, an inhibitor that comprises an antibody or antigen-binding fragment thereof can comprise an antibody or antigen-binding fragment thereof that binds the IGF-1R. Such an antibody or antigen-binding fragment thereof can neutralize IGF-1R signaling activity. The antibody or antigen-binding fragment thereof can, for example, bind to the external domain of IGF-1R and inhibit binding of IGF-I or IGF-II to the IGF-1R. The antibody or antigen-binding fragment thereof can alternatively, for example, down-modulate IGF-1R. The antibody or antigen-binding fragment thereof can comprise an antigen-binding domain of the antibody IMC-A12. The antibody or antigen-binding fragment thereof can alternatively bind the ligand IGF.

In this and all other aspects described herein, nucleic acid inhibitors of IGF-1R signaling can comprise an siRNA that directs the cleavage of IGF-1R mRNA.

Another aspect of the invention described herein includes a method of inhibiting or treating pulmonary fibrosis associated with or secondary to a disease or disorder selected from the group consisting of: acute lung injury; ARDS; idiopathic pulmonary fibrosis; interstitial pneumonia; usual interstitial pneumonia; obstructive bronchiolar interstitial pneumonia; desquamative interstitial pneumonia; lymphoid interstitial pneumonia; giant cell interstitial pneumonia; pneumoconiosis; hypersensitivity pneumonitis; radiation pneumonitis; infectious disease; sarcoidosis; histiocytosis X; and a collagen disease, the method comprising administering an inhibitor of IGF-1R signaling activity to an individual in need thereof.

Another aspect of the invention described herein includes a method for the treatment or prevention of fibrosis in an epithelial tissue in an individual in need thereof, the method comprising administering an inhibitor of IGF-1R signaling activity to the individual.

In this and all other aspects described herein, the tissue can be, for example, one or more of liver, kidney, bladder and esophagus.

Another aspect of the invention described herein includes a method for the treatment or prevention of acute lung injury in an individual in need thereof, the method comprising administering a soluble IGF-1R or a dominant negative IGF-1R to the individual.

Another aspect of the invention described herein includes a method of inhibiting or treating pulmonary fibrosis in an individual in need thereof, the method comprising administering a soluble IGF-1R or a dominant negative IGF-1R to the individual.

As used above, and throughout the description of the present invention, the following terms, unless otherwise indicated, shall be understood to have the following meanings.

As used herein, the term "inhibits a signaling activity" means refers to an agent or treatment that reduces a signaling activity of IGF-1R by at least 20% or more, preferably at least 30%, 40%, 50%, 60%, 70%, 80%, 90%, 95%, 98%, 99% or more, up to and including 100% (complete inhibition) relative to such activity in the absence of that agent or treatment. Inhibition of signaling activity includes inhibition of the expression or abundance of IGF-1R polypeptide.

An "inhibitor" of IGF-1R, as the term is used herein can function in a competitive or non-competitive manner, and can function, in one embodiment, by interfering with the expression of the IGF-1R polypeptide. An IGF-1R inhibitor includes any chemical entity that, upon administration to an individual, results in inhibition of a biological activity caused directly or indirectly by activation of the IGF-1R in response to binding of its natural ligand. Such an inhibitor can act by binding to the intracellular domain of the receptor and blockade of its tyrosine kinase activity. Alternatively, such an inhibitor can act by occupying the ligand binding site or a portion thereof of the IGF-1R, thereby rendering the receptor inaccessible to binding by the natural ligand, which prevents activation by that ligand. Alternatively, such an inhibitor can act by modulating the dimerization of IGF-1R polypeptides, the interaction of IGF-1R with other proteins, or the ubiquitination or endocytic degradation of the receptor. IGF-1R inhibitors, including IGF-1R kinase inhibitors, include, but are not limited to small molecules, antibodies or antigen-binding antibody fragments, antisense constructs, siRNAs and ribozymes. Various types of inhibitors useful in the methods and compositions disclosed herein are described in further detail herein below.

As used herein, the term "acute lung injury" (ALI) is an umbrella term for hypoxemic respiratory failure, a severe version of which is "Acute Respiratory Distress Syndrome" (ARDS). The clinical diagnostic characteristics include bilateral pulmonary infiltrates on chest x-ray, Pulmonary Capillary Wedge Pressure <18 mmHg, PaO2/FiO2<300 ALI, and PaO2/FiO2<200=ARDS. Although not strictly part of the clinical diagnostic definition, there is generally widespread airway collapse (low lung volumes), surfactant deficiency and reduced lung compliance. ALI is most often seen as part of a systemic inflammatory process, particularly systemic sepsis, where the lung manifestations parallel those of other tissues—widespread destruction of the capillary endothelium, extravascation of protein rich fluid and interstitial edema. In addition, the alveolar basement membrane is damaged, and fluid seeps into the airspaces, stiffening the lungs and causing ventilation-perfusion mismatch. Other causes of ARDS include, for example, pneumonia, major trauma, pulmonary aspiration and near drowning, burns, inhalation of noxious fumes, fat embolism, massive blood transfusion, amniotic fluid embolism, air embolism, eclampsia, poisoning and radiation.

"Treatment" of a respiratory disorder, acute lung injury or fibrosis as referred to herein refers to therapeutic intervention that stabilizes or improves the function of the lung or the airway. That is, "treatment" is oriented to the function of the respiratory tract. A therapeutic approach that stabilizes or improves the function of the lung or the airway by at least 10%, and preferably by at least 20%, 30%, 40%, 50%, 75%, 90%, 100% or more, e.g., 2-fold, 5-fold, 10-fold or more, up to and including full function, relative to such function prior to such therapy is considered effective treatment. Effective treatment need not cure or directly impact the underlying cause of the respiratory disease or disorder to be considered effective treatment. It is particularly noted that a "treatment" as the term is used herein can stabilize or improve respiratory function without necessarily, for example, killing an infectious agent or killing a tumor.

As used herein, "prevention" or "preventing," when used in reference to a disease, disorder or symptoms thereof, refers to a reduction in the likelihood that an individual will develop a disease of disorder, e.g., a respiratory disorder. The likelihood of developing a disease or disorder is reduced, for example, when an individual having one or more risk factors for a disease or disorder either fails to develop the disorder or develops such disease or disorder at a later time or with less severity, statistically speaking, relative to a population having the same risk factors and not receiving treatment as described herein. The failure to develop symptoms of a disease, or the development of reduced (e.g., by at least 10% on a clinically accepted scale for that disease or disorder) or delayed (e.g., by days, weeks, months or years) symptoms is considered effective prevention.

As used herein, the term "specifically binds" refers to binding with a dissociation constant ($K_d$) of 100 µM or lower, e.g., 75 µM, 60 µM, 50 µM, 40 µM, 30 µM, 20 µM, 10 µM, 1 µM, 100 nM, 50 nM, 10 nM, 1 nM or less.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

An "RNA interfering agent" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), and small molecules which interfere with or inhibit expression of a target gene by RNA interference (RNAi).

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice of the present invention, the preferred methods and materials are now described. All publications mentioned herein are incorporated herein by reference to disclose and described the methods and/or materials in connection with which the publications are cited.

The invention relates to methods and compositions for the treatment of a respiratory disease or disorder, or treatment of a fibrotic disease or disorder, through inhibition of the insulin-like growth factor-I receptor (IGF-1R). Thus, encompassed are treatments for a respiratory disease or disorder, or for a fibrotic disease or disorder, the treatment involving administration of an inhibitor of at least one signaling activity of IGF-1R to an individual in need of such treatment. In particular embodiments, the disease or disorder is acute lung injury, ARDS or pulmonary fibrosis.

In the methods described herein, inhibition of IGF-1R signaling activity is achieved through administration of agents including, for example, a small molecule inhibitor of IGF-1R, an antibody or antigen-binding fragment thereof, and a nucleic acid that inhibits IGF-1R. IGF-1R inhibitory agents can be administered alone or in combination with other agents, e.g., anti-inflammatories or other agents used for the treatment of fibrotic diseases or disorders.

Also encompassed herein are compositions comprising an inhibitor of IGF-1R signaling and one or more additional therapeutic compositions, preferably in further combination with a pharmaceutically acceptable excipient. In preferred embodiments, compositions are encompassed in which an inhibitor of IGF-1R is combined with an agent, such as an anti-inflammatory agent, including, for example, a corticosteroid, which is commonly used as a first-line therapeutic approach for the treatment of acute lung injury or pulmonary fibrosis.

The inventors have discovered that the inhibition of signaling through the insulin-like growth factor-I receptor (IGF-1R) can inhibit fibrosis in vivo. The present invention thus relates to the inhibition of the IGF signaling pathway for the treatment of diseases or disorders involving or characterized by fibrosis. The invention thus further relates to the inhibition of signaling through the IGF-1R for the treatment of such diseases or disorders. Therefore, described herein are methods for the treatment or prevention of diseases or disorders involving or characterized by fibrosis, the methods comprising administering an inhibitor of IGF-1R signaling to an individual in need of such treatment.

While not intending to be limited to such, diseases of particular interest include acute lung injury and respiratory diseases or disorders involving or characterized by pulmonary fibrosis. Such disease or disorder includes, for example, pulmonary fibrosis induced by acute injury or trauma, e.g., as caused by infection or inhalation of a noxious agent, as well as idiopathic pulmonary fibrosis (IPF, also known as usual idiopathic pneumonia, or UIP) and other similar pulmonary disorders.

Approaches for the inhibition of IGF-1R signaling activity include, but are not limited to the administration of agents including, for example, a small molecule inhibitor of IGF-1R, an antibody or antigen-binding fragment thereof, and a nucleic acid that inhibits IGF-1R.

Also described herein are compositions comprising an inhibitor of IGF-1R signaling and one or more additional therapeutic compositions, preferably in further combination with a pharmaceutically acceptable excipient.

Respiratory Diseases or Disorders

Respiratory diseases or disorders for which the inhibition of IGF-1R activity can be beneficial include acute lung injury (ALI, including the severe form ARDS) and lung diseases or disorders involving fibrosis and/or inflammation of tissues of the lung. In particular, ALI, as well as diseases or disorders characterized by, inducing or involving pulmonary fibrosis are seen as candidates for therapy involving inhibition of IGF-1R signaling activity.

The clinical markers of ALI and ARDS are described herein above in the definition of "acute lung injury." Further detail can be found, for example, in the following references: Bernard et al., *Am. J. Respir. Crit. Care Med.* 149: 818-824 (1994); Ware & Matthay, *N. Engl. J. Med.* 342: 1334-1349 (2000); Ashbaugh et al., *Lancet* 2(7511): 319-323 (1967); Petty, *Am. J. Respir. Crit. Care Med.* 163: 602-603 (2001); and Bigelow et al., *Med. Clin. North Am.* 51: 323-340 (1967).

As discussed in the Background, pulmonary fibrosis of unknown etiology is known as Idiopathic Pulmonary Fibrosis (IPF). It is of insidious onset with nonproductive cough and dyspnea. The pathology of IPF is multifactorial. Bronchoalveolar lavage shows an increase in PMNs, eosinophils, alveolar macrophages, and lymphocytes, as well as increased levels of cytokines, growth factors, and immune complexes. The common final pathway is fibrosis of lung parenchyma with increasing respiratory insufficiency and eventual respiratory failure.

The American Thoracic Society recognizes two diagnostic criteria for IPF, set out as A and B below.

Diagnostic Criterion A:

In the setting of a surgical biopsy showing usual interstitial pneumonia (UIP), these three conditions must be met:

Exclusion of other known causes of interstitial lung disease, such as certain drug toxicities, environmental exposures, and connective tissue diseases.

Abnormal pulmonary function studies that include evidence of restriction (reduced vital capacity (VC) often with an increased Fev1/FVC ratio) and/or impaired gas exchange (increased alveolar-arterial gradient for $O_2$ or decreased diffusion capacity for CO).

Bibasilar reticular abnormalities with minimal ground glass opacities on HRCT scans.

Diagnostic Criterion B:

In the absence of a surgical lung biopsy, in an immunocompetent adult, a presumed diagnosis of IPF may be made if:

All three criteria set out in Criterion A are met;

A transbronchial lung biopsy (TBBx) or bonchoalveolar lavage (BAL) shows no features to support an alternative diagnosis; or Three of the following four minor criteria are met: 1. Age>50; 2. Insidious onset of unexplained dyspnea on exertion; 3. Duration of illness>three months; and 4. Bibasilar inspiratory crackles.

Frequently, the subject suffering from IPF is unresponsive to treatment with one or more of a corticosteroid, cyclophosphamide, and azathioprine drug. Thus, these patients, in particular, and among others, are contemplated as appropriate for treatment using methods as disclosed herein. Furthermore, in patients that are minimally responsive to immunosuppressant therapies, wherein there is a modest, but insignificant improvement in pulmonary function tests, it is a further aspect of the methods described herein to combine treatment of these patients with an inhibitor of IGF-1R while maintaining treatment with one or more other therapeutic regimens, including but not limited to treatment with immunosuppressive or anti-inflammatory agents.

Interstitial pneumonia is an inflammation of lung stroma, which means an inflammation of alveolar wall and peripheral supporting tissue. While it includes local and diffuse pneumonia, interstitial pneumonia generally means diffuse interstitial pneumonia, including acute type and chronic type. Histologically, it is classified into five types: UIP (usual or classical interstitial pneumonia); BIP (obstructive bronchiolar interstitial pneumonia); DIP (desquamative interstitial pneumonia); LIP (lymphoid interstitial pneumonia); and GIP (giant cell interstitial pneumonia). Those having an unknown cause are called idiopathic pulmonary fibrosis (IPF). Those having a known cause include pneumoconiosis, hypersensitivity pneumonitis, radiation pneumonitis, infectious disease and the like. The disease sometimes accompanies a systemic disease, such as sarcoidosis, histiocytosis X, collagen disease and the like. Clinically, dry coughing, exertional dyspnea, fever, clubbing of finger, cyanosis and the like are observed.

Pulmonary fibrosis in interstitial pneumonia is pathologically alveolar septal tylosis, mainly characterized by growth of type II alveolar epithelial cells and fibroblast, and an increase in the collagen fibers produced by fibroblasts. Its etiology is not certain, but involvement of various cytokines is postulated. That is, known cellular groups involved therein are fibroblasts, smooth muscle cells, hematocyte-derived macrophages, lymphocytes, neutrophils, acidocytes and basocytes, all of which are mesenchymal cells, plus epithelial cells, including alveolar epithelial cells, respiratory epithelial cells, and vascular endothelial cells, among others. These cells are activated by inflammatory stimuli, express various cytokines upon activation, and induce changes in adhesion molecules. Through these effects, pulmonary tissues are damaged, which triggers proliferation of type II alveolar epithelial cell and fibroblasts, thereby advancing fibrosis.

Inhibitors of IGF-1R

The methods described herein involve the administration of IGF-1R inhibitors for the treatment of disease. A number of inhibitors of IGF-1R activities are known in the art. Inhibitors can inhibit, for example, IGF-1R ligand binding, IGF-1R enzyme activity, IGF-1R interaction with enzymatic substrates, and/or expression or stability of the IGF-1R protein itself. One issue encountered in the design of specific inhibitors of IGF-1R is the similarity of the IGF-I receptor to the insulin receptor (IR). Agents that cross-react with the insulin receptor would be expected to have deleterious consequences when administered to mammals, so an inhibitor of IGF-1R useful in the methods described herein must be specific for IGF-1R. By "specific" in this context is meant that the inhibitor does not inhibit insulin receptor (i.e., inhibits IR signaling by less than or equal to 5%) at a concentration at which IGF-1R signaling activity is inhibited by 95%. Insulin receptor inhibition can be measured by one of skill in the art.

Inhibitors of IGF-1R signaling include, for example, small molecule inhibitors, anti-IGF-1R antibodies or antigen-binding fragments thereof and nucleic acid inhibitors, most notably siRNAs specific for IGF-1R mRNA. Such inhibitors are discussed separately below. Also included are anti-IGF antibodies or antigen-binding fragments thereof (i.e., anti-ligand antibodies) and soluble IGF-1R, both of which prevent IGF from binding and activating the receptor.

Ligand binding triggers IGF-1R signaling activity. The term "IGF-1R signaling activity" encompasses all cell signaling events regulated or influenced by IGF ligand binding to the IGF-1R, including, but not limited to IGF-1R tyrosine autophosphorylation in the tyrosine kinase domain (which spans AAs 973-1229) of the P subunit) and tyrosine phosphorylation of other substrates by the receptor's activated tyrosine kinase. Key tyrosine autophosphorylation sites include the clustered tyrosines at positions 1131, 1135 and 1136 of the IFG-1R β subunit. Among heterologous substrates are, for example, Insulin Receptor Substrate-1 (IRS-1), Protein Kinase B (PKB; also known as Akt), Shc and Erk-2. Phosphorylation of IRS-1 leads to activation of phosphatidylinositol 3-kinase pathway, and phosphorylation of Shc leads to activation of the MAPK signaling pathway. Thus, PI3 Kinase activity, Shc phosphorylation and MAPK cascade activation can also be monitored as indirect measures of IGF-1R activity.

Activation of IGF-1R signaling activity can be inhibited by, for example, agents that bind the receptor and inhibit ligand binding, or, for example, agents that bind the receptor and inhibit its enzymatic activity or its association with substrate polypeptides. As one measure, IGF-1R signaling activity is considered "inhibited" if the receptor's tyrosine kinase activity is reduced by at least 75% in the presence of the inhibitor relative to its absence.

Receptor autophosphorylation can be monitored, for example, by ELISA or immunoprecipitation with commercially available anti-phosphotyrosine antibodies. In one aspect, detection after binding with anti-phosphotyrosine antibodies is permitted by Western blot probing with anti-IGF-1R antibodies. Tyrosine phosphorylation of IGF-1R kinase substrates such as IRS-1, PKB and Erk-2 can be monitored using anti-phosphotyrosine antibodies in an ELISA or Western blot format. Alternatively, antibodies are available for phosphorylated forms of substrates, including, for example, anti-phospho IRS-1 (Oncogene Research Products, Germany), anti-phospho Akt/PKB (Cell Signaling Technology).

Small Molecule Inhibitors of IGF-1R Signaling

Small molecule inhibitors of IGF-1R include, for example, AG 538, a substrate-competitive agent described by Blum et al. (*Biochemistry* 39: 15705-15712 (2000), incorporated herein by reference), which inhibits IGF-1R with an $IC_{50}$ of 61 nM in a cell free kinase assay. The agent inhibits receptor autophosphorylation as well as activation of downstream targets PKB and Erk2 in cultured cells. The catechol moiety of AG 538 is unstable due to its vulnerability to oxidation. This property led the investigators to design a series of substrate-competitive inhibitors in which the catechol moiety, which mimics the phenol group of the substrate tyrosine moiety, is replaced by bioisosteres. The synthesis and IGF-1R inhibition activity of these derivatives is reported in Blum et al. (2003, J. Biol. Chem. 278: 40442-40454, incorporated herein by reference). In particular, a group of molecules is described in which the catechol group is replaced with a benzoxazolone group on either side of the molecule—the benzoxazolone group is thought to function as a bioisistere of the catechol moiety, thus maintaining the bioactivity of the compound. In particular, the compounds listed in Table I of the Blum et al. JBC reference have $IC_{50}$ values for inhibition of IGF-1R autophosphorylation in the range of 59±5 µM to 0.06±0.02 µM. In particular, compounds designated #4 (GB 19) and #10 (AGL 2263) therein, while somewhat less active than parent compound AG 538 in cell free assays, were comparable to the parent compound in cell culture assays, most likely due to enhanced stability in cells relative to the parent compound. The GB19 and AGL 2263 compounds were selective inhibitors of IGF-1R, inhibiting the activation of PKB in intact cells with IC50 values of 12 and 6 µM, respectively. These compounds did not affect PKB activation by PDGFR in intact cells, thus confirming their selectivity. It is noted that because these agents are substrate-competitive inhibitors, somewhat higher concentrations are required to inhibit IGF-1R autophosphorylation activity than, for example, PKB or IRS-1 phosphorylation. This is likely because autophosphorylation is intermolecular trans-autophosphorylation within the IGF-1R dimer—the local substrate concentration is much higher than the concentration of exogenous substrates such as IRS-1 or PBK. These selective small molecule inhibitors of IGF-1R, as well as the parent AG 538 molecule, and derivatives and pharmaceutically acceptable salts or esters of them that maintain bioactivity against IGF-1R tyrosine kinase activity, are specifically contemplated for use in the methods and compositions described herein.

Gimita et al. (*Cancer Res.* 64: 236-242 (2004)) describe a class of cyclolignans as specific inhibitors of IGF-1R. The authors of that study analyzed by computer the three dimensional folding of short peptides having the amino acid sequence of the IGF-1R tyrosine domain, including the tyrosine residues at positions 1131, 1135 and 1136. They found using a 12 amino acid peptide that the hydroxyl groups of two of the three key tyrosines, those at 1135 and 1136, which must be autophosphorylated for receptor tyrosine kinase activity, could be situated as close as 9.5 angstroms from each other and that the apparent angle between the tyrosines was approximately 60°. This short distance is not observed in the very similar insulin receptor (IR). A molecule that recognizes this structure was anticipated to inhibit IGF-1R activation without affecting IR activation. Using this guidance, Girnita et al. discovered that two cyclolignan compounds, podophyllotoxin (PPT) and picropodophyllin (PPP) had strong inhibitory effects (sub-micromolar $IC_{50}$) on IGF-1R activity and did not affect IR activity, even at high concentrations. One of these, PPP, was studied in detail and shown to be essentially non-toxic ($LD_{50}$ in rats of >500 mg/kg), yet effective at killing IGF-1R-positive tumors in mice. This highly selective small molecule inhibitor of IGF-1R signaling activity is considered appropriate for the methods and compositions described herein. The other cytolignan, PPT, was known to be cytotoxic due to an interaction with β-tubulin that leads to mitotic arrest, and would not be considered useful in the methods and compositions described herein. Derivatives and pharmaceutically acceptable salts and esters of the PPP molecule that maintain IGF-1R inhibitory activity (e.g., that continue to mimic the tyrosine arrangement of the IGF-1R that distinguishes IGF-1R from the IR) without inhibition of IR activity, are specifically contemplated as useful within the methods and compositions described herein.

More recently, Gable et al. (*Mol. Cancer Ther.* 5: 1079-1086 (2006)) have described the discovery of diarylureas as a class of small molecule inhibitors of IGF-1R signaling. Those authors describe one phenyl-4-quinolyl urea class compound, termed PQ401 that inhibits autophosphorylation with an $IC_{50}$ of 12 □M in cultured cells and an $IC_{50}$ less than 1 □M against isolated IGF-1R kinase domain. The compound was shown to reduce the growth rate of tumors in nude mice. The exact mechanism of inhibition was not reported therein; however, critical structure of the inhibitor is highlighted by data showing that a negative control diaryl urea compound termed PQ20, which has an identical structure of both the aryl ring and the urea linker but a different substitution position on the quinolyl ring (a 3 quinolyl group replacing the methyl-substituted 4 quinolyl group of the PQ401 compound), had no kinase inhibiting activity. Derivatives and pharmaceutically acceptable salts and esters that maintain the structure of the 4-quinolyl-substituted compound are expected to maintain IGF-1R inhibiting activity. PQ401 and compounds derived from it that maintain IGF-1R inhibitory activity are contemplated for use in the compositions and methods described herein.

The compound cis-3-[3-(4-methyl-piperazin-1-yl)-cyclobutyl]-1-(2-phenyl-quinolin-7-yl)-imidazo[1,5-a]pyrazin-8-ylamine is another small molecule found by OSI Pharmaceuticals to inhibit the in vivo activity of IGF-1R. The compound was shown to inhibit IGF-1R activity in vivo without causing any substantial rise in blood sugar, highlighting a lack of activity against IR. This compound and derivatives and pharmaceutically acceptable salts and esters that maintain IGF-1R inhibitory activity are specifically contemplated for use in the methods and compositions described herein.

Additional small molecule IFG-1R inhibitors are described in WO2007035744, which is incorporated herein by reference.

Antibodies

Inhibitors of IGF-1R useful in the methods described herein include, but are not limited to antibodies or antigen-binding fragments thereof specific for IGF-1R. Also encompassed in some embodiments are antibodies or antigen-binding fragments of antibodies that specifically bind and neutralize IGF, i.e., anti-ligand antibodies. Endocrine expression of IGF-1 is regulated primarily by growth hormone and produced in the liver, but other tissue types are also capable of expressing IGF-I, including bone which contains a large store of growth factors. Depending on tumor cell type, IGF-1 is involved in endocrine, paracrine, and/or autocrine regulation (Yu, H. and Rohan, J., *J. Natl. Cancer Inst.* 92:1472-89 (2000)).

It has been reported elsewhere that antibodies that bind IGF-1R are useful in therapies for treatment of bone tumors that express IGF-1R. Such antibodies are also useful in the treatment methods and compositions described herein. The antibodies can be used alone, or in combination with other therapeutics, particularly anti-inflammatories, including corticosteroids, among others. Other agents useful in combination with IGF-1R inhibitors described herein (regardless of whether antibody, small molecule or nucleic acid based) include, for example, pirfenidone, IFN-γ, IFN-β, suramin, relaxin, PGE2, indomethacin, inhibitors of leukotriene synthesis, angiotensin II receptor antagonists, captopril, N-acetyl cysteine and other anti-oxidants, thalidomide, and endothelin receptor antagonists to name a representative few. Anti-IGF-1R therapy, alone or in combination with therapy with one or more such agents can have significant therapeutic efficacy.

In an embodiment of the methods and compositions described herein, the anti-IGF-1R antibodies bind to IGF-1R and block ligand binding. In another embodiment, the anti-IGF-1R antibodies bind to IGF-1R and promote reduction in IGF-1R surface receptor. In yet another embodiment of the invention, the antibodies bind to IGF-1R and inhibit IGF-1R mediated signal transduction.

In certain embodiments, the antibodies bind to IGF-1R with a $K_d$ of about $3 \times 10^{-10}$ $M^{-1}$ or less. The anti-IGF-1R antibody can be IMC-A12, or an antibody that competes with IMC-A12 for binding to the receptor. Antibodies that can be used according to the invention include chimeric and humanized antibodies. In a preferred embodiment, the antibody is human.

Anti-IGF-1R antibodies to be used according to the present invention exhibit one or more of following properties:

The antibodies bind to the external domain of IGF-1R and inhibit binding of IGF-I or IGF-II to IGF-1R. Inhibition can be determined, for example, by a direct binding assay using purified or membrane bound receptor. In this embodiment, the antibodies of the present invention, or fragments thereof, preferably bind IGF-1R at least as strongly as the natural ligands of IGF-1R (IGF-I and IGF-II).

The antibodies neutralize IGF-1R. Binding of a ligand, e.g., IGF-I or IGF-II, to an external, extracellular domain of IGF-1R stimulates autophosphorylation of the beta subunit and phosphorylation of IFG-1R substrates, including MAPK, Akt, and IRS-1.

Neutralization of IGF-1R includes inhibition, diminution, inactivation and/or disruption of one or more of these activities normally associated with signal transduction. Neutralization can be determined in vivo, ex vivo, or in vitro using, for example, tissues, cultured cell, or purified cellular components. Neutralization includes inhibition of IGF-1R/IR heterodimers as well as IGF-1R homodimers. Thus, neutralizing IGF-1R has various effects, including inhibition, diminution, inactivation and/or disruption of fibrogenesis, growth (proliferation and differentiation), angiogenesis (blood vessel recruitment, invasion, and metastasis), and cell motility and metastasis (cell adhesion and invasiveness).

One measure of IGF-1R neutralization is inhibition of the tyrosine kinase activity of the receptor. Tyrosine kinase inhibition can be determined using well-known methods; for example, by measuring the autophosphorylation level of recombinant kinase receptor, and/or phosphorylation of natural or synthetic substrates. Thus, phosphorylation assays are useful in determining neutralizing antibodies or neutralization by other agents in the context of the present invention. Phosphorylation can be detected, for example, using an antibody specific for phosphotyrosine in an ELISA assay or on a western blot. Some assays for tyrosine kinase activity are described in Panek et al., *J. Pharmacol. Exp. Thera.* 283: 1433-44 (1997) and Batley et al., *Life Sci.* 62:143-50 (1998). Antibodies of the invention cause a decrease in tyrosine phosphorylation of IGF-1R of at least about 75%, preferably at least about 85%, and more preferably at least about 90% in cells that respond to ligand.

Another measure of IGF-1R neutralization is inhibition of phosphorylation of downstream substrates of IGF-1R. Accordingly, the level of phosphorylation of MAPK, Akt, or IRS-1 can be measured. The decrease in substrate phosphorylation is at least about 50%, preferably at least about 65%, more preferably at least about 80%.

In addition, methods for detection of protein expression can be utilized to determine IGF-1R neutralization, wherein the proteins being measured are regulated by IGF-1R tyrosine kinase activity. These methods include immunohistochemistry (IHC) for detection of protein expression, fluorescence in situ hybridization (FISH) for detection of gene amplification, competitive radioligand binding assays, solid matrix blotting techniques, such as Northern and Southern blots, reverse transcriptase polymerase chain reaction (RT-PCR) and ELISA. See, e.g., Grandis et al., *Cancer,* 78:1284-92 (1996); Shimizu et al., *Japan J. Cancer Res.,* 85:567-71 (1994); Sauter et al., *Am. J. Path.,* 148:1047-53 (1996); Collins, *Glia* 15:289-96 (1995); Radinsky et al., *Clin. Cancer Res.* 1:19-31 (1995); Petrides et al., *Cancer Res.* 50:3934-39 (1990); Hoffmann et al., *Anticancer Res.* 17:4419-26 (1997); Wikstrand et al., *Cancer Res.* 55:3140-48 (1995).

Ex vivo assays can also be utilized to determine IGF-1R neutralization. For example, receptor tyrosine kinase inhibition can be observed by mitogenic assays using cell lines stimulated with receptor ligand in the presence and absence of inhibitor. The MCF7 breast cancer line (American Type Culture Collection (ATCC), Rockville, Md.) is such a cell line that expresses IGF-1R and is stimulated by IGF-I or IGF-II. Another method involves testing for inhibition of growth of IGF-1R-expressing tumor cells or cells transfected to express IGF-1R. Inhibition can also be observed using tumor models, for example, human tumor cells injected into a mouse.

The antibodies useful in the methods and compositions described herein are not limited by any particular mechanism of IGF-1R neutralization. The anti-IGF-1R antibodies of the present invention can bind externally to the IGF-1R cell surface receptor, block binding of ligand (e.g., IGF-I or IGF-II) and subsequent signal transduction mediated via the receptor-associated tyrosine kinase, and prevent phosphorylation of the IGF-1R and other downstream proteins in the signal transduction cascade.

3) The antibodies down modulate IGF-1R. The amount of IGF-1R present on the surface of a cell depends on receptor protein production, internalization, and degradation. The amount of IGF-1R present on the surface of a cell can be measured indirectly, by detecting internalization of the receptor or a molecule bound to the receptor. For example, receptor internalization can be measured by contacting cells that express IGF-1R with a labeled antibody. Membrane-bound antibody is then stripped, collected and counted. Internalized antibody is determined by lysing the cells and detecting label in the lysates.

Another way is to directly measure the amount of the receptor present on the cell following treatment with an anti-IGF-1R antibody or other substance, for example, by fluorescence-activated cell-sorting analysis of cells stained for surface expression of IGF-1R. Stained cells are incubated at 37° C. and fluorescence intensity measured over time. As a control, part of the stained population can be incubated at 4° C. (conditions under which receptor internalization is halted).

Cell surface IGF-1R can be detected and measured using a different antibody that is specific for IGF-1R and that does not block or compete with binding of the antibody being tested. (Burtrum, et al. *Cancer Res.* 63:8912-21 (2003)) Treatment of an IGF-1R expressing cell with an antibody of the invention results in reduction of cell surface IGF-1R. In a preferred embodiment, the reduction is at least about 70%, more preferably at least about 80%, and even more preferably at least about 90% in response to treatment with an antibody of the invention. A significant decrease can be observed in as little as four hours.

Another measure of down-modulation is reduction of the total receptor protein present in a cell, and reflects degradation of internal receptors. Accordingly, treatment of cells with anti-IGF-1R antibodies results in a reduction in total cellular IGF-1R. In a preferred embodiment, the reduction is at least about 70%, more preferably at least about 80%, and even more preferably at least about 90%.

For treatment of human subjects, the antibodies are preferably human antibodies, but can also be humanized or chimeric antibodies. One preferred human antibody is IMC-A12 (WO2005016970). Another preferred human antibody is IMC-2F8 (WO2005016970). Useful antibodies further include anti-IGF-1R antibodies that compete with IMC-A12 or IMC-2F8 for binding to IGF-1R, as well as antibodies that bind to other epitopes (i.e., antibodies that bind to other epitopes and exhibit properties as previously described such as ligand blocking, receptor internalization, etc., but do not compete with IMC-A12 or IMC-2F8).

Antibodies that can be used according to the invention include complete immunoglobulins, antigen binding fragments of immunoglobulins, as well as antigen binding proteins that comprise antigen binding domains of immunoglobulins. Antigen binding fragments of immunoglobulins include, for example, Fab, Fab', and F(ab')$_2$. Other antibody formats have been developed which retain binding specificity, but have other characteristics that may be desirable, including for example, bispecificity, multivalence (more than two binding sites), compact size (e.g., binding domains alone).

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

Multiple single chain antibodies, each single chain having one $V_H$ and one $V_L$ domain covalently linked by a first peptide linker, can be covalently linked by at least one or more peptide linker to form a multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of amino acid residues is about one hundred.

Two single chain antibodies can be combined to form a diabody, also known as a bivalent dimer. Diabodies have two chains and two binding sites, and can be monospecific or bispecific. Each chain of the diabody includes a $V_H$ domain connected to a $V_L$ domain. The domains are connected with linkers that are short enough to prevent pairing between domains on the same chain, thus driving the pairing between complementary domains on different chains to recreate the two antigen-binding sites.

Three single chain antibodies can be combined to form triabodies, also known as trivalent trimers. Triabodies are constructed with the amino acid terminus of a $V_L$ or $V_H$ domain directly fused to the carboxyl terminus of a $V_L$ or $V_H$ domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific.

Thus, antibodies of the invention and fragments thereof include, but are not limited to, naturally occurring antibodies, bivalent fragments such as (Fab')$_2$, monovalent fragments such as Fab, single chain antibodies, single chain Fv (scFv), single domain antibodies, multivalent single chain antibodies, diabodies, triabodies, and the like that bind specifically with antigens.

Other polypeptide-based inhibitors of IGF-1R signaling include soluble IGF-1R molecules. The production and use of soluble receptor molecules to inhibit receptor signaling are known in the art and are within the ability of one of ordinary skill in the art. For example, Etanercept™, used for the treatment of inflammatory disorders and marketed by Amgen, Inc. and Wyeth Pharmaceuticals, is a soluble TNF receptor. Soluble IGF-1R is described, for example, in U.S. Pat. No. 6,084,085, which is incorporated herein by reference.

Another class of polypeptide-based inhibitors of IGF-1R signaling includes dominant-negative IGF-1R. See, for example, Dunn et al., Cancer Res. 58: 3353-3361 (1998) and Lee et al., Cancer Gene Therapy 10: 57-63 (2003), both of which are incorporated herein by reference, for description of the production and use of dominant-negative IGF-1R to inhibit IGF-1R signaling. The Lee et al. reference, in particular, describes the use of virally-mediated expression of dominant-negative IGF-1R to inhibit tumor growth in vivo. A similar approach can be used to deliver IGF-1R to areas in need of treatment or prevention of fibrosis.

Nucleic Acids

IGF-1R activity can be reduced by treatment with nucleic acids that target the expression of the IGF-1R polypeptide. Thus, for example, antisense molecules, including antisense oligonucleotides and e.g., larger antisense molecules expressed from nucleic acid constructs administered to an individual are contemplated for use in the methods and compositions described herein. The use of antisense sequences directed at human IGF-1R is described, for example, in U.S. Pat. No. 6,541,036, which is incorporated herein by reference. That reference describes the use of antisense technology for the treatment of cancer.

The expression of IGF-1R can also be targeted through the phenomenon of RNA interference, or RNAi. RNAi uses small interfering RNA (siRNA) duplexes that target the messenger RNA encoding the target polypeptide for selective degradation. siRNA-dependent post-transcriptional silencing of gene expression involves cutting the target messenger RNA molecule at a site guided by the siRNA.

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B., J. of Virology 76(18):9225 (2002)), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease may be of at least 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shRNAs may be encoded by plasmids, retroviruses, and lentiviruses and expressed from, for example, the pol III U6 promoter, or another promoter (see, e.g., Stewart, et al., *RNA* April; 9(4): 493-501 (2003), incorporated by reference herein in its entirety).

The target gene or sequence of the RNA interfering agent may be a cellular gene or genomic sequence, e.g. the IGF-1R sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al., *Nature Biotechnology* 6:635-637 (2003). In addition to expression profiling, one may also screen the potential target sequences for similar sequences in the sequence databases to identify potential sequences which may have off-target effects. For example, according to Jackson et al. (Id.) 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'-O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LNA) nucleotides and RNA duplexes containing either phosphodiester or varying numbers of phosphorothioate linkages. Such modifications are known to one skilled in the art and are described, for example, in Braasch et al., *Biochemistry* 42: 7967-7975 (2003). Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

siRNAs useful for targeting IGF-1R expression can be readily designed and tested. Chalk et al. (*Nucl. Acids Res.* 33: D131-D134 (2005)) describe a database of siRNA sequences and a predictor of siRNA sequences. Linked to the sequences in the database is information such as siRNA thermodynamic properties and the potential for sequence-specific off-target effects. The database and associated predictive tools enable the user to evaluate an siRNA's potential for inhibition and non-specific effects. The database is available at http://siRNA.cgb.ki.se.

siRNAs useful for the methods described herein include siRNA molecules of about 15 to about 40 or about 15 to about 28 nucleotides in length, which are homologous to an IGF-1R gene, preferably a human IGF-1R gene sequence. Preferably, the siRNA molecules have a length of about 19 to about 25 nucleotides. More preferably, the siRNA molecules have a length of about 19, 20, 21, or 22 nucleotides. The siRNA molecules can also comprise a 3' hydroxyl group. The siRNA molecules can be single-stranded or double stranded; such molecules can be blunt ended or comprise overhanging ends (e.g., 5', 3'). In specific embodiments, the RNA molecule is double stranded and either blunt ended or comprises overhanging ends.

In one embodiment, at least one strand of the RNA molecule has a 3' overhang from about 0 to about 6 nucleotides (e.g., pyrimidine nucleotides, purine nucleotides) in length.

In other embodiments, the 3' overhang is from about 1 to about 5 nucleotides, from about 1 to about 3 nucleotides and from about 2 to about 4 nucleotides in length. In one embodiment the RNA molecule is double stranded, one strand has a 3' overhang and the other strand can be blunt-ended or have an overhang. In the embodiment in which the RNA molecule is double stranded and both strands comprise an overhang, the length of the overhangs may be the same or different for each strand. In a particular embodiment, the RNA of the present invention comprises about 19, 20, 21, or 22 nucleotides which are paired and which have overhangs of from about 1 to about 3, particularly about 2, nucleotides on both 3' ends of the RNA. In one embodiment, the 3' overhangs can be stabilized against degradation. In a preferred embodiment, the RNA is stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

siRNAs effective to target and inhibit IGF-1R activity have been described, e.g., by Liao & Wang (*Oligonucleotides* 15: 196-205 (2005)), which is incorporated herein by reference. Sequences for siRNAs effective to target human IGF-1R mRNA include the following. siRNA 1: 5'-GGGACCCUC-CUCCGGAGCCAG-3' (antisense; SEQ ID NO: 1) and 5'-GGCUCCGGAGGAGGGUCCCG-3' (sense; SEQ ID NO: 2); siRNA 2: 5'-GGUCUUCUCACACAUCGGCUU-3' (antisense; SEQ ID NO: 3), and 5'-GCCGAUGU-GUGAGAAGACCUU-3' (sense; SEQ ID NO: 4). Others may be readily prepared by those of skill in the art based on the known sequence of the target mRNA. To avoid doubt, the sequence of a human IGF-1R cDNA is provided at GenBank Accession No. NM000875. The Liao & Wang reference also describes the modification of a 2' hydroxyl group on the siRNA with a 2,4-dinitrophenyl (DNP). This modification greatly improves biomembrane permeability and stability of the IGF-1R siRNA molecules, with a corresponding increase in inhibitory potency.

siRNA-mediated reduction in IGF-1R activity is also described, for example, by Qian et al., *Acta Biochim. Biophys. Sin.* (*Shanghai*) 39: 137-147 (2007) (siRNA against IGF-1R inhibited lung metastases in nude mice), and Niu et al., *Cell Biol. Int.* 31: 156-164 (2007), each of which is incorporated herein by reference. Plasmids directing the expression of IGF-1R siRNAs are also commercially available, e.g., from Upstate (Millipore), of Temecula, Calif.

siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human GGT mRNA.

In a preferred embodiment, the siRNA or modified siRNA is delivered to the organ in a pharmaceutically acceptable carrier. Additional carrier agents, such as liposomes, may be added to the pharmaceutically acceptable carrier. Where activity in the lung is desired, delivery can be, for example, by inhalation in a pharmaceutically acceptable carrier for inhalation therapy.

In one embodiment, the RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention.

One method to deliver the siRNAs is catheterization of the blood supply vessel of the target organ.

Other strategies for delivery of the RNA interfering agents, e.g., the siRNAs or shRNAs used in the methods described herein, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. In another embodiment, the siRNA is delivered by delivering a vector encoding small hairpin RNA (shRNA) in a pharmaceutically acceptable carrier to the cells in an organ of an individual. The shRNA is converted by the cells after transcription into siRNA capable of targeting, for example, IGF-1R. In one embodiment, the vector may be a regulatable vector, such as tetracycline inducible vector. In one embodiment, the dsRNA, such as siRNA or shRNA, is delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

The RNA interfering agents, e.g., the siRNAs targeting IGF-1R mRNA, may be delivered singly, or in combination with other RNA interfering agents, e.g., siRNAs, such as, for example siRNAs directed to other cellular genes. IGF-1R siRNAs may also be administered in combination with other pharmaceutical agents which are used to treat or prevent diseases or disorders associated with oxidative stress, especially respiratory diseases, and more especially asthma.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al., *Nature* 411:494-498 (2001); Elbashir, S. M., et al., *Genes & Development* 15:188-200 (2001); Harborth, J. et al., *J. Cell Science* 114:4557-4565 (2001); Masters, J. R. et al., *Proc. Natl. Acad. Sci., USA* 98:8012-8017 (2001); and Tuschl, T. et al., *Genes & Development* 13:3191-3197 (1999)). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al., *Genes Dev.* 16:948-958 (2002); McManus, M. T. et al., *RNA* 8:842-850 (2002); Paul, C. P. et al., *Nat. Biotechnol.* 20:505-508 (2002); Miyagishi, M. et al., *Nat. Biotechnol.* 20:497-500 (2002); Sui, G. et al., *Proc. Natl. Acad. Sci., USA* 99:5515-5520 (2002); Brummelkamp, T. et al., *Cancer Cell* 2:243 (2002); Lee, N. S., et al., *Nat. Biotechnol.* 20:500-505 (2002); Yu, J. Y., et al., *Proc. Natl. Acad. Sci., USA* 99:6047-6052 (2002); Zeng, Y., et al., *Mol. Cell.* 9:1327-1333 (2002); Rubinson, D. A., et al., *Nat. Genet.* 33:401-406 (2003); Stewart, S. A., et al., *RNA* 9:493-501 (2003)). These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence, e.g., an IGF-1R coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (where N can be any nucleotide; SEQ ID NO: 5) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al. (2001) supra and Elbashir et al. 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

Delivery of RNA Interfering Agents: Methods of delivering RNA interfering agents, e.g., an siRNA, or vectors containing an RNA interfering agent, to the target cells, e.g., cells of the lung or other desired target cells, for uptake include injection of a composition containing the RNA interfering agent, e.g., an siRNA, or directly contacting the cell, e.g., a cell of the lung, with a composition comprising an RNA interfering agent, e.g., an siRNA. In another embodiment, RNA interfering agents, e.g., an siRNA may be injected directly into any blood vessel, such as vein, artery, venule or arteriole, via, e.g., hydrodynamic injection or catheterization. Administration may be by a single injection or by two or more injections. The RNA interfering agent is delivered in a pharmaceutically acceptable carrier. One or more RNA interfering agents may be used simultaneously.

In one preferred embodiment, only one siRNA that targets human IGF-1R is used. The delivery or administration of the siRNA is preferably performed in free form, i.e. without the use of vectors. The direct delivery of siRNA to the lung can be performed by inhalation for example, using an electronebulizer.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety may be either in the carboxyl-terminal or amino-terminal end of the construct or in the middle of the fusion protein.

A viral-mediated delivery mechanism can also be employed to deliver siRNAs to cells in vitro and in vivo as described in Xia, H. et al., *Nat Biotechnol* 20(10):1006 (2002)). Plasmid- or viral-mediated delivery mechanisms of shRNA may also be employed to deliver shRNAs to cells in vitro and in vivo as described in Rubinson, D. A., et al., *Nat. Genet.* 33:401-406 (2003)) and Stewart, S. A., et al., *RNA* 9:493-501 (2003)).

The RNA interfering agents, e.g., the siRNAs or shRNAs, can be introduced along with components that perform one or more of the following activities: enhance uptake of the RNA interfering agents, e.g., siRNA, by the cell, e.g., cells of the lung, inhibit annealing of single strands, stabilize single strands, or otherwise facilitate delivery to the target cell and increase inhibition of the target gene, e.g., IGF-1R.

RNA interfering agents, e.g., an siRNA, can also be introduced into cells via topical application to a mucosal membrane or dermally. Vascular or extravascular circulation, the blood or lymph system, and the cerebrospinal fluid are also sites where the agents can be introduced.

The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

Administration/Formulation:

Inhibitors of IGF-1R can be administered to individuals in need thereof in a number of different ways that are well within the abilities of those skilled in the art. Formulations comprising IGF-1R inhibitors will necessarily vary depending upon the mode of administration. In general, the inhibitors will be administered in admixture with a pharmaceutically acceptable carrier or excipient.

Inert, pharmaceutically acceptable carriers or excipients used for preparing pharmaceutical compositions of the IGF-1R inhibitors described herein can be either solid or liquid. Solid preparations include powders, tablets, dispersible granules, capsules, cachets and suppositories. The powders and tablets may comprise from about 5 to about 70% active ingredient. Suitable solid carriers are known in the art, e.g., magnesium carbonate, magnesium stearate, talc, sugar, and/or lactose. Tablets, powders, cachets and capsules can be used as solid dosage forms suitable for oral administration.

Liquid preparations include solutions, suspensions and emulsions. As an example can be mentioned water or water-propylene glycol solutions for parenteral injection. Liquid preparations can also include solutions for intranasal administration. Where direct administration to the lung is desired, aerosol preparations suitable for inhalation are preferred. Aerosol preparations suitable for inhalation can include solutions and solids in powder form, which can be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into conveniently sized molds, allowed to cool and thereby solidify.

The IGF-1R inhibitory agents described herein can also be deliverable transdermally. The transdermal compositions can take the form of creams, lotions, aerosols and/or emulsions and can be included in a transdermal patch of the matrix or reservoir type as are conventional in the art for this purpose.

The suitability of a particular route of administration will depend in part on the pharmaceutical composition (e.g., whether it can be administered orally without decomposing prior to entering the blood stream). Controlled release systems known to those skilled in the art can be used where appropriate.

Preferably the compounds are administered by inhalation, but parenteral or oral administration can be used where appropriate.

Combination of an IGF-1R inhibitor with another therapeutic agent is specifically provided for herein. In a combination therapy, the anti-IGF-1R agent is administered before, during, or after commencing therapy with another agent, as well as any combination thereof, i.e., before and during, before and after, during and after, or before, during and after commencing the combination therapy. Combination agents can include, for example, anti-inflammatories or other agents used for the treatment of fibrotic diseases or disorders.

For example, the IGF-1R inhibitor antibody can be administered between 1 and 30 days, preferably 3 and 20 days, more preferably between 5 and 12 days before commencing combination therapy. In a preferred embodiment of the invention, combination therapy is administered concurrently with or, alternatively, subsequent to IGF-1R inhibitor therapy. Also, in general, the IGF-1R inhibitory agent and the other therapeutic agent do not have to be administered in the same pharmaceutical composition, and may, because of different physical and chemical characteristics, have to be administered by different routes. For example, the IGF-1R inhibitory agent may be administered orally to generate and maintain good blood levels thereof, while the other agent may be administered by inhalation, or vice versa. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In the present invention, any suitable method or route can be used to administer IGF-1R inhibitors, and optionally, to co-administer combination therapeutic agents and/or antagonists of other receptors. Routes of administration include, for example, oral, intravenous, intraperitoneal, subcutaneous, or intramuscular administration. The dose of inhibitor administered depends on numerous factors, including, for example, the type of inhibitor, the type and severity of disease being treated and the route of administration of the inhibitor(s). It should be emphasized, however, that the present invention is not limited to any particular method or route of administration.

One of skill in the art would understand that dosages and frequency of treatment depend on the tolerance of the individual patient and on the pharmacological and pharmacokinetic properties of blocking or inhibitory agent used. Ideally, one wishes to achieve saturable pharmacokinetics for the agent used. A loading dose for an IGF-1R inhibitory agent can range, for example, from about 10 to about 1000 mg/m$^2$, preferably from about 200 to about 400 mg/m$^2$. This can be followed by several additional daily or weekly dosages ranging, for example, from about 200 to about 400 mg/m$^2$. The patient is monitored for side effects and the treatment is stopped when such side effects are severe.

Pharmaceutical compositions described herein can be provided prophylactically or therapeutically to patients having or at risk of having symptoms of acute lung injury or fibrosis. For example, patients having had exposure to a toxic inhalant would likely be treated after such exposure, whereas a patient receiving bleomycin can be treated prophylactically and/or therapeutically. Typically, the compositions of the invention are administered on a daily basis for at least a period of 15 days, although patients with established pulmonary fibrosis, a progressive disease, may receive therapeutic doses for periods of months to years. As used herein, "therapeutic dose" is a dose which prevents, alleviates, abates, or otherwise reduces the severity of symptoms in a patient, e.g., by at least 10% on a clinically accepted scale of disease assessment. Measurement of efficacy is discussed herein below.

Preferably, the pharmaceutical preparation is in unit dosage form. In such form, the preparation is subdivided into unit doses containing appropriate quantities of the active component, e.g., an effective amount to achieve the desired purpose.

The amount and frequency of administration of the IGF-1R inhibitory agent will be regulated according to the judgment of the attending clinician (physician) considering such factors as age, condition and size of the patient as well as severity of the disease being treated. Amounts needed to achieve the desired effect, i.e., a "therapeutically effective dose" will vary with these and other factors known to the ordinarily skilled practitioner, but generally range from 1.0 ng to 5.0 mg, e.g., 100 ng to 2 mg, 1 µg to 2 mg, 10 µg to 2 mg, 100 µg to 2 mg, 500 µg to 2 mg, or another appropriate sub-range, of inhibitory agent per kilogram of body weight, with doses of 0.05 to 2.0 mg/kg/dose being more commonly used. The range depends to a great extent upon the type of inhibitory agent employed. For example, where an agent is expressed from a vector, the amount that must be introduced to the patient will most often be less than, for example, the amount of an antibody or small molecule inhibitor of the receptor. The amounts used will also depend upon the solubility and membrane-permeability of the agent itself or the agent in the given formulation; smaller doses can generally be employed where solubility and permeability are high.

Because pulmonary diseases can often be treated by direct delivery to the affected tissue through aerosol administration, this is a preferred route of administration and will often result in much higher effective doses at the desired location, using a smaller amount of the inhibitory agent, relative to systemic administration, e.g., as by oral or IV routes. As an example, then, appropriate IGF-1R inhibitors can be administered as aerosols at doses ranging, for example, from about 25 g to 25 µg by nebulizer, more often in the range of 250 µg to 750 µg, by nebulizer, for example, three times per week.

Where aerosol administration is to be used, the nebulizer devices require formulation suitable for dispensing the particular type of agent, e.g., protein (such as antibodies), nucleic acid or small molecules. The choice of formulation will depend upon the specific agent used and can be adjusted by the skilled practitioner. However, as an example, where the agent is an antibody or other protein, the agent can be dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Typically, each formulation for aerosol delivery via a nebulizer is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified protein may also be prepared in different formulations depending on the type of chemical modification or the type of device employed.

Formulations for use with a metered-dose inhaler device may generally comprise a finely divided powder containing the protein suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device may comprise a finely divided dry powder containing protein and may also include a bulking agent, such as lactose, sorbitol, sucrose, or mannitol in amounts which facilitate dispersal of the powder from the device, e.g., 50 to 90% by weight of the formulation. Protein agents should most advantageously be prepared in particulate form with an average particle size of less than 10 µm (or microns), most preferably 0.5 to 5 µm, for most effective delivery to the distal lung.

Nasal delivery of protein or other agents is also contemplated. Nasal delivery allows the passage of the protein or other agent to the blood stream directly after administering the therapeutic product to the nose, without the necessity for deposition of the product in the lung. Formulations for nasal delivery include those with dextran or cyclodextran.

For prophylactic or maintenance applications, compositions containing the IGF-1R inhibitory agent can also be administered in similar or slightly lower dosages relative to therapeutic dosages, and often with lower frequency (illustrative examples include, every other day or even weekly or monthly for a maintenance or preventative regimen, as opposed to, for example, every day for a therapeutic regimen).

The frequency and individual amount of dosages for either therapeutic or maintenance/prophylactic uses will also depend, for example, on the in vivo half-life of the IGF-1R inhibitor used. Thus, more frequent dosing is appropriate where the half-life is shorter, and vice versa. One of skill in the art can measure the in vivo half-life for a given IGF-1R inhibitor. Where appropriate, and especially, for example, when the agent will be administered systemically (e.g., intravenously or other systemic route), it is specifically contemplated that IGF-1R inhibitors can be coupled to agents that increase the in vivo half-life of the agent. For example, polypeptides or other agents can be coupled to a serum protein, e.g., serum albumin, to increase the half-life of the polypeptide.

The IGF-1R inhibitory agent or treatment can be administered according to therapeutic protocols well known in the art. It will be apparent to those skilled in the art that the administration of a IGF-1R inhibitory therapy can be varied depending on the disease being treated and the known effects of the agent administered on that disease. Also, in accordance with the knowledge of the skilled clinician, the therapeutic protocols (e.g., dosage amounts and times of administration) can be varied in view of the observed effects of the administered therapeutic agents (e.g., amelioration of symptoms or markers) on the patient, and in view of the observed responses of the disease to the administered therapeutic agents.

Thus, in accordance with experience and knowledge, the practicing physician can modify each protocol for the administration of a component of the treatment according to the individual patient's needs, as the treatment proceeds.

The attending clinician, in judging whether treatment is effective at the dosage administered, can consider the general well-being of the patient as well as more definite signs such as relief of clinically accepted disease-related symptoms.

The present invention is illustrated by the following non-limiting examples. It is to be understood that the particular examples, materials, amounts and procedures are to be interpreted broadly in accord with the scope and spirit of the invention as set forth herein and are not intended to limit the invention in any way. All references described herein, including patents and patent applications as well as literature references, whether published in paper or online versions, are incorporated herein by reference in their entirety.

Efficacy Measurement

The efficacy of treatment can be determined by the skilled clinician. However, a treatment is considered "effective treatment," as the term is used herein, if any one or all of the symptoms, or other clinically accepted symptoms or markers of respiratory disease, acute lung injury and/or fibrosis are ameliorated, e.g., by at least 10% following treatment with an IGF-1R inhibitor. Methods of measuring these indicators are known to those of skill in the art and/or described herein.

Treatment includes any treatment of a disease in an animal and includes:
(1) preventing the disease from occurring in a mammal which may be predisposed to the disease but does not yet experience or display symptoms of the disease; e.g., prevention of the outbreak of the clinical symptoms; (2) inhibiting the disease, e.g., arresting its development; or (3) relieving the disease, e.g., causing regression of the symptoms of the disease. An effective amount for the treatment of a disease means that amount which, when administered to a mammal in need thereof, is sufficient to result in effective treatment as that term is defined herein, for that disease.

Indicators of respiratory disease, acute lung injury and/or fibrosis include functional indicators, e.g., measurement of lung capacity and function, as well as biochemical indicators.

For idiopathic pulmonary fibrosis, for example, improved symptoms include an increase of at least 10% of predicted forced vital capacity (FVC) relative to values prior to treatment. FVC is the total volume of air expired after a full inspiration. Patients with obstructive lung disease usually have a normal or only slightly decreased vital capacity. Patients with restrictive lung disease have a decreased vital capacity.

Another measure is FEV1 (Forced Expiratory Volume in 1 Second). This is the volume of air expired in the first second during maximal expiratory effort. The FEV1 is reduced in both obstructive and restrictive lung disease. The FEV1 is reduced in obstructive lung disease because of increased airway resistance. It is reduced in restrictive lung disease because of the low vital capacity.

A related measure is FEV1/FVC. This is the percentage of the vital capacity which is expired in the first second of maximal expiration. In healthy patients the FEV1/FVC is usually around 70%. In patients with obstructive lung disease FEV1/FVC decreases and can be as low as 20-30% in severe obstructive airway disease. Restrictive disorders have a near normal FEV1/FVC.

Biochemical markers of fibrosis include, for example increased hydroxyproline relative to healthy tissue (e.g., increase by at least 10% relative to healthy tissue), collagen accumulation, increased fibrotic score and cell proliferation.

Where necessary or desired, animal models of lung injury or pulmonary fibrosis can be used to gauge the effectiveness of a given IGF-1R agent. As one example, the bleomycin-induced lung injury model of ALI can be used. Exemplary details for the establishment of ALI in this system are as follows. ICR male mice are anesthetized under pentobarbital (60 mg/kg, i.v.) anesthesia, the cervical region is shaved and the skin is incised for about 4 mm from under the larynx region along the median line. Next, the muscle layer covering upper trachea is peeled off to expose the trachea. Using a micro-syringe, physiological saline or bleomycin hydrochloride (0.03 mg/animal, manufactured by Nippon Kayaku) is administered tracheally (50 μl/animal) from the tracheal smooth muscle region between cricoid cartilage. After the administration, the incised region is closed and antibiotics are administered into the thigh intramuscularly in order to prevent infection. Test agent is administered, e.g., intraperitoneally or via any other acceptable route, following the bleomycin induction. Tests on the physiological saline group (normal group) and bleomycin-induced groups can each be carried out using 10 animals. Fifteen days after the induction, each animal is sacrificed by exsanguination under pentobarbital (60 mg/kg, i.v.) anesthesia, and lung (1 mg) tissue is excised.

Measurement of the lung fibrosis is carried out based on the lung tissue hydroxyproline content as described below. Hydroxyproline content of tissue correlates very well with the degree of fibrosis. The excised lung parenchyma is cut into fine strips of about 2 to 3 mm, transferred into a heat-resistant screw test tube using distilled water (0.4 ml) and then freeze-dried. After overnight freeze-drying, 6 N hydrochloric acid (2.5 ml) is added thereto to carry out hydrolysis at 110° C. for 24 hours. After the hydrolysis, this sample is neutralized with 6 N sodium hydroxide aqueous solution (2.5 ml). Thereafter, this is centrifuged (1,000×g, 5 minutes) and the resulting supernatant (25 μl) is used in the determination of hydroxyproline.

The hydrolyzed supernatant (25 μl) is mixed with borate-alanine buffer (2.475 ml) separately prepared, and potassium chloride (solid) is added thereto until it is saturated. To the mixture, 0.2 M chloramine T (0.6 ml) is added, and incubated at room temperature for 40 minutes for oxidation, and the oxidation is terminated with 3.6 M sodium thiosulfate (2 ml). Toluene (3 ml) is added thereto, followed by sufficiently mixing and heating for 30 minutes in a boiling water bath. Next, the resulting mixture is cooled with tap water, followed by centrifugation (1,000×g, 5 minutes) to separate the toluene layer (1.5 ml). Ehrlich's reagent (0.6 ml) is added thereto to carry out the color development at room temperature for 30 to 40 minutes. The absorbance of each sample is immediately measured at 560 nm, and the amount of hydroxyproline in the sample is calculated from a calibration curve. Other accepted assays for hydroxyproline content can be employed as known in the art.

It is to be understood and expected that variations in the principles of invention herein disclosed may be made by one skilled in the art and it is intended that such modifications are to be included within the scope of the present invention.

The following examples further illustrate the invention, but should not be construed to limit the scope of the invention in any way. Detailed descriptions of conventional methods, such as those employed in the construction of vectors and plasmids, and expression of antibodies and antibody fragments can be obtained from numerous publications, including Sambrook, J et al., (1989) Molecular Cloning: A Laboratory Manual, 2nd ed., Cold Spring Harbor Laboratory Press; Coligan, J. et al. (1994) Current Protocols in Immunology, Wiley & Sons, Incorporated; Enna, S. J. et al. (1991) Current Protocols in Pharmacology, Wiley & Sons, Bonifacino, J. S. et al. (1999) Current Protocols in Cell Biology, Wiley & Sons. All references mentioned herein are incorporated in their entirety.

EXAMPLES

Example 1

Identification of a Role for the IGF Pathway in ARDS

To obtain a more complete protein profile of the airspace milieu in acute respiratory distress syndrome (ARDS) and to identify new mediators, bronchoalveolar lavage fluid (BALF) was analyzed by shotgun proteomics. Using BALF from three patients, a total of 870 different proteins were identified, a nearly 10-fold increase from previous reports. Among the proteins identified were known markers of lung injury, such as surfactant, proteases, and serum proteins. Also identified were several biologically interesting proteins not previously identified in patients with ARDS, including insulin-like growth factor-binding protein-3 (IGFBP-3). Because of the known role of IGFBP-3 in regulating cell survival, IGFBP-3 levels were measured by enzyme-linked immunosorbent assay in ARDS BALF. Normal controls had low levels of IGFBP-3, whereas patients with early ARDS had a significant increase in IGFBP-3. The IGF pathway, acting through the type 1 IGF-receptor (IGF-1R), repressed apoptosis of lung fibroblasts but not lung epithelial cells. Furthermore, depletion of IGF in ARDS BALF led to enhanced fibroblast apoptosis. These data indicate that the IGFBP-3/IGF pathway is involved in the pathogenesis of lung injury.

As a screening strategy to define the bronchoalveolar lavage fluid (BALF) proteome from ARDS patients, "shotgun proteomics" was used, consisting of digestion of proteins in BALF followed by strong-cation exchange fractionation of the peptide mixture and microcapillary-high performance liquid chromatography electrospray ionization tandem mass spectrometry analysis, and then computerized data processing (Griffin T. J., et al., *J Biol Chem* 276:45497-45500 (2001)). Using strict criteria for matching peptide tandem mass spectra to sequences in a database (Keller A., et al., *Anal Chem* 74:5383-5392 (2002); Nesvizhskii A. I., et al., *Anal Chem* 5:4646-4658 (2003)) a total of 897 proteins were identified from three patients, of which 79 were identified in all three patients. Several of the identified proteins were selected for further testing based on their known functions and potential relevance to lung injury. Expression levels of the candidate proteins were analyzed by enzyme-linked immunosorbent assay (ELISA) in a large sample set of ARDS BALF. Notable among the results, insulin-like growth factor (IGF)-binding protein-3 (IGFBP-3) and IGF expression levels correlated with progression of ARDS. Details of the experiments are provided in Examples below.

Example 2

Patient Population

The protocol was approved by the Institutional Review Board, University of Washington. Written informed consent was obtained from the patient or responsible relative before patients were entered into the study. Patients with acute lung injury undergoing bronchoscopy for suspected ventilator-associated pneumonia were included in the study as the initial index patients (Table 1).

TABLE 1

Clinical Characteristics of ARDS Patients

| | Index patients* | | | Retrospective Cohort | | | | | |
|---|---|---|---|---|---|---|---|---|---|
| | 1 | 2 | 3 | At Risk | ARDS summary | Day 1 | Day 3 | Day 7 | Day 14 |
| Age | 28 | 49 | 59 | 47 ± 15 | 43 ± 16 | | | | |
| Risk Factor | | | | | | | | | |
| Sepsis | | | Yes | 3 | 23 | | | | |
| Trauma | Yes | | | 5 | 25 | | | | |
| Other | | Yes | | 0 | 13 | | | | |
| Apache score | 16 | 22 | 20 | 19 ± 8 | 22 ± 7 | 22 ± 6 | 21 ± 9 | 23 ± 8 | 19 ± 3 |
| PaO$_2$/FiO$_2$ | 184 | 271 | 290 | 226 ± 83 | 162 ± 61 | 151 ± 55 | 162 ± 58 | 189 ± 71 | 178 ± 43 |
| Static compliance | nd | nd | nd | 40 ± 10 | 37 ± 13 | 41 ± 15 | 37 ± 19 | 28 ± 9 | 35 ± 17 |
| % BAL volume recovered | 38 | 71 | 33 | 57 ± 11 | 50 ± 14 | 54 ± 12 | 50 ± 15 | 43 ± 11 | 44 ± 19 |
| VAP? | No | Yes | No | | | | | | |

*None of the index patients had a diagnosis of pneumonia as a risk factor for acute lung.

In addition, specimens obtained as part of the University of Washington Specialized Center of Research program in acute lung injury were retroactively analyzed. All patients admitted to the Medical and Surgical Intensive Care Units of Harborview Medical Center between January 1994 and November 1997 were screened prospectively to identify patients who met criteria for predetermined risk criteria for trauma or sepsis "at risk" (Matute-Bello G., et al., *Am J Respir Crit. Care Med* 156:1969-1977 (1997)) or with established ARDS. Matute-Bello G., et al., *Am J Respir Crit. Care Med* 156:1969-1977 (1997); Steinberg K. P., et al., *Am J Respir Crit. Care Med* 150:113-122 (1994); Greene K. E., et al., *Am J Respir Crit. Care Med* 160:1843-1850 (1999)). Patients at risk for ARDS did not meet either radiographical or oxygenation criteria for ARDS. Patients were screened prospectively for the onset of ARDS using the following criteria: 1) PaO$_2$/

FiO$_2$<150 mm Hg or <200 mm Hg on ≧5 cm of H$_2$O positive end-expiratory pressure, 2) diffuse parenchymal infiltrates, 3) pulmonary artery wedge pressure <18 mm Hg or no clinical evidence of congestive heart failure, and 4) no other obvious explanation for these findings. All patients with ARDS met the criteria of the American-European Consensus Conference definition (Bernard G. R., et al., *J Crit. Care* 9:72-81 (1994)). Day 1 was defined as the first 24 hours after meeting the above criteria for ARDS. The clinical characteristics of the patient groups are shown in Table 11 and have been previously described (Matute-Bello et al., supra; Steinberg et al., supra; and Greene et al., supra). As controls, BALF was obtained from six normal volunteers.

Bronchoalveolar lavage (BAL) was performed as previously described (Matute-Bello et al., supra; Steinberg et al., supra; and Greene et al., supra). Briefly, five separate 30-ml aliquots of 0.89% sterile saline were instilled into the right middle lobe or lingula. The BAL recovery averaged 75 ml (49% return) and was not statistically different between the different ARDS groups by one-way analysis of variance (P>0.05). BALF was centrifuged immediately after collection, and cell-free supernatants were aliquoted into polypropylene tubes and stored at −70° C. Total protein measurements were made on aliquots of supernatants using a modified Lowry method (Lowry O., et al., *J Biol Chem* 193: 265-275 (1951)).

Example 3

Peptide Separation and Purification

BALF proteins were concentrated by ice-cold acetone precipitation. BALF containing 2 mg of protein underwent digestion with trypsin (20 µg, sequencing grade; Promega, Madison, Wis.) overnight at 37° C. to allow complete digestion. To prepare for strong-cation exchange chromatography and to reduce the salt concentration, the resulting peptide solutions were diluted eightfold with running buffer (5 mmol/L KH$_2$PO$_4$, 25% acetonitrile, pH 3), and their pH was reduced to ~2.9 with phosphoric acid (H$_3$PO$_4$). The peptide solutions were passed over a 2.1×200 mm, 5-µm particle, 300-Å pore Polysulfoethyl A column (PolyLC; Columbia, Md.), washed with running buffer, and then eluted with a 50-minute biphasic gradient of 0 to 25% elution buffer (running buffer plus 350 mmol/L potassium chloride) in 0 to 30 minutes followed by 25 to 100% elution buffer in 30 to 50 minutes. Flow rate was constant at 0.2 ml/minute. Sixteen 2-minute (0.4-ml) fractions were collected. Fractions from strong-cation exchange chromatography were completely dried down in a Speed-Vac (Thermo-Savant, Milford, Mass.) and redissolved in 0.1% trifluoroacetic acid. To desalt, fractions were loaded onto Oasis mixed-mode cation-exchange cartridges (Waters, Milford, Mass.), washed with 0.1% trifluoroacetic acid, and eluted with 0.1% trifluoroacetic acid, 80% acetonitrile solution. The samples were again dried down and redissolved in 0.2% acetic acid and transferred to autosampler vials for liquid chromatography-tandem mass spectrometry (LC-MS/MS) analysis (Steinberg, et al., *J Endocrinol Invest* 24:856-864 (2001)) Briefly, an LCQ DECA ion trap mass spectrometer (Thermo Finnigan, San Jose, Calif.) outfitted with a microelectrospray source (Brechbuehler, Houston, Tex.) and an HP1100 solvent delivery system (Agilent, Palo Alto, Calif.) was used to analyze the samples. The samples were automatically delivered by a FAMOS autosampler (LC Packings, San Francisco, Calif.) to a 100-µm internal diameter, fused silica capillary precolumn packed with 2 cm of 200-Å pore-size Magic C18AQ material (Michrom Bioresources, Auburn, Calif.) as described elsewhere (Yi E. C., et al., *Rapid Commun Mass Spectrom* 17:2093-2098 (2003)). The samples were washed with solvent A (0.1% formic acid, 5% acetonitrile) on the precolumn and then eluted with a gradient of 10 to 35% solvent B (100% acetonitrile) over 128.5 minutes to a 75-µm×14-cm fused silica capillary column packed with 100-Å pore-size Magic C18AQ material and then into the mass spectrometer at a constant column-tip flow rate of 300 nL/minute. Peptides entering the mass spectrometer were selected for collision induced dissociation by data-dependent methods, and resultant tandem mass spectra were used to obtain protein matches.

Example 4

Protein Identification Strategies

SEQUEST (Link A. J., et al., *Nature Biotechnol* 17:676-682 (1999)) was used to screen tandem mass spectra for matches to peptide sequence by searching against the human International Protein Index database (European Bioinformatics Institute, Cambridge, UK). PeptideProphet and ProteinProphet were used to verify correctness of peptide and protein assignments (Keller A, et al., *Anal Chem* 74:5383-5392 (2002)), respectively, and those that displayed Prophet scores of >0.9 were considered identified. To compare different experiments, data were imported into SBEAMS, a relational database management systems that allows comparison across multiple experiments (Baliga N. S., et al., *Proc Natl Acad Sci USA* 99:14913-14918 (2002)). Gene Ontology classifications were used for functional annotations of described genes (Hosack D. A., et al. *Genome Biol* 4:R70 (2003)).

Example 5

ELISA

Cytokine measurements were performed in duplicate by ELISA using commercially available kits (IGFBP-3 and heparin-binding EGF-like growth factor (HB-EGF) ELISA; R&D Systems, Minneapolis, Minn., and total and free IGF ELISA; Diagnostic Standards Laboratory, Webster, Tex.). Human serum albumin, B2-microglobulin (Alpha Diagnostic International, Inc., San Antonio, Tex.), surfactant-D and Clara cell protein (Biovendor LLC, Candler, N.C.), and fibrinogen (DiaPharma Group, Inc., West Chester, Ohio) were also detected with commercially available ELISA kits.

Concentrations were extrapolated from simultaneously run standard curves. Differences between experimental conditions and normal controls were assessed with the Mann-Whitney Test using VasserStats software. The Spearman rank order correlation coefficient was determined for ELISA concentrations and total protein concentrations (VasserStats). All tests were two-tailed, and P values of <0.05 were considered significant.

Example 6

Western Blot Analysis

To detect proteolytic fragments of IGFBP-3, equal volumes of BALF samples were separated by 15% sodium dodecyl sulfate-polyacrylamide gel electrophoresis, transferred to Immobilon, and blocked for 1 hour. Blots were incubated with polyclonal IGFBP-3 antibody (Diagnostic Standards Laboratory), which recognizes the major proteolytic fragments of IGFBP-3, for 1 hour, followed by peroxidase-conjugated secondary antibody for 1 hour, and then developed with ECL. To quantitate relative band intensities, gels were captured with Photoshop (version 7; Adobe Systems Inc., San Jose, Calif.) and then imported into ImageJ (version 1.30; National Institutes of Health) for analysis (Rasband W S: ImageJ. http://rsb.info.nih.gov/ij/. Bethesda, Md., *US National Institutes of Health*, 1997-2005).

Example 7

Apoptosis Assay

Primary normal human lung fibroblasts (Clonetics, Cambrex Bioscience, Rockland, Me.), primary distal lung human epithelial cells (Clonetics) or A549 (American Type Culture Collection, Manassas, Va.) were seeded in a 96-well tissue culture plate ($2 \times 10^4$ cells/well) overnight and serum-starved for 24 hours. Function blocking antibody to the human type 1 IGF receptor (A12), a generous gift from ImClone Systems (New York, N.Y.) (Burtrum D, et al., *Cancer Res* 63:8912-8921 (2003); Wu J D, et al., *Clin Cancer Res* 11:3065-3074 (2005)), was added to media at indicated concentration for 24 hours. In some experiments, soluble Fas ligand (Alexis Biochemicals, Lausen, Switzerland) or IGFBP-3 (R&D Systems) was added to cells. To assess the contribution of IGF to fibroblast survival in ARDS, BALF was diluted 1:10 with Dulbecco's modified Eagle's medium and then incubated with a neutralizing polyclonal antibody (5 ng/ml) to human IGF-I (R&D Systems) or preimmune goat serum for 30 minutes at 4° C. before incubation with normal human lung fibroblast. After 48 hours, apoptosis was measured. To prevent detached cells from being aspirated, plates were centrifuged at 200×g for 10 minutes, and apoptosis was measured using the Cell Death Detection ELISA-plus System (Roche Applied Science, Penzberg, Germany), which detects cytosolic histone-complexed DNA fragments. All experiments were done in triplicate and repeated at least twice. The data are reported as the mean absorbance of triplicate wells mean+ SE or as apoptosis index, defined as the ratio of the mean absorbance of triplicate wells in the experimental condition $OD_{405\,nm}$/control (media alone) $OD_{405\,nm}$.

Example 8

Identification of Proteins Correlating with ARDS in BALF

BALF samples from three patients with acute lung injury were analyzed by shotgun proteomics, and a total of 870 unique proteins was identified (downloadable data, including spectra and searchable SEQUEST files, are available on the world wide web at peptideadas.org/contributors). The numbers of identifications from individual samples were 226, 291, and 659. Of these, 79 proteins were identified in all three samples (see Supplementary Table 1 at http://address ajp.am-jpathol.org). These identifications represent approximately 10-fold increase in the proteins previously identified in BALF (Noel-Georis I, Bernard A, Falmagne P, Wattiez R: Database of bronchoalveolar lavage fluid proteins. J Chromatogr B Analyt Technol Biomed Life Sci 2002, 771:221-236).

SUPPLEMENTARY TABLE 1

| Gene Name | BALF #1 | BALF #2 | BALF #3 | Molecular Role | Compartment | Protein name |
|---|---|---|---|---|---|---|
| IPI00005160 | 2 | 1 | 3 | Cytoskeleton component | Cellular, cytoskeletal | ARP2/3 complex 41 kda subunit |
| IPI00045658 | 142 | 34 | 166 | Cytoskeleton component | Cellular, cytoskeletal | A-X actin |
| IPI00011116 | 1 | 3 | 4 | Cytoskeleton component | Cellular, cytoskeletal | Ezrin |
| IPI00029600 | 4 | 29 | 5 | Cytoskeleton component | Cellular, cytoskeletal | Moesin |
| IPI00066374 | 2 | 11 | 13 | Cytoskeleton component | Cellular, cytoskeletal | Smooth muscle and non-muscle myosin alkali light chain isoform 4 |
| IPI00021407 | 1 | 12 | 33 | Cytoskeleton component | Cellular, cytoskeletal | Spectrin alpha chain, erythrocyte |
| IPI00170582 | 11 | 6 | 8 | Cytoskeleton component | Cellular, cytoskeletal | Tropomyosin 3 |
| IPI00025283 | 2 | 8 | 1 | Cytoskeleton component | Cellular, cytoskeletal | Tubulin-specific chaperone A |
| IPI00008603 | 18 | 14 | 21 | Cytoskeleton component, motor activity | Cellular, cytoskeletal | Actin, aortic smooth muscle |
| IPI00021439 | 31 | 73 | 50 | Cytoskeleton component, Motor activity | Cellular, cytoskeletal | Actin, cytoplasmic 1 |
| IPI00029823 | 9 | 27 | 58 | Cytoskeleton component, serum response element | Cellular, cytoskeletal | Vimentin |
| IPI00009342 | 1 | 24 | 18 | GTPase inhibitor activity; calmodulin binding | Cellular, cytoskeletal | Ras GTPase-activating-like protein |
| IPI00019502 | 13 | 42 | 24 | Motor activity, actin binding | Cellular, cytoskeletal | Myosin heavy chain, nonmuscle type A |

SUPPLEMENTARY TABLE 1-continued

| Gene Name | BALF #1 | #2 | #3 | Molecular Role | Compartment | Protein name |
|---|---|---|---|---|---|---|
| IPI00010978 | 5 | 28 | 24 | Cytoskeleton component | Cellular, cytoskeletal and membrane | Brain acid soluble protein 1 |
| IPI00018401 | 1 | 1 | 1 | Chaperone activity | Cellular, cytosol | T-complex protein 1, alpha subunit |
| IPI00027749 | 15 | 8 | 7 | Chaperone activity, protein folding | Cellular, cytosol | Heat shock protein HSP 90-beta |
| IPI00102340 | 2 | 19 | 1 | Chaperone activity, protein folding | Cellular, cytosol | Hsp89-alpha-delta-N |
| IPI00033946 | 1 | 7 | 35 | Chaperone activity; protein folding | Cellular, cytosol | Heat shock 70 kda protein 1B |
| IPI00037070 | 1 | 5 | 12 | Chaperone activity; protein folding, ATP binding | Cellular, cytosol | Heat shock 70 kda protein 8 isoform 2 |
| IPI00031523 | 2 | 1 | 1 | Chaperone activity; protein folding, ATP binding | Cellular, cytosol | Heat shock protein 86 (Fragment) |
| IPI00175551 | 3 | 1 | 2 | Cysteine protease inhibitor | Cellular, cytosol | Calpastatin isoform b (calpain) |
| IPI00008399 | 1 | 4 | 3 | Endocytosis | Cellular, cytosol | Breast cancer associated protein BRAP1 |
| IPI00021820 | 1 | 5 | 17 | Fructose metabolism; striated muscle contraction | Cellular, cytosol | Fructose-bisphosphate aldolase A |
| IPI00019755 | 1 | 3 | 5 | Glutathione transferase activity | Cellular, cytosol | Glutathione transferase omega 1 |
| IPI00024093 | 1 | 22 | 1 | Glycolysis | Cellular, cytosol | Glyceraldehyde 3-phosphate dehydrogenase, liver |
| IPI00010379 | 1 | 6 | 1 | Glycolysis | Cellular, cytosol | L-lactate dehydrogenase B chain |
| IPI00018315 | 3 | 29 | 4 | Glycolysis | Cellular, cytosol | Phosphoglycerate kinase 1 |
| IPI00010739 | 2 | 25 | 16 | Glycolysis | Cellular, cytosol | Phosphoglycerate kinase, testis specific |
| IPI00027214 | 8 | 12 | 13 | Glycolysis | Cellular, cytosol | Pyruvate kinase, M1 isozyme |
| IPI00030971 | 1 | 214 | 926 | Oxygen transport | Cellular, cytosol | Beta-globin gene thalassemia patient |
| IPI00005200 | 5 | 531 | 3873 | Oxygen transporter activity | Cellular, cytosol | Hemoglobin alpha chain |
| IPI00023048 | 2 | 6 | 1 | Protein biosynthesis, translation activity | Cellular, cytosol | Elongation factor 1-delta |
| IPI00027444 | 1 | 3 | 1 | Regulates neutrophil elastase activity | Cellular, cytosol | Leukocyte elastase inhibitor |
| IPI00003815 | 5 | 19 | 8 | Rho GDP-dissociation inhibitor activity; GTPase activator activity | Cellular, cytosol | Rho GDP-dissociation inhibitor 1 |
| IPI00021070 | 1 | 3 | 2 | Superoxide metabolism; cellular defense response | Cellular, cytosol | Neutrophil cytosol factor 2 |

SUPPLEMENTARY TABLE 1-continued

| Gene Name | BALF #1 | #2 | #3 | Molecular Role | Compartment | Protein name |
|---|---|---|---|---|---|---|
| IPI00013348 | 3 | 32 | 18 | Transferase activity | Cellular, cytosol | Glutathione S-transferase P |
| IPI00027223 | 4 | 8 | 3 | Carbohydrate metabolism | Cellular, cytosol, peroxisome | Isocitrate dehydrogenase [NADP] cytoplasmic |
| IPI00003817 | 2 | 54 | 110 | Rho GDP-dissociation inhibitor activity; GTPase activator | Cellular, cytosolic vesicle | Rho GDP-dissociation inhibitor 2 |
| IPI00010796 | 2 | 13 | 3 | Protein disulfide isomerase activity | Cellular, endoplasmic reticulum | Protein disulfide isomerase precursor |
| IPI00006699 | 46 | 28 | 7 | Rhodopsin-like, G-protein coupled receptor protein signaling; molecular function unknown | Cellular, integral to membrane | Proline-rich protein G1 |
| IPI00004573 | 116 | 64 | 8 | Binds to Ig, protein transporter | Cellular, integral to membrane, also secreted | Polymeric-immunoglobulin receptor precursor |
| IPI00170645 | 6 | 2 | 2 | DNA binding | Cellular, nuclear | H2A histone family, member Q |
| IPI00173442 | 1 | 2 | 5 | DNA binding | Cellular, nuclear | HMG-1 |
| IPI00026156 | 1 | 4 | 1 | DNA binding, transcription factor activity | Cellular, nuclear | Hematopoietic lineage cell specific protein |
| IPI100031812 | 1 | 3 | 3 | DNA binding, transcription regulation | Cellular, nuclear | Nuclease sensitive element binding protein 1 |
| IPI100020463 | 1 | 6 | 10 | Nucleosome formation | Cellular, nuclear | Histone H4 |
| IPI00164312 | 13 | 26 | 70 | Forms membrane channels, binds to phospholipids | Cellular, plasma membrane | Annexin I |
| IPI00011251 | 13 | 5 | 41 | Forms membrane channels, binds to phospholipids | Cellular, plasma membrane | Annexin II |
| IPI00032194 | 20 | 6 | 4 | Acute phase reactant | Extracellular | Inter-alpha-trypsin inhibitor heavy chain H4 precursor |
| IPI00022431 | 98 | 2 | 74 | Acute-phase reactant; regulation of inflammatory response | Extracellular | Alpha-2-HS-glycoprotein precursor |
| IPI00103264 | 17 | 9 | 1 | Blood coagulation | Extracellular | Similar to fibrinogen, A alpha polypeptide |
| IPI00022393 | 1 | 1 | 7 | Complement pathway | Extracellular | Complement C1q subcomponent, B chain precursor |
| IPI00022395 | 3 | 3 | 1 | Complement pathway | Extracellular | Complement component C9 precursor |
| IPI00017601 | 3 | 27 | 10 | Copper ion homeostasis | Extracellular | Ceruloplasmin precursor |
| IPI00032180 | 11 | 10 | 209 | Endopeptidase inhibitor activity | Extracellular | Alpha-1-antitrypsin precursor |
| IPI00021002 | 2 | 3 | 12 | Endopeptidase inhibitor activity | Extracellular | Inter-alpha-trypsin inhibitor heavy chain H2 precursor |
| IPI00028413 | 2 | 2 | 1 | Endopeptidase inhibitor activity | Extracellular | Inter-alpha-trypsin inhibitor heavy chain H3 precursor |
| IPI00027265 | 5 | 5 | 6 | Endoproteinase inhibitor | Extracellular | Complement component 4A preproprotein |

SUPPLEMENTARY TABLE 1-continued

| Gene Name | BALF #1 | BALF #2 | BALF #3 | Molecular Role | Compartment | Protein name |
| --- | --- | --- | --- | --- | --- | --- |
| IPI00032714 | 1 | 2 | 2 | Inhibit thiol protease, coagulation, mediator of inflammation | Extracellular | Kininogen |
| IPI00021841 | 40 | 7 | 73 | Lipid transport | Extracellular | Apolipoprotein A-I precursor |
| IPI00155752 | 2 | 7 | 1 | Matrix protein | Extracellular | Fibronectin 1 isoform 1 preproprotein |
| IPI00004656 | 1 | 7 | 13 | MHC class I receptor activity, antigen presentation | Extracellular | Beta-2-microglobulin precursor |
| IPI00027019 | 4 | 2 | 9 | Salivary glands, lacrimal glands expression | Extracellular | Proline-rich protein 4 precursor |
| IPI00022434 | 23 | 1 | 79 | Transporter activity; carrier activity; drug binding | Extracellular | Serum albumin precursor |
| IPI00026314 | 4 | 36 | 92 | Actin binding, calcium ion binding | Extracellular, cytoskeleton | Gelsolin precursor, plasma |
| IPI00021842 | 123 | 4 | 1 | Response to reactive oxygen species; lipid transport; induction of apoptosis | Extracellular, cytosol | Apolipoprotein E precursor |
| IPI00021885 | 196 | 43 | 113 | Blood coagulation | Extracellular, fibrinogen complex; soluble fraction | Fibrinogen alpha/alpha-E chain precursor [Contains: Fibrinopeptide A] |
| IPI00021886 | 2 | 5 | 2 | Blood coagulation | Extracellular, fibrinogen complex; soluble fraction | Fibrinogen beta chain precursor [Contains: Fibrinopeptide B] |
| IPI00034271 | 24 | 46 | 4 | Blood coagulation | Extracellular, fibrinogen complex; soluble fraction | fibrinogen, gamma chain, isoform gamma-A precursor |
| IPI00032215 | 3 | 29 | 61 | Acute-phase reactant, inflammatory response, endopeptidase inhibitor activity | Extracellular, intracellular | Alpha-1-antichymotrypsin precursor |
| IPI00023590 | 26 | 15 | 2 | Complement pathway, apoptosis regulator, apo J | Extracellular, secreted | Clusterin precursor |
| IPI00022368 | 58 | 10 | 1 | Acute-phase responseg-protein-coupled receptor binding; lipid transporter activity | Extracellular, serum | Serum amyloid A protein precursor |
| IPI00006146 | 11 | 1 | 4 | Major acute phase reactant. Apolipoprotein of the HDL complex | Extracellular, serum | Serum amyloid A2 |

SUPPLEMENTARY TABLE 1-continued

| Gene Name | BALF #1 | #2 | #3 | Molecular Role | Compartment | Protein name |
|---|---|---|---|---|---|---|
| IPI00003269 | 1 | 1 | 6 | | | ENSP00000306469 Tax_Id = 9606 |
| IPI00164623 | 117 | 38 | 291 | | | ENSP00000245907 Tax_Id = 9606 |
| IPI00174551 | 5 | 1 | 66 | | | ENSP00000285545 Tax_Id = 9606 |
| IPI00164479 | 25 | 10 | 5 | | | ENSP00000310597 Tax_Id = 9606 |
| IPI00103265 | 38 | 38 | 106 | | | Hypothetical protein |
| IPI00152853 | 1 | 1 | 1 | | | Hypothetical protein KIAA1949 (Fragment) |

This approach identified similar classes of proteins to those previously reported using two-dimensional electrophoresis (2DE) (Noel-Georis I., et al., *J Chromatogr B Analyt Technol Biomed Life Sci* 771:221-236 (2002)). Of the 79 proteins common to all three patients, proteins from all cellular compartments were identified, including membrane proteins, cytosolic proteins, nuclear proteins, and cytoskeletal proteins, as well as extracellular and secreted proteins. As expected, albumin was identified in all three samples (Hirsch J., et al., *Am J Physiol* 287:L1-L23 (2004)). However, the number of peptides corresponding to albumin varied widely in the patients ranging from 1 to 23 to 79, suggesting that the degree of serum protein leakage varied widely even among these three patients with clinically diagnosed ARDS. Extensive coverage of other abundant serum proteins was also found, such as ceruloplasmin (average number of peptides: 13) and fibrinogen αchain (average number of peptides: 117), and other acute phase reactant proteins, such as α1 chymotrypsin (average number of peptides: 31), α2-HS-glycoprotein (average number of peptides: 58), and anti-trypsin inhibitor (average number of peptides: 77). A number of intracellular proteins were also identified, as has been previously reported in lung BAL (Noel-Georis I., et al., *J Chromatogr B Analyt Technol Biomed Life Sci* 771:221-236 (2002)), presumably due to increased cellular turnover and death in lung compartment during lung injury. The presence of several serum proteins (albumin, fibrinogen, and B2-microglobulin) and pulmonary proteins (surfactant D and Clara cell protein) was confirmed by ELISA. Surfactant A2 was also identified, as previously reported by 2DE (Noel-Georis I., et al., *J Chromatogr B Analyt Technol Biomed Life Sci* 771:221-236 (2002); Bowler R. P., et al., *Am J Physiol* 286:L1095-L1104 (2004)). In addition, surfactant B2 (two patients) and surfactant D (one patient) were also identified here but were not found in previous 2DE analysis of BALF. Previous reports speculated that 2DE failed to identify surfactant B2, because of its hydrophobicity, and surfactant D, because of its relative underexpression compared to surfactant A2.

From the long list of proteins identified by LC-MS/MS shotgun proteomics, it was decided to focus on secreted proteins, because they may represent mediators of lung injury. This category included identifications of pre-B-cell colony-enhancing factor in two patients, HB-EGF in one patient and IGFBP-3 and the acid labile subunit (ALS) in two patients, both components of the IGF signaling complex. Pre-B-cell colony-enhancing factor was recently described as an inhibitor of apoptosis that was expressed by neutrophils from septic patients (Jia S. H., et al., *J Clin Invest* 113:1318-1327 (2004)). Previous reports showed elevated levels of IGFBP-3 in BALF from patients with idiopathic pulmonary fibrosis (IPF) (Aston C., et al., *Am J Respir Crit. Care Med* 151:1597-1603 (1995); Pala L., et al., *J Endocrinol Invest* 24:856-864 (2001)) and sarcoidosis (Allen J. T., et al., *Am J Respir Cell Mol Biol* 19:250-258 (1998)). In contrast, HB-EGF has not been previously associated with acute lung injury.

Example 9

Validation of Changes in Secreted Proteins in a Large ARDS BALF Sample Set

Proteomics results do not distinguish between reproducible changes and sampling variability during the comparison of data from three different patients. To assess the potential significance of secreted BALF proteins identified by LC-MS/MS shotgun proteomics, expression levels of HB-EGF, IGFBP-3, and IGF-I were measured by ELISA in a large BALF sample set that includes patients at different time points in ARDS progression. BALF samples from normal subjects (n=6), patients at risk for development of ARDS (n=8), and established ARDS at day 1 (n=26), day 3 (n=20), day 7 (n=10), and day 14 (n=5) were analyzed.

HB-EGF is a potent mitogen and chemotactic factor for fibroblasts (Raab G., et al., *Biochim Biophys Acta* 1333:F179-F199 (1997)). Thus, it was hypothesized that it might play a role in the fibroproliferative response during acute lung injury. However, ELISA results revealed very low levels of HB-EGF in ARDS BALF and in normal BALF. Furthermore, a correlation between HB-EGF levels and progression of lung injury was not observed in ARDS. Failure to detect changes in HB-EGF levels in ARDS BALF does not necessarily preclude a role for HB-EGF in lung injury. For instance lack of correlation by ELISA may be due to complex tissue distribution of the multiple forms of HB-EGF (Iwamoto R., et al., *Cytokine Growth Factor Rev* 11:335-344 (2000)) making it inaccessible in BALF. However, these data illustrate the importance of independently verifying proteins identified by any proteomic screen.

IGFBP-3 is also a potential candidate protein relevant to the pathogenesis of ARDS. While very low levels of IGFBP-3 were found in BALF from normal controls by ELISA, a marked increase in IGFBP-3 concentration was detected in patients at risk for ARDS and in those with established ARDS. Because earlier work demonstrated elevated levels of IGFBP-3 in BALF from patients with IPF and sarcoidosis (Pala L., et al., *J Endocrinol Invest* 24:856-864 (2001); Allen J. T., et al., *Am J Respir Cell Mol Biol* 19:250-258 (1998)), it was initially speculated that IGFBP-3 would be elevated in late ARDS (day 7 onward), when fibroblast proliferation is a prominent histological feature. Surprisingly, the highest levels were found early in ARDS (days 1 and 3), with levels decreasing as the disease progressed. This is supported by recent evidence that fibroblast activation occurs early in disease (Olman M. A., et al., *J Immunol* 172:2668-2677 (2004)).

Proteolysis of IGFBP-3 decreases its ability to bind IGF, thereby increasing the bioavailability of the ligand (Clemmons D. R., *Cytokine Growth Factor Rev* 8:45-62 (1997)). In addition, proteolytic fragments can have independent biological activity (Lalou C., et al., *Endocrinology* 137:3206-3212 (1996)). However, the IGFBP-3 ELISA does not discriminate between full-length IGFBP-3 and proteolytic fragments. To evaluate the proteolysis of IGFBP-3, day 1 and day 3 BALF were analyzed by Western analysis using an antibody that recognizes the major proteolytic fragments. The proportion of intact IGFBP-3 to total IGFBP-3 immunoreactivity was determined by densitometry. In at-risk and ARDS day 1 BALF, the majority of IGFBP-3 was present as the intact 41- and 44-kd doublet (at-risk: 53%±13; ARDS day 1: 66%±14, respectively); the 30-kd fragment was the major proteolytic fragment observed in the samples. Thus, the majority of IGFBP-3 is intact at the time in which concentrations are the highest.

Figure 1B:
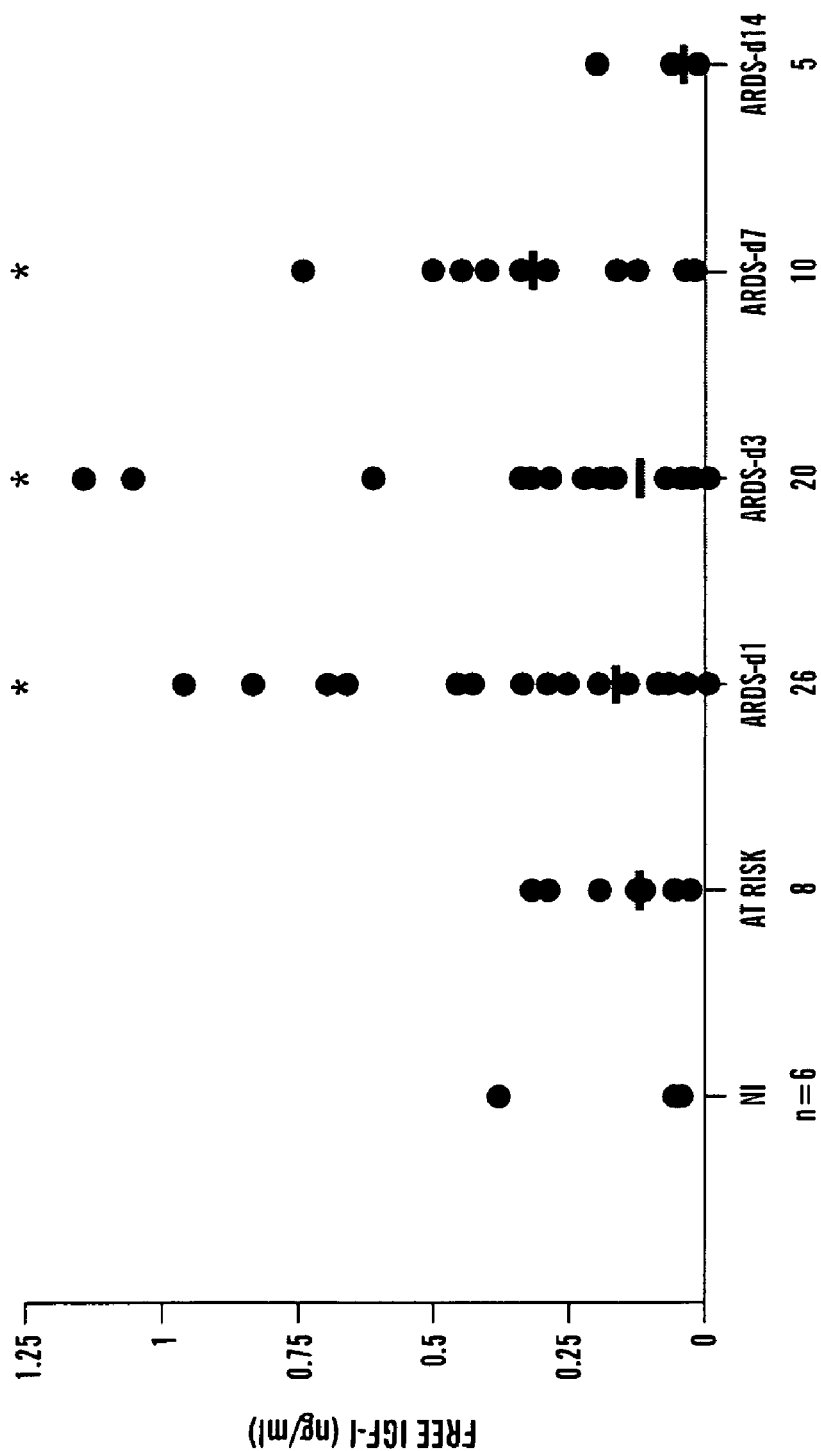

IGFBP-3 is the major binding protein of IGF-I and is bound in a 1:1:1 molar ratio with IGF and the ALS. Although we did not detect IGF in LC-MS/MS proteomics analysis, failure to identify a protein from complex peptide mixtures such as BALF by this screening method does not necessarily indicate absence of the protein (Yi E. C., et al., *Electrophoresis* 23:3205-3216 (2002)). However, IGF was subsequently detected in the three index samples by ELISA (free IGF: 0.1, 0.05, and 0.04 ng/ml). In addition, ALS was detected by LC-MS/MS, adding further evidence for a role for the IGF/IGFBP-3 axis in lung injury. Because the ratio of IGF to IGFBP-3 is an important factor in regulating the bioactivity of IGF-I in BALF, total IGF protein levels were assessed by ELISA. The levels of IGF were similar to those observed for IGFBP-3; i.e., low levels in normal controls, increased in at-risk and early ARDS patients (day 1 and day 3), and decreased levels in late ARDS patients (FIG. 1A). Because bioactivity of IGF is determined by the unbound or free IGF, free IGF-I was also measured in BALF (FIG. 1B). As expected, the levels of free IGF were significantly lower than total IGF. Interestingly, the free levels of IGF were elevated later in disease than total IGF. This may be due to changes in other members of the IGFBP family. While it is possible that changes in expression levels simply reflect changes in capillary permeability and serum exudation, this is less likely for several reasons. First, it was found that the majority of change in IGFBP-3 levels could not be accounted for by changes in BALF total protein, with only a fair correlation ($r^2$=0.39). Furthermore, there was no correlation between total or free IGF and total protein ($r^2$=0.04 and 0.5, respectively, P>0.05). In addition, measurements of other cytokines and growth factors from the same BALF samples show distinct patterns of expression (Goodman R. B., et al., *Am J Respir Crit. Care Med* 154:602-611 (1996); Park W. Y., et al., *Am J Respir Crit. Care Med* 164:1896-1903 (2001)).

Example 10

Figure 2A:
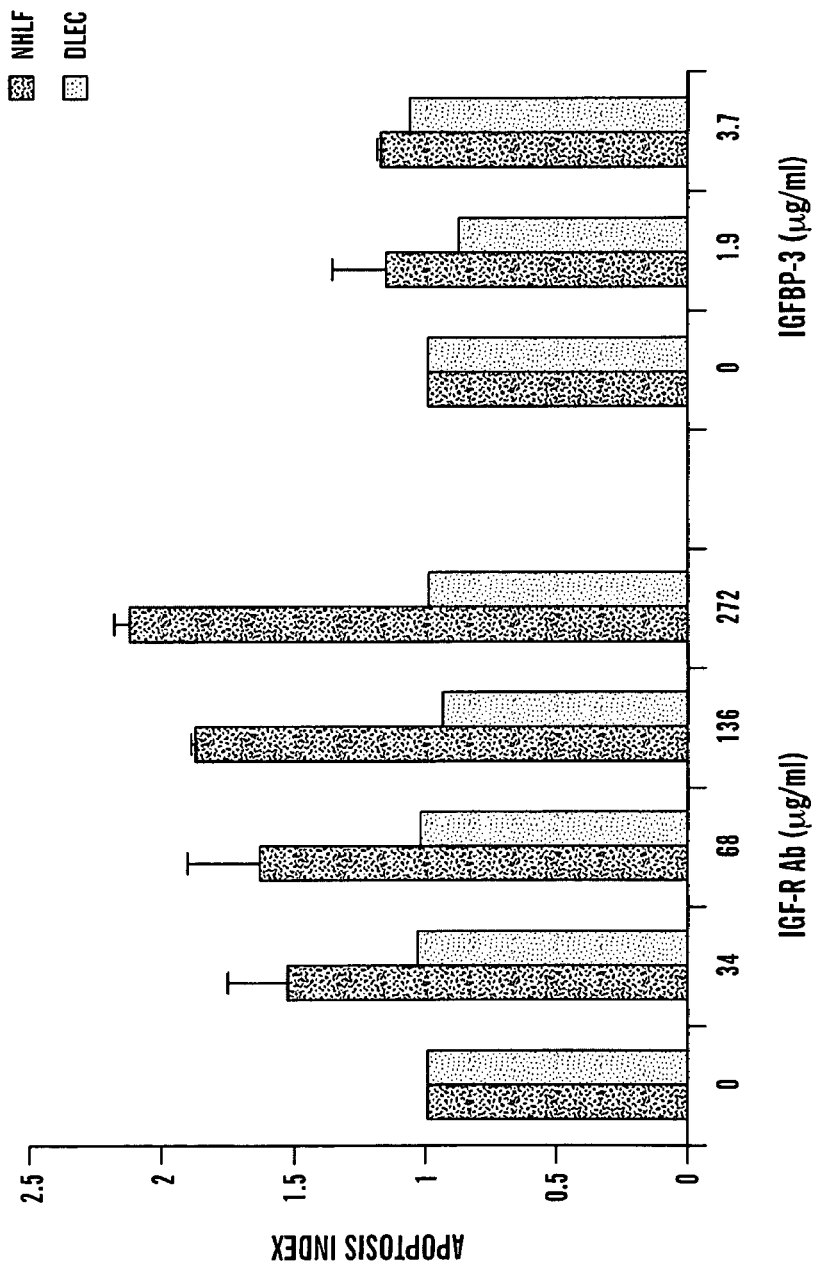
FIG. 2 shows increased apoptosis of primary normal human lung fibroblasts treated with IGF-1R antibody. A: Normal human lung fibroblast or distal lung epithelial cells were serum-starved overnight and then incubated with indicated concentration of IGF-1R antibody or IGFBP-3 overnight. B: A549 cells were serum-starved and incubated with IGF-1R antibody (136 µg/ml) with or without the indicated concentration of Fas ligand. Apoptosis was measured by Cell Death ELISA-plus ELISA (Roche Applied Science) per the manufacturer's directions. All experiments were done in triplicate and repeated at least twice. Apoptosis index is defined as the ratio of experimental condition $OD_{405\,nm}$: control (media alone) $OD_{405\,nm}$.
Figure 2B:
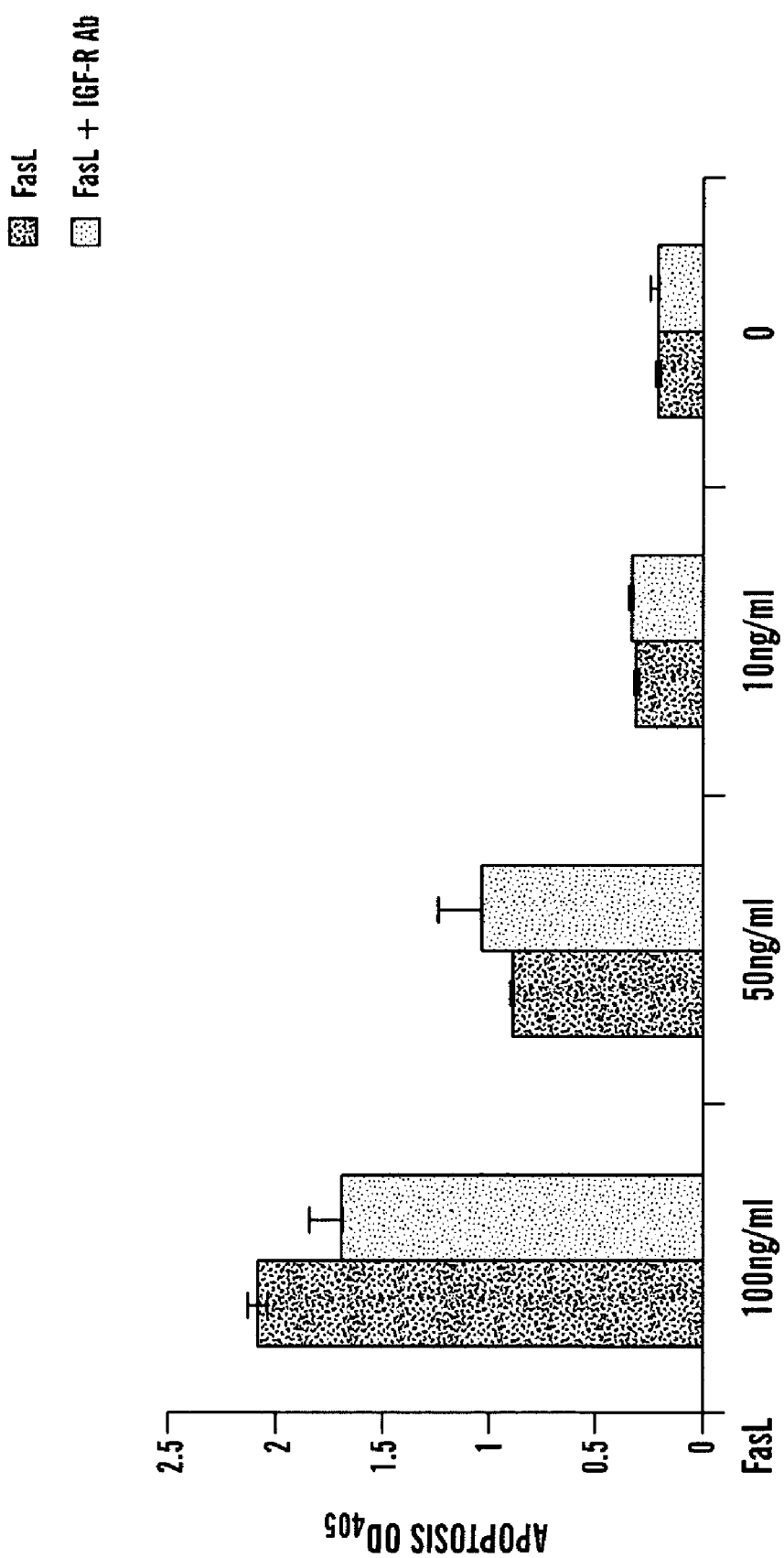

IGF/IGF-I Receptor Pathway Regulates Lung Fibroblast but Not Epithelial Cell Apoptosis Apoptosis in the lung plays an important role in the development and resolution of acute lung injury. Initial epithelial damage and apoptosis occurs early in ARDS. At the same time, fibroblast activation is thought to occur (Olman M. A., et al., *J Immunol* 172:2668-2677 (2004); Chesnutt A. N., et al., *Am J Respir Crit. Care Med* 156:840-845 (1997)), setting the stage for the later fibroproliferative phase of ARDS. In addition, apoptosis of connective tissue cells, such as fibroblasts, may be necessary for injury to resolve. Elevated levels of IGFBP-3 and IGF-I were found in at-risk patients and those with early ARDS, when epithelial damage and death occur. Addition of a blocking antibody to the type 1 IGF receptor (IGF-1R) induced a dose-dependent increase in apoptosis of primary human lung fibroblasts but not primary lung epithelial cells or the human macrophage cell line THP-1 under conditions of serum starvation (FIG. 2A and data not shown). Because the Fas pathway is an important contributor to epithelial cell apoptosis in ARDS BALF (Matute-Bello G., et al., *J Immunol* 163:2217-2225 (1999)), it was asked whether the IGF pathway might influence Fas-mediated apoptosis. However, treatment with IGF-1R antibody did not alter Fas-induced apoptosis of epithelial cells or fibroblasts (FIG. 2B and data not shown). Because IGFBP-3 can signal independently of IGF-1R (Lalou C., et al., *Endocrinology* 137:3206-3212 (1996); Franklin S. L., et al., *J Clin Endocrinol Metab* 88:900-907 (2003)), the effect of IGFBP-3 on fibroblast and epithelial cell apoptosis was also examined. In contrast to reports showing that IGFBP-3 induced apoptosis in certain cells (Shim M. L., et al., *Growth Horm IGF Res* 14:216-225 (2004)), increased apoptosis was not observed in fibroblasts or epithelial cells treated with increasing doses of IGFBP-3 (FIG. 2). Together, these data indicate that IGF acts through IGF-1R selectively to promote fibroblast survival, with the potential to modify matrix remodeling and repair in acute lung injury.

Figure 3A:
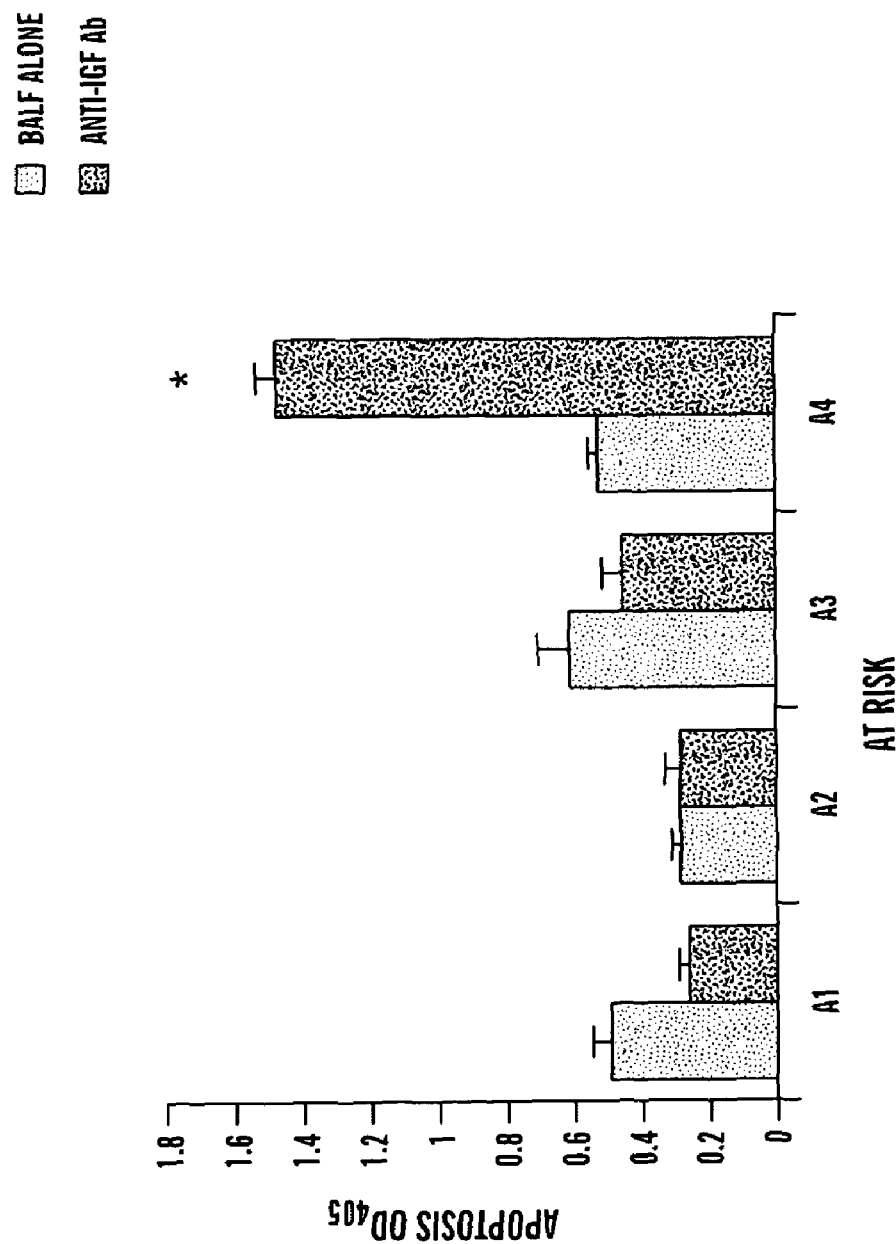
FIG. 3 shows that IGF mediates a fibroblast prosurvival signal in ARDS BALF. Fibroblast apoptosis was measured 48 hours following incubation of normal human lung fibroblast with BALF with or without IGF neutralizing antibody (5 ng/ml) from at-risk patients (A) or ARDS patients (B). Apoptosis was measured by Cell Death ELISA-plus ELISA (Roche Applied Science) per the manufacturer's directions. All experiments were done in triplicate and repeated at least twice. Data are reported as the mean $OD_{415\,nm}$±SD. *Significant difference ($P<0.05$) from BALF alone.
Figure 3B:
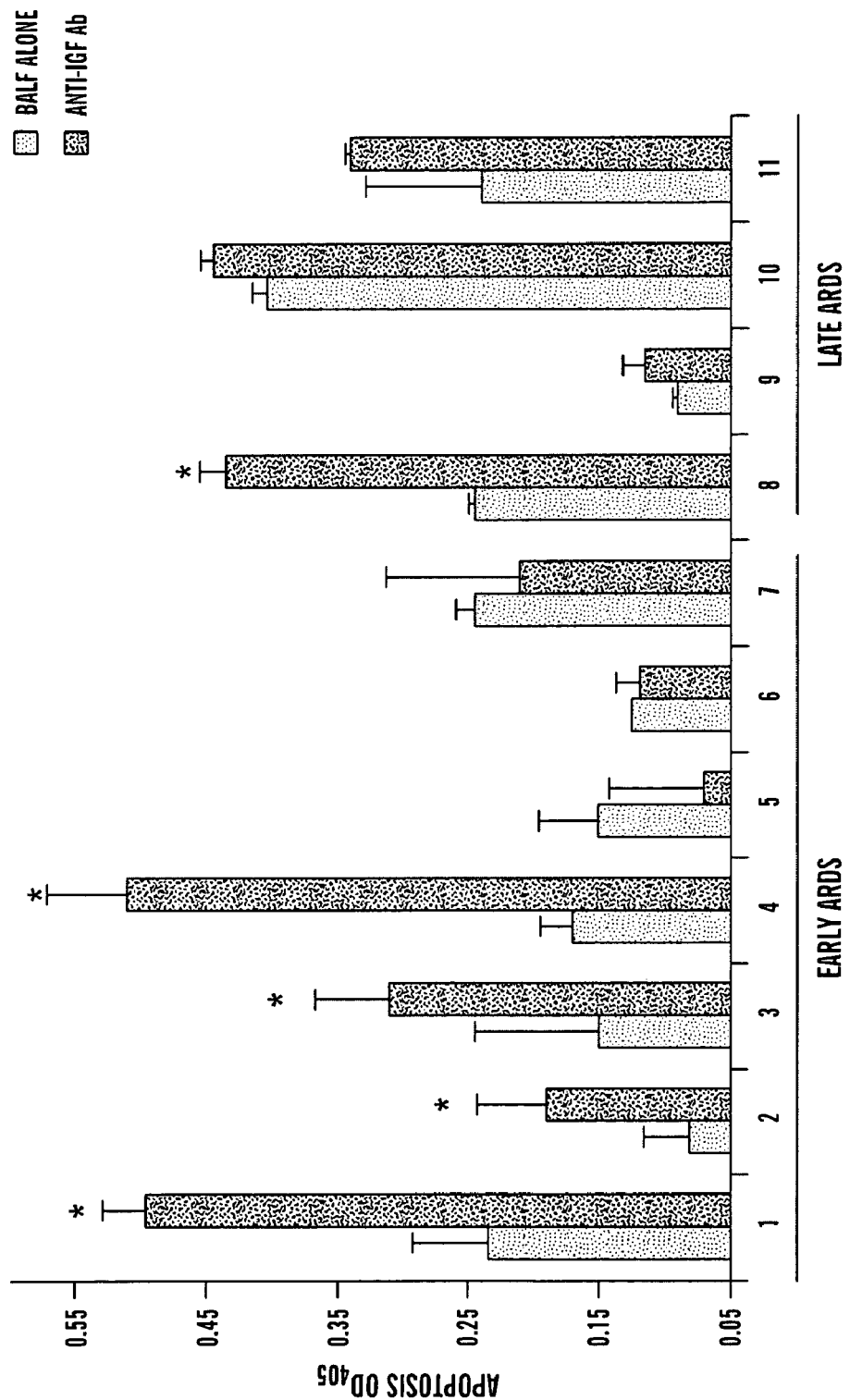

Finally, to determine directly the contribution of the IGF pathway to fibroblast survival during ARDS, fibroblast apoptosis was examined following incubation with ARDS BALF pretreated with a neutralizing antibody to IGF or with preimmune serum (FIG. 3). In BALF from early ARDS (<7 days), four of seven samples showed a significant increase in fibroblast apoptosis following IGF neutralization. In BALF from late ARDS (>7 days), one of four samples showed a significant increase in fibroblast apoptosis following IGF neutralization. In BALF from at-risk patients, one of four samples showed a significant increase in fibroblast apoptosis following IGF neutralization (FIG. 3A). Thus, the data indicate that in vivo concentrations of IGF contribute to fibroblast survival during many cases of acute lung injury, particularly in early ARDS.

Protein Database of BALF

Using shotgun proteomics the largest set of BALF proteins was identified in acute lung injury patients to date. The majority of proteins previously reported from 2DE analysis of BALF from patients with interstitial lung disease and acute lung injury (Noel-Georis I., et al., *J Chromatogr B Analyt Technol Biomed Life Sci* 771:221-236 (2002); Bowler R. P., et al., *Am J Physiol* 286:L1095-L1104 (2002)) were also identified in this study by tandem mass spectrometric analysis. Expected markers of lung injury were among those identified such as surfactants A and B, markers of activation and inflammation such as C3a, leukotrienes and markers of matrix remodeling, including collagenases A and B, and proteases. Not surprisingly, many of the proteins identified in BALF from ARDS patients were serum proteins, consistent with the capillary leak syndrome that is characteristic of ARDS.

While even this study underestimates the true protein content of BALF, the number of proteins identified in this study is an order of magnitude greater than previously published reports. Furthermore, proteins in the IGF signaling pathway as well as other secreted proteins were identified that can contribute to disease process. This approach permitted the identification of a new pathway in ARDS and subsequently showed changes in expression using a large sample set of ARDS BALF. Bronchoalveolar lavage is a safe method to obtain lung epithelial lining fluid of the airways and alveoli (Steinberg K. P., et al., *Am J Respir Crit. Care Med* 150:113-122 (1994)). Initial reports of proteomic analysis of normal BALF separated proteins by 2DE, which is based on differences of charge and mass, followed by enzymatic degradation of separated proteins and analysis by mass spectrometry. The initial report of BALF proteomic analysis identified 23 serum proteins in normal BALF, representing 97% of the identified proteins in BALF (Bell D. Y., et al., *Am Rev Respir Dis* 119:979-990 (1979)). As the 2DE methodology has improved, the number of proteins identified has increased. A recently published 2DE database of BALF proteins from normal and lung disorders contained 93 proteins (Noel-Georis I., et al., *J Chromatogr B Analyt Technol Biomed Life Sci* 771:221-236 (2002)). However, several aspects of the 2DE method limit the ability to detect particular classes of proteins (Gygi S. P., et al., *Proc Natl Acad Sci USA* 97:9390-9395 (2000)). For example, while the most "abundant" proteins can be readily detected in ARDS BALF by 2DE and MS, low abundance proteins are often not detected without prior fractionation. For these studies, it was elected to avoid prior sample fractionation because of the loss of proteins involved and the limited amount of protein present in the clinical ARDS BALF samples. Therefore, it was chosen to use cation exchange chromatography of trypsin-digested samples followed by MS/MS analysis to define the ARDS BALF proteome. While this method also has limitations (23), namely the random selection of ions as they enter the tandem mass spectrometer that results in poor overlap in the proteins identified in replicate analyses, it is has the advantage of speed and ease. Because a primary LC-MS/MS proteomic screen is unable to sample all of the proteins present (Yi E. C., et al., *Electrophoresis* 23:3205-3216 (2002)), additional methods, including isolation of subpopulations of proteins and further refinement of the methodologies, should increased yield of protein identifications. In addition, one can estimate relative abundance by comparing sequence coverage and number of peptides identified (Liu H., et al., *Anal Chem* 76:4193-4201 (2004)). Therefore, LC-MS/MS analysis is an excellent screening tool to initially characterize a sample of mostly unknown protein composition, but this must be followed by corroboration of interesting results using independent methods.

Example 11

Role of the IGF/IGFBP-3 Pathway

Following initial LC-MS/MS proteomic analysis of BALF, studies described herein were focused on further characterization of IGF pathway components. Because of the known role of the IGF pathway in regulation of cell survival (LeRoith D., et al., *Cancer Lett* 195:127-137 (2003); Clemmons D. R., *Cytokine Growth Factor Rev* 8:45-62 (1997)), it was tested whether this pathway might play a role in the development and resolution of acute lung injury. IGF-binding proteins are a family of six related proteins that bind IGF-I and -II with high affinity. IGFBP-3, the major circulating IGFBP, binds IGF-I in conjunction with an acid-labile glycoprotein subunit (ALS) to form a circulating complex. Because of the high affinity of IGFBP-3 for IGF-I, it has a major role in controlling the bioavailability of IGFs. IGF-I bound to IGFBP-3 does not interact with IGF-1R and thus fails to induce a prosurvival signal. IGF-I bound to IGFBP-3 has a longer half-life and may act as a stable reservoir of IGF-I. It was found that the concentrations of IGFBP-3 and IGF were highest in at risk and early ARDS, and then decreased as disease progressed. IGFBP-3 is subject to cleavage by a number of proteases, including plasmin, matrix metalloproteases, and cathepsins. Because IGFBP-3 fragments have lower affinity for IGF than does the intact binding protein, proteolysis of IGFBP-3 is the major mechanism for release of IGF and increasing IGF bioavailability. Increased IGFBP-3 proteolysis was observed in BALF from other lung diseases. For example, BALF from sarcoid patients contained elevated IGFBP-3, most in the form of 30-kd (proteolyzed) fragment (Allen J. T., et al., *Am J Respir Cell Mol Biol* 19:250-258 (1998)). However, it was found in the studies described herein that the majority of IGFBP-3 was intact, not proteolyzed, despite the presumed proteolytic environment during ARDS.

Results from in vitro studies described herein showed that the IGF pathway regulates survival of fibroblasts, not epithelial cells. In addition, neutralization of IGF in ARDS BALF increased fibroblast apoptosis. This was most pronounced in early ARDS. This indicates that IGF detected in BALF is biologically active and can play a role in regulating fibroblast survival in ARDS. The lack of effect of IGF neutralization in some samples may be due to additional pathways that regulate fibroblast survival. For example, interleukin-1β in lung edema fluid induces fibroblast proliferation (Olman M. A., et al., *J Immunol* 172:2668-2677 (2004)). In addition, surfactant A (Vazquez de, Lara L, et al., *Am J Physiol* 279:L950-L957 (2000)) and fibronectin-derived peptides (Hadden H. L., et al., *Am J Respir Crit. Care Med* 162:1553-1560 (2000) also affect fibroblast apoptosis. While histological evidence of fibroproliferation is observed 5 to 7 days after the onset of ARDS, there is increasing evidence that fibroblasts are activated very early in ARDS. For example, procollagen III peptide, a marker of collagen synthesis, is elevated in BALF early in ARDS and remains elevated for 7 days or longer (Chesnutt A. N., et al., *Am J Respir Crit. Care Med* 156:840-845 (1997); Clark J. G., et al., *Ann Intern Med* 122:17-23 (1995)). Pulmonary edema fluid obtained from acute lung injury patients within 4 hours of intubation has an increased mitogenic effect on human lung fibroblasts (Olman M. A., et al., *J Immunol* 172:2668-2677 (2004)). In concert, the data indicate that fibroblast activation is already occurring at the time acute lung injury is clinically apparent. Because IGF is elevated early in ARDS and regulates fibroblast survival, the IGF pathway can contribute to early fibroblast activation in ARDS.

Dysregulation of cell survival and proliferation is a feature of many lung diseases, including ARDS and IPF. However, less is known about the role of the IGF pathway in lung disease. IGF-I was originally described in the lung as alveolar macrophage-derived growth factor. IGF-I mRNA was elevated in bleomycin-induced pulmonary fibrosis in mice (Maeda A., et al., *Chest* 109:780-786 (1996)). IGF-I was implicated as a major fibroblast mitogen in BALF from patients with sarcoidosis (Allen J. T., et al., *Am J Respir Cell Mol Biol* 19:250-258 (1998)) and systemic sclerosis (Harrison N. K., et al., *Clin Sci* (*Lond*) 86:141-148 (1994)), and macrophage-derived IGF-I inhibited apoptosis of a fibroblast cell line (Wynes M. W., et al., *J Leukoc Biol* 76:1019-1027 (2004)). In eight patients with fibroproliferative ARDS (day 7), biopsies showed increased IGF-I immunostaining, which correlated with increased cell proliferation (Krein P. M., et al., *Am J Respir Crit. Care Med* 167:83-90 (2003)). Elevated levels of IGFBP-3 were detected in BALF from patients with IPF (Aston C., et al., *Am J Respir Crit. Care Med* 151:1597-1603 (1995); Pala L., et al., *J Endocrinol Invest* 24:856-864 (2001)) and sarcoidosis (Allen J. T., et al., *Am J Respir Cell Mol Biol* 19:250-258 (1998)). A recent study showed IGFBP-3 increased collagen and fibronectin synthesis by fibroblasts (Pilewski J. M., et al., *Am J Pathol* 166:399-407 (2005)). Furthermore, fibroblasts derived from patients with IPF had increased expression of IGFBP-3 compared to normal controls (Pilewski J. M., et al., *Am J Pathol* 166:399-407 (2005)). One of the interesting features about ARDS is that the lung injury (and fibrosis) resolves in the majority of patients. Without wishing to be bound by theory, one possibility is that apoptosis of fibrogenic cells (i.e., fibroblasts) is essential for the resolution of lung injury (Phan S. H., *Chest* 122:286 S-289S (2002); Uhal B. D., *Chest* 122:293 S-298S (2002); Iredale J. P., et al., *J Clin Invest* 102:538-549 (1998)). Because the IGF/IGFBP-3 pathway is a key determinant of cell survival, dampening this pathway may be necessary both for normal scarring to resolve and to prevent a prolonged fibrogenic response (ie, fibrosis). Finally, and also without wishing to be bound by theory, it is possible that the IGF pathway, through regulation by IGFBP-3, controls fibroblast survival, which contributes to the fibroproliferative response in acute lung injury. Inhibition of signaling through the IGF-1R can therefore be used to treat acute lung injury and pulmonary fibrosis.

Example 12

Insulin-like Growth Factor 1 Regulates Mouse Lung Fibroblast Behavior

To further investigate the role of IGF-1 in the lung and lung injury, the following studies were preformed. Lung fibroblasts were isolated from C57BL6 mice and examined for the effect of IGF-1 on migration, proliferation, and apoptosis.

For these experiments, lung fibroblasts were isolated from C57BL6 mice as previously described (Cerwenka et al., *J Exp Med* 189:423-434 (1999)). Cells were maintained in DMEM/10% fetal bovine serum (FBS), 100 u/ml Penicillin/100 ug/ml Streptomycin and 2 mM L-Glutamate. All cells were used by passage 6. Function-blocking antibody to the human type 1 IGF receptor (A12) was a generous gift from Dale Ludwig (ImClone Systems) (Burtrum et al., *Cancer Res* 63:8912-8921 (2003); Wu et al., *Clin Cancer Res* 11:3065-3074 (2005)). A12 inhibits IGF-1R signaling in murine and human tissues and does not cross-react with the insulin receptor (IR) (Burtrum et al., *Cancer Res* 63:8912-8921 (2003)). It was verified that the preparation of A12 was endotoxin-free by *Limulus Amebocyte* Lysate assay (Cambrex BioScience).

Antibodies to IRS-1, IRS-2, ERK, pERK were purchased from Santa Cruz Biotechnology (Santa Cruz, Calif.); antibodies to phospho IRS-1 (pSer 312), phospho IRS-2 (pSer 731) were purchased from AnaSpec Inc (San Jose, Calif.); antibodies to AKT and pAKT (pSer472/473/474) were purchased from BD Bioscience (Bedford, Mass.); horseradish Peroxidase-conjugated anti-rabbit antibodies were purchased from Rockland (Gilbertsville, Pa.); horseradish peroxidase-conjugated anti-mouse antibodies were purchased from Zymed (San Francisco, Calif.). IGF-1 was purchased from R&D Systems (Minneapolis, Minn.).

For proliferation assays, primary mouse lung fibroblasts were plated at 10,000 cells/100 µl in 96-well plates. After initial adhesion, medium was changed to serum free overnight and then IGF-1 (100 ng/ml) was added. As a positive control, cells were grown in 10% FBS; as a negative control, cell were grown in serum-free media. Cell proliferation was assayed at 48, 72 or 96 hours by colorimetric methyl thiazolyl tetrazolium (MTT) assay per manufacturer's direction (Qiang et al., *Blood* 103:301-308 (2004)). Optical density of plates was read on a Spectra Max 250 (Molecular Device, Sunnyvale, Calif.) at 570 nm. All experiments were done in triplicate and repeated three times.

For apoptosis assays, primary mouse lung fibroblasts were plated in 96-well plates (20,000 cells/well) overnight and serum-starved for 24 hours. Functional blocking antibody to the type 1 IGF receptor (A12) was added to media at indicated concentration for 24 hours. At the end of the experiment, plates were centrifuged at 200×g for 10 minutes to prevent detached cells from being aspirated, and apoptosis was measured using the Cell Death Detection ELISA-plus System (Roche Applied Science, Penzberg, Germany), which detects cytosolic histone-complexed DNA fragments. All experiments were done in triplicate and repeated at least twice. Apoptosis index was defined as ratio of experimental condition $OD_{405nm}$/control (media alone) $OD_{405nm}$.

For migration assays, primary mouse lung fibroblasts (50,000 cells/well) were plated in serum-free medium overnight on Fluoroblok transwell filters (8 µm pores, HTS FluoroBlok™ 24-Multiwell Insert System, BD Bioscience, Bedford, Mass.) pre-coated with fibronectin (50 µg/ml). Fluoroblok microporous membranes are specifically designed to detect by fluorescence only cells below the surface membrane. IGF-1 (100 ng/ml), 10% FBS (positive control) or serum-free media (negative control) was added to lower chamber. In some experiments, cells were preincubated with the blocking antibody to IGF-1R (A12, 40 µg/ml), for 1 hour. After 4 hours of migration, filters were fixed with formaldehyde and stained with DAPI (4'6-Diamidine-2'-phenylindole dihydrochloride, Roche, Indianapolis, Ind.). Migrated cells were counted in three predesignated fields for each filter. All experiments were done in triplicate and repeated at least three times.

Figure 4:
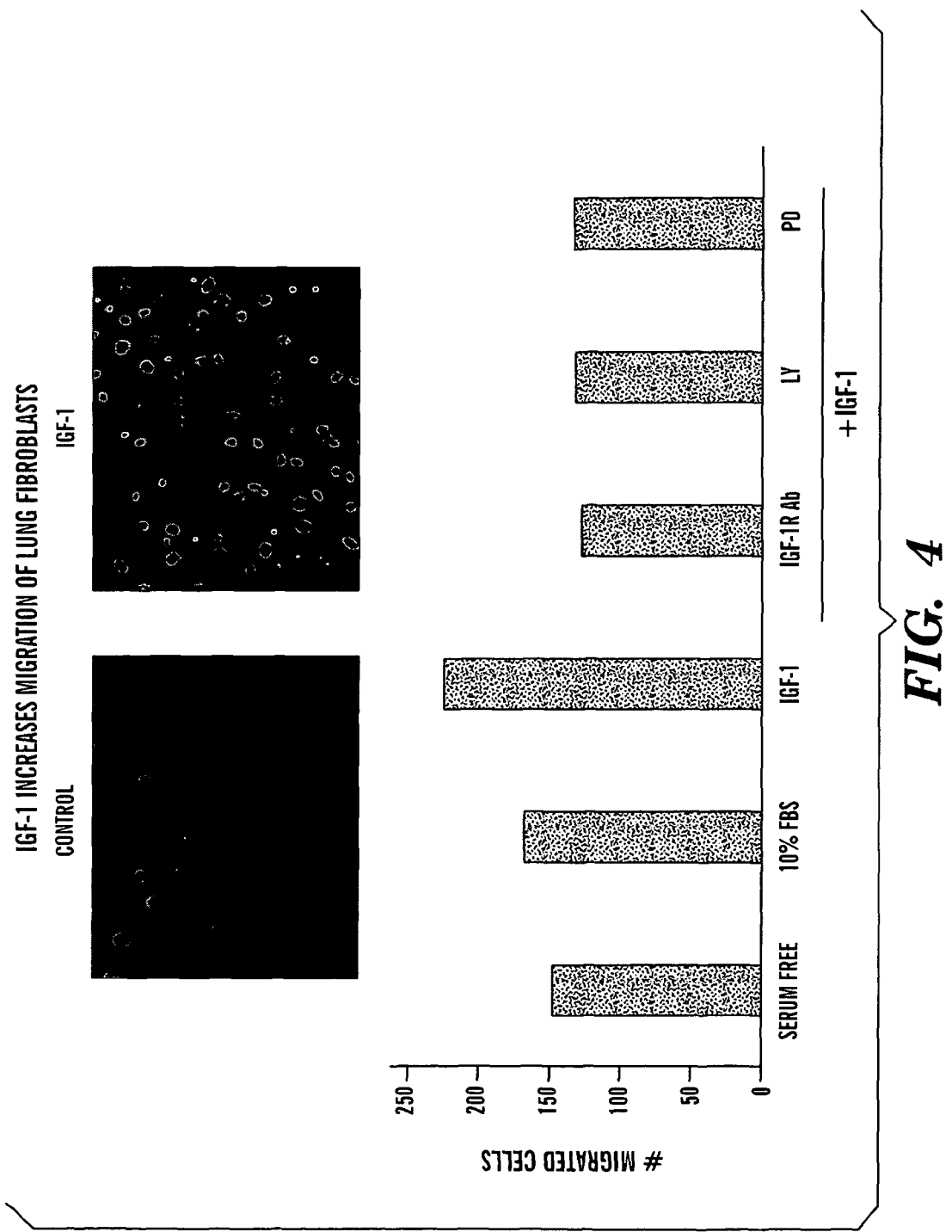
FIG. 4 shows the results of a migration assay on mouse lung fibroblasts in response to IGF-1. Graph shows results in the migration assay when mouse lung fibroblasts are treated with serum free medium, medium containing 10% FBS, or medium containing IGF-1 (100 ng/ml); results from cells treated with IGF-1 and IGF-1R antibody (A12), the PI3 kinase inhibitor LY294002 and the MAPK kinase inhibitor PD98059) are also shown.

Treatment of mouse lung fibroblasts with IGF-1 (100 ng/ml) increased migration by 1.8-fold and was inhibited by antibody to IGF-1 receptor (A12) (See FIG. 4).

Pretreatment with PI3 kinase inhibitor (LY294002) or MAPK kinase inhibitor (PD98059) partially inhibited IGF-mediated migration (see FIG. 4), suggesting that both pathways are involved in migration.

Figure 5:
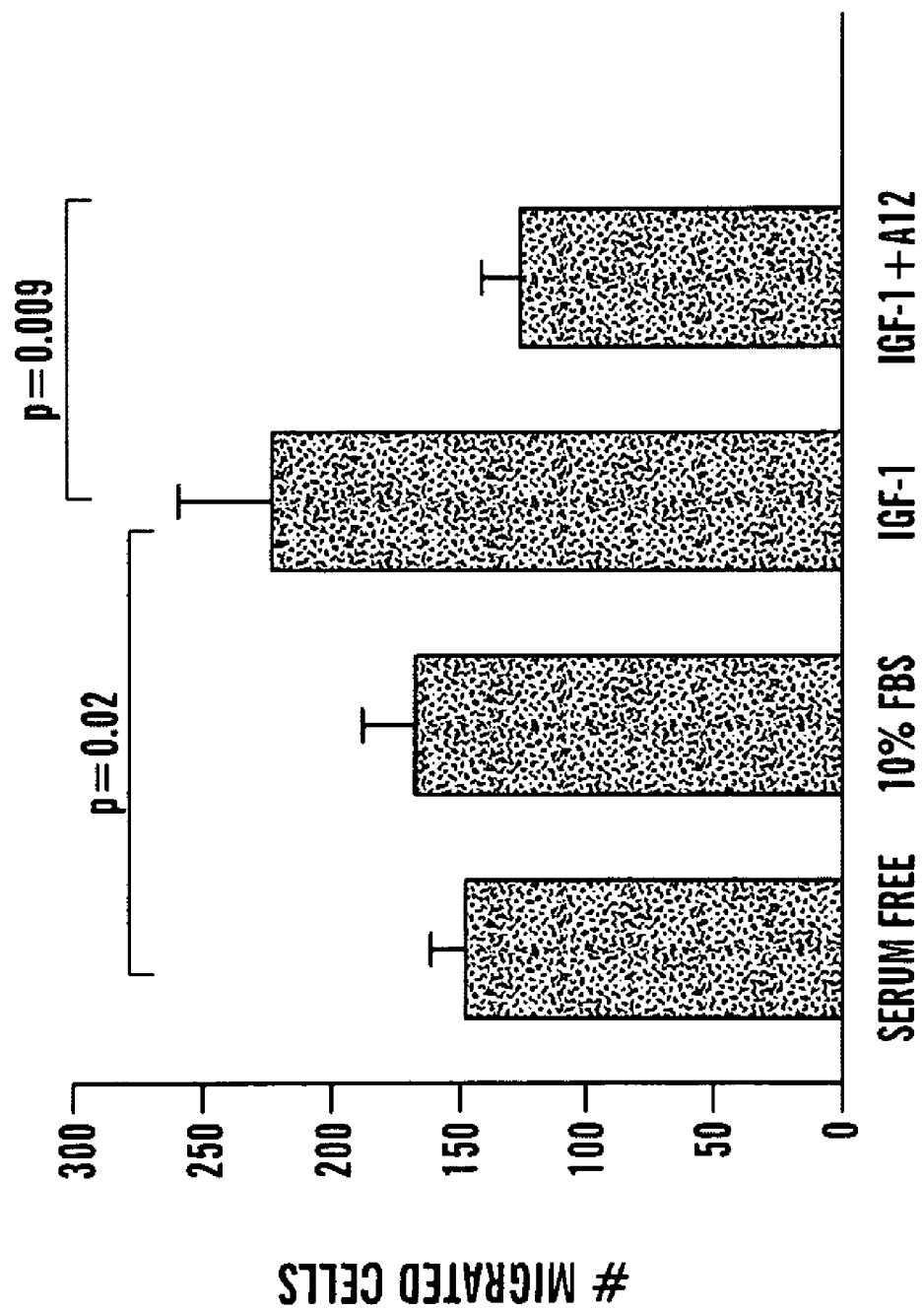
FIG. 5 shows examination of IGF-1 induced migration of fibroblasts. Mouse lung fibroblasts were plated FluoroBlok transwell filters overnight, then IGF-1 (100 ng/ml), serum free media (negative control), 10% serum (positive control) was added to lower chamber. Some cells were preincubated with the blocking antibody to IGF-1R (A12, 40 µg/ml) before the addition of IGF-1. Cells were allowed to migrate through membrane for 4 hours @ 37° C. Migrated cells were counted with Fluorescent microscope. Each experiments was done in triplicate and repeated at least three times. Average cell count ±SD are presented.

Migration of fibroblasts into intraalveolar spaces with subsequent deposition of extracellular matrix proteins is seen in pulmonary fibrosis. The inventors previously found increased IGF in BALF of patients with acute lung injury (Schnapp et al., *Am J Pathol* 169:86-95 (2006)). Therefore, it was asked whether IGF could act as a chemotactic factor for fibroblasts. The migration of mouse lung fibroblasts was examined in response to IGF using a transwell filter system. It was found that IGF-1 increased migration of MLF compared to serum containing media (FIG. 5). Treating with blocking antibody to IGF-1R (A12) abrogated the increased migration.

Figure 6:
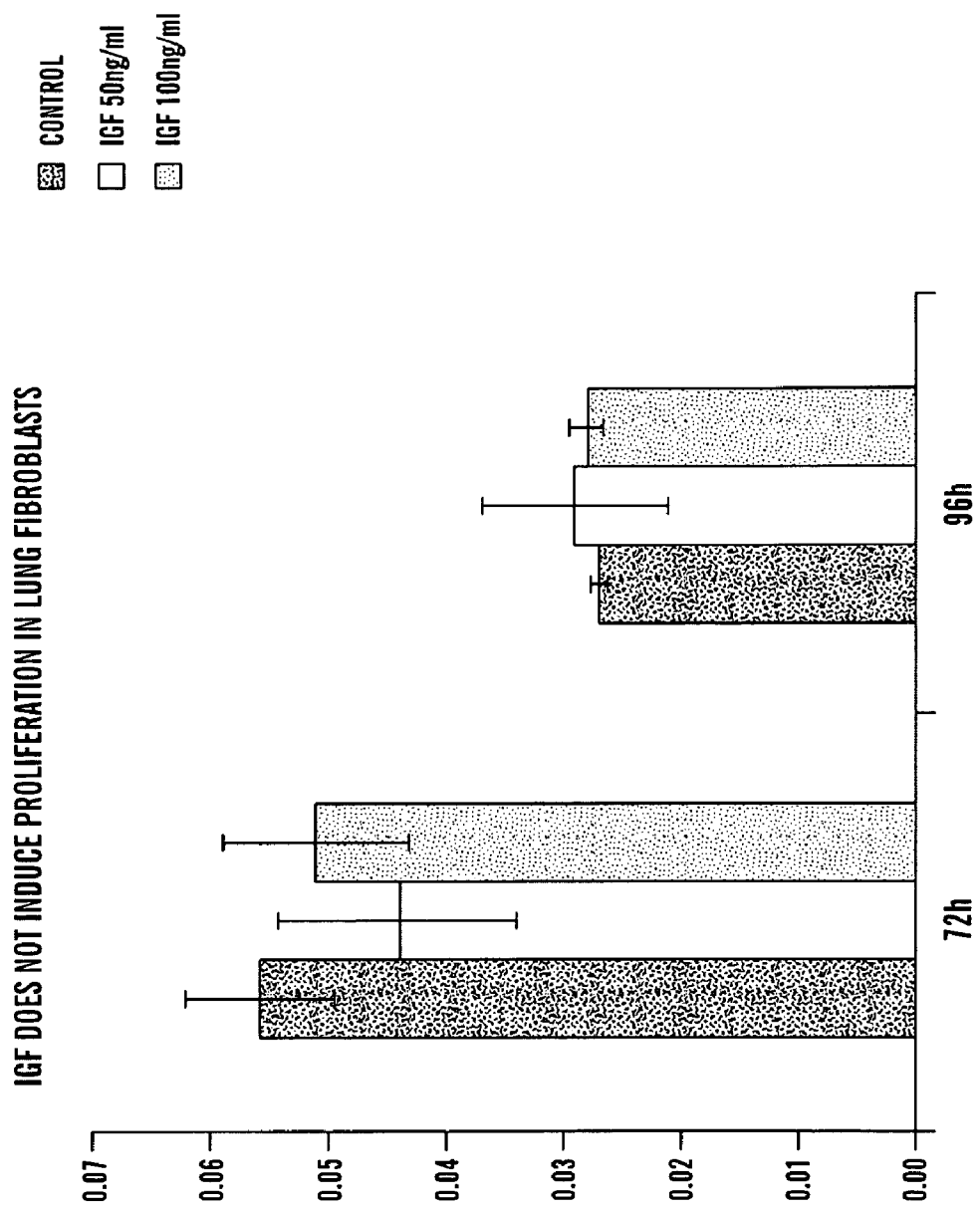
FIG. 6 shows the results of proliferation assays on mouse lung fibroblasts treated with IGF-1 (50 ng/ml and 100 ng/ml) at 72 hr and 96 hr after treatment.

In addition, proliferation in response to IGF-1 was examined. In contrast to other cell types, treatment of mouse lung fibroblasts with two different doses of IGF-1 (50 ng/ml and 100 ng/ml) did not increase proliferation (see FIG. 6). Recent data indicates, however, that IGF can induce proliferation of activated fibroblasts derived from bleomycin-treated mice (data not shown). Inhibition of IGF-1R would be expected to reduce this proliferative effect on activated fibroblasts.

Figure 7:
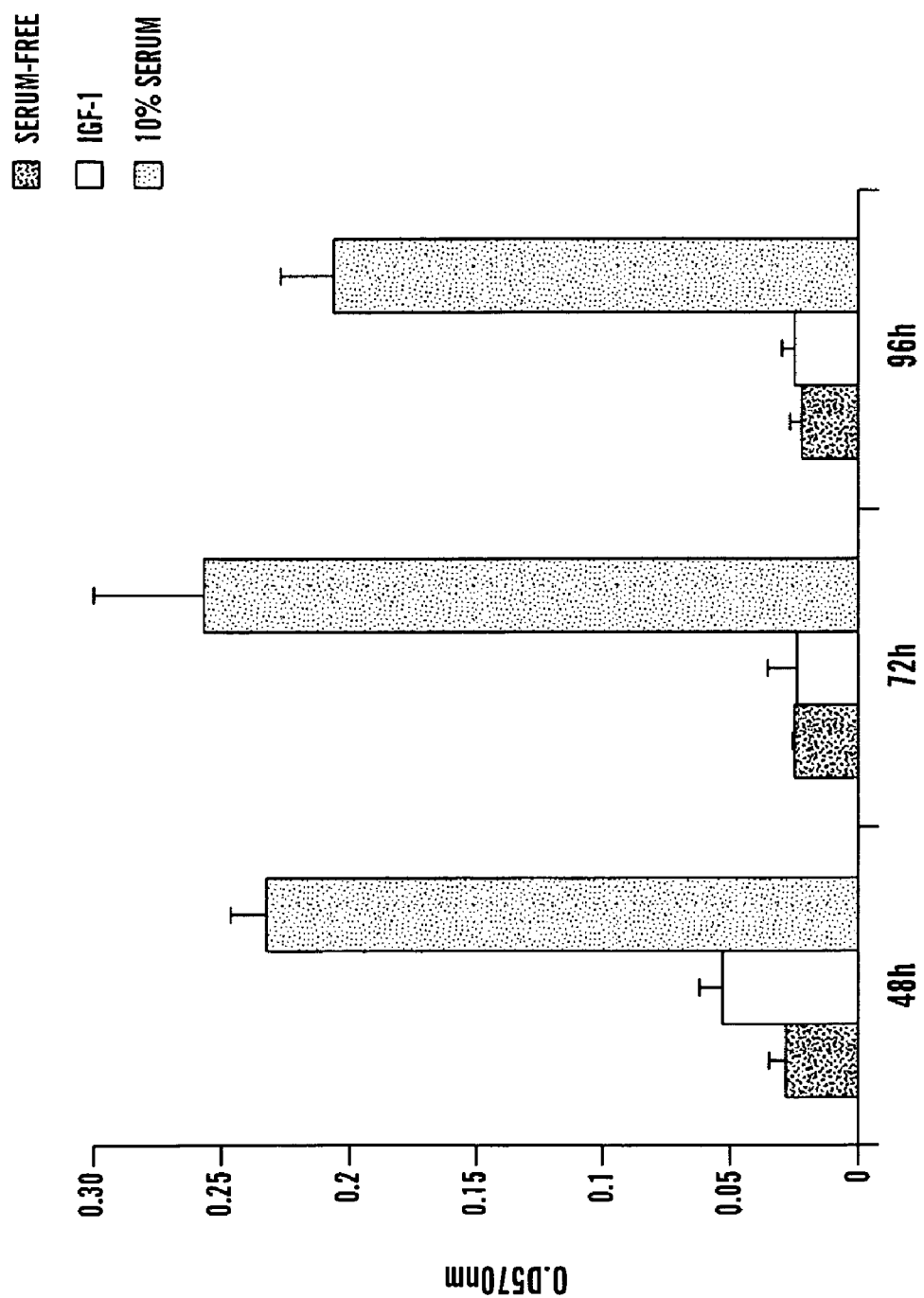
FIG. 7 shows examination of fibroblast proliferation in response to IGF. Mouse lung fibroblasts from saline-treated mice (A) or bleomycin-treated mice (B) were plated in triplicate and serum-starved overnight followed by addition of IGF-1 (100 ng/ml), serum-free media (negative control), 10% FBS (positive control), and then incubated for indicated time. Cell proliferation was measured by MTT assay. Data are shown as mean $OD_{570\ nm} \pm SD$ and are average of at least 4 independent experiments.

Previous work demonstrated IGF-1 induced proliferation in several different cell types including pleural mesothelial cells (Hoang et al., *Cancer Res* 64:7479-7485 (2004)), myeloma cells (Qiang et al., *Experimental hematology* 28:1147-1157 (2000)), and myoblasts (Coolican et al., *J Biol Chem* 272:6653-6662 (1997)). Since fibroblast proliferation is a key feature of pulmonary fibrosis (Selman, Pulmonary fibrosis: Human and experimental disease 123-188 (1990)), it was asked whether IGF-1 was mitogenic for normal lung fibroblasts. Cell proliferation was compared in the presence or absence of IGF-1 (100 ng/ml) for 24, 48, 72 and 96 h, under serum-free conditions. In contrast to other reports, increased proliferation was not observed at any of the timepoints tested (FIG. 7). Thus, the pro-survival benefit of IGF in fibroblasts appears to be due to an anti-apoptotic, rather than pro-proliferative signal.

Figure 8:
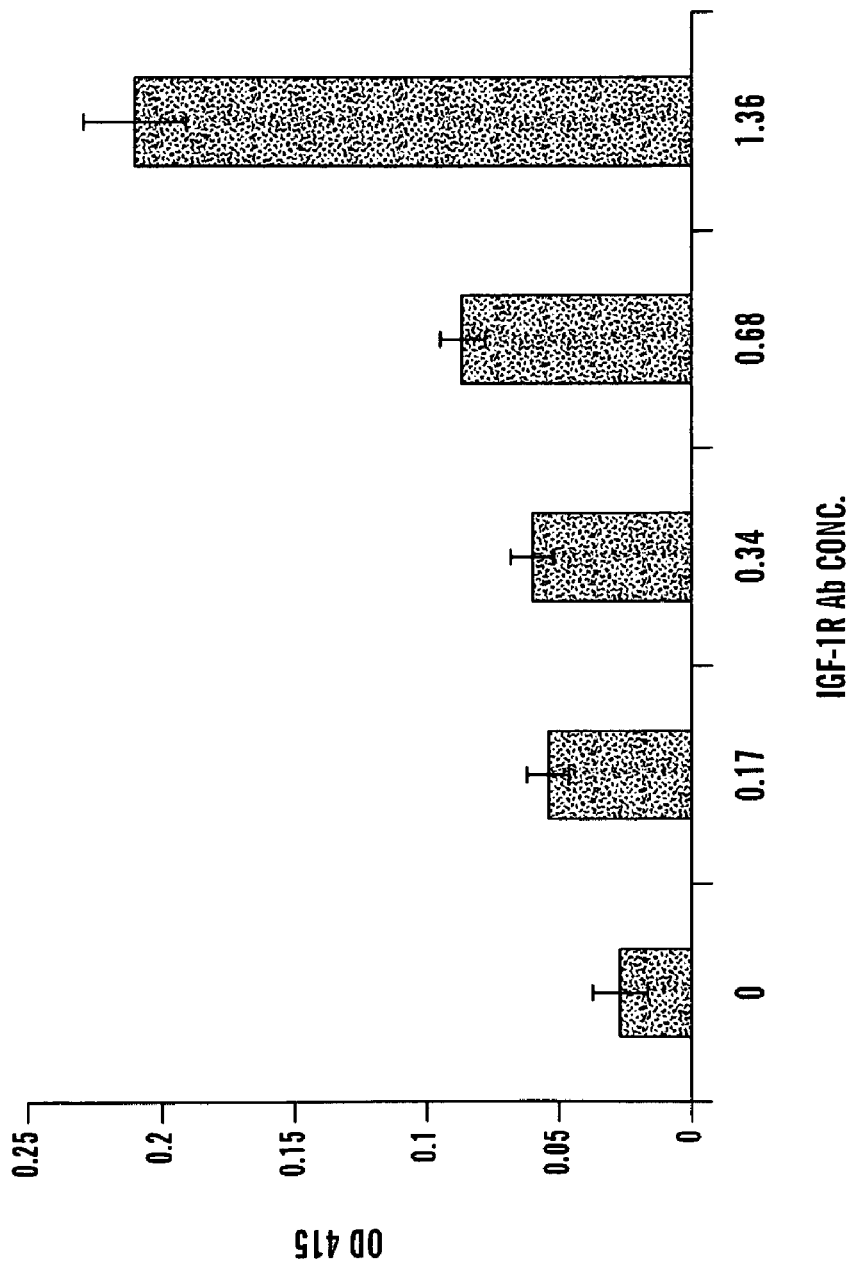
FIG. 8 shows the results of apoptosis assays on mouse lung fibroblasts treated with IGF-1R neutralizing antibody A12 over a range of antibody concentrations.

Treatment of serum-starved mouse lung fibroblasts with IGF-1R antibody increased apoptosis, indicating that IGF regulates fibroblast apoptosis, but not proliferation in fibroblasts isolated from non-injured lung (see FIG. 8). In conclusion, IGF-1 is upregulated in acute lung injury and increases migration and survival of lung fibroblasts. Thus, IGF-1 can contribute to the fibroproliferative response in acute lung injury.

Figures 9A, 9B:
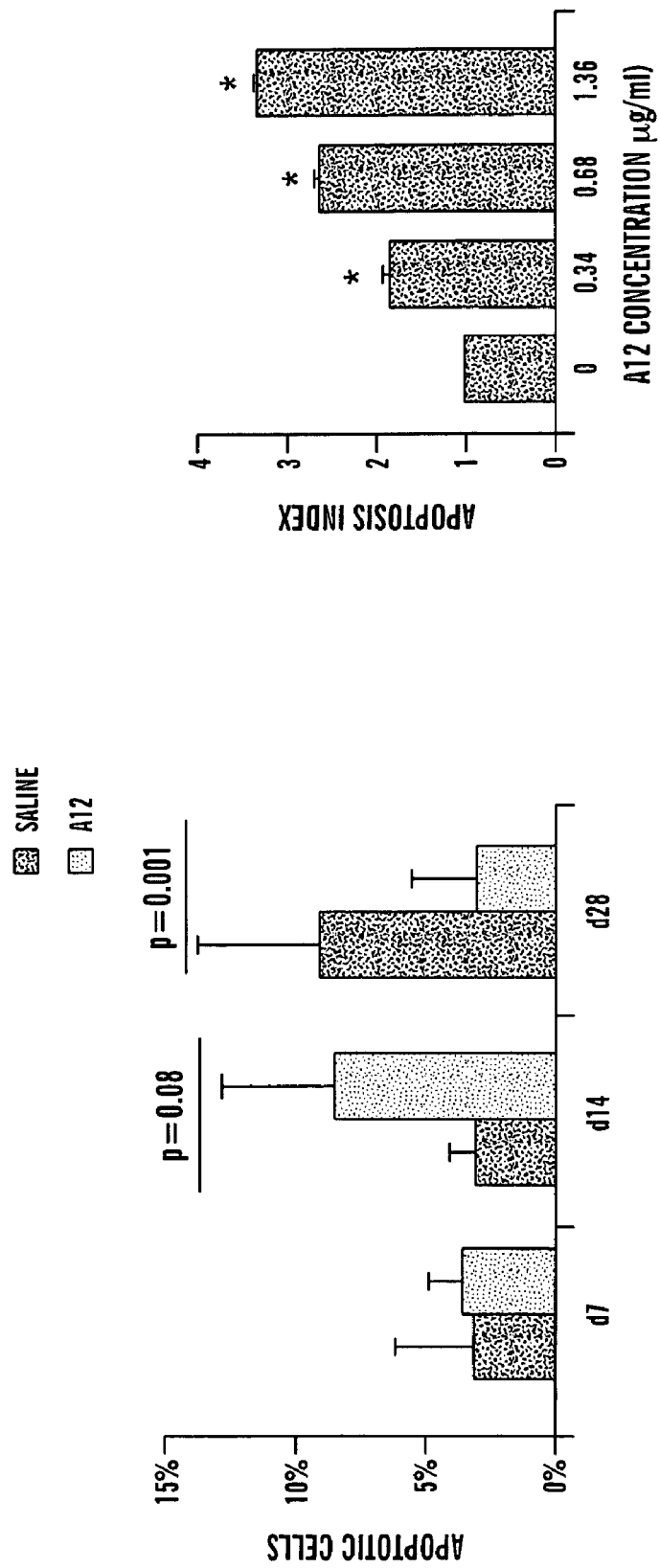
FIG. 9 shows apoptosis analyses from saline and A12-treated mouse lung after bleomycin injury. A. Quantification of TUNEL IHC by number of TUNEL positive cells/total # of cells. Average ±SD of two mice/condition and at least 500 cells analyzed per condition. B. Increased apoptosis of primary mouse lung fibroblasts treated with IGF-1R antibody. Mouse lung fibroblasts were serum starved overnight and then incubated with indicated concentration of IGF-1R antibody, A12. Apoptosis was measured by Cell Death ELISA-plus (Roche Applied Science). All experiments were done in triplicate and repeated at least twice. Apoptosis index is defined as ratio of experimental condition $OD_{405nm}$/control (media alone) $OD_{405nm}$. The data was analyzed using one-way ANOVA with Tukey's HSD post hoc test, and statistical significance (*) was determined at $p<0.05$.

The inventors previously showed that blockade of IGF pathway in human lung fibroblasts increased apoptosis under conditions of serum starvation (Schnapp et al., *Am J Pathol* 169:86-95 (2006)). These initial findings are now expanded and show that blockade of IGF pathway by A12 antibody similarly induced a dose-dependent increase in apoptosis of primary mouse lung fibroblasts (FIG. 9B). Thus, in vivo and in vitro data demonstrate that A12-treatment increases fibroblasts apoptosis.

Example 13

Figure 10:
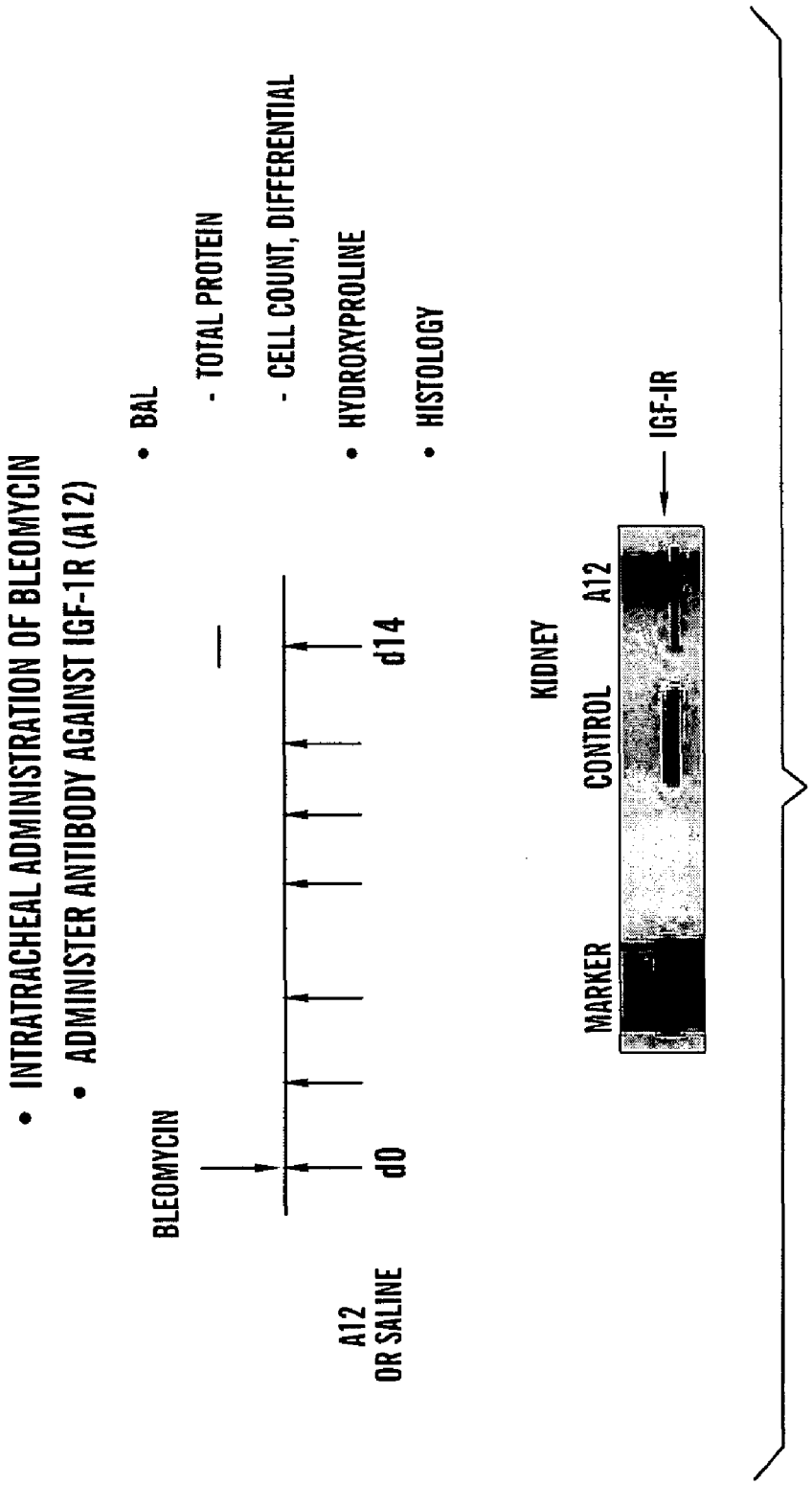
FIG. 10 shows a summary of the approach taken in experiments to evaluate the effects of IGF-1R inhibition on acute lung injury and fibrosis using the murine bleomycin injury model.

Inhibition of IGF-1R Reduces Acute Lung Injury and/or Pulmonary Fibrosis In Vivo A reduction in acute lung injury following treatment with an IGF-1R inhibitor can be demonstrated using the bleomycin-induced acute lung injury model as follows. ICR male mice are anesthetized under pentobarbital (60 mg/kg, i.v.) anesthesia, the cervical region is shaved and the skin is incised for about 4 mm from under the larynx region along the median line. Next, the muscle layer covering upper trachea is peeled off to expose the trachea. Using a micro-syringe, physiological saline or bleomycin hydrochloride (0.03 mg/animal, manufactured by Nippon Kayaku) is administered tracheally (50 µl/animal) from the tracheal smooth muscle region between cricoid cartilage. After the administration, the incised region is closed and antibiotics are administered into the thigh intramuscularly in order to prevent infection. IGF-1R inhibitor, e.g., antibody to IGF-1 receptor (A12). The A12 antibody was administered intraperitoneally at the time of bleomycin administration and subsequently 2-3× per week at a dose of 40 mg/kg (initial experiments involved dosing 3× per week, and later experiments dosed 2× per week; results were the same). Systemic effect of the antibody was monitored by Western blotting, which showed, for example, down-regulation of IGF-1R in the kidney (see FIG. 10). Controls included bleomycin-treated animals receiving saline injection in place of A12 antibody. At various time points after the induction, each animal is sacrificed by exsanguination under pentobarbital anesthesia, and lung tissue is excised to monitor for differences in lung injury in the test versus control groups. In addition, bronchoalveolar lavage is performed, with analysis of the resulting fluid for differences in total protein, cytokines, inflammatory cells and fibroblasts or in the responsiveness of such cells to, e.g., apoptotic or other stimuli. Lung hydroxyproline content is measured as a measure of fibrosis. Changes in lung tissue histology are also monitored. The approach is summarized in FIG. 10. Further details on the processing of lung tissue for analysis include the following. At time of sacrifice, the right main stem bronchus was tied off and the left lung was isolated and lavaged with 1 ml of PBS containing 0.6 mM EDTA warmed to 37° C. Bronchoalveolar lavage fluid (BALF) total cell count was determined by trypan blue exclusion and cell differential was determined on Diff quick (Dade Behring Ag, Düdingen, Switzerland) stained cytospins. Following brief centrifugation, cell-free supernatants were used for measurement of total protein by Bio-Rad protein assay (Bio-Rad laboratories, Hercules, Calif.). The left lung was snap frozen and used for hydroxyproline measurement as previously described (Woessner, *Arch Biochem Biophys* 93:440-447 (1961)). Hydroxyproline concentration was extrapolated from a standard curve. The right lung was inflated and fixed with 4% formaldehyde at 25 cmH$_2$O pressure for histologic evaluation.

For immunohistochemistry, sections obtained from paraffin embedded, fixed lungs underwent antigen retrieval by boiling sections in 10 mM sodium citrate buffer (pH 6.0). Endogenous peroxidase activity quenched by incubating in 1% H2O2 for 10 min. To block non-specific binding of immunoglobulins, slides were incubated with 1.5% goat serum in PBS for 1 hr at room temp. Sections were incubated with IGF-1-R-alpha antibody (1:200, Santa Cruz Biotechnology, Santa Cruz, Calif.) overnight at 4° C. and then incubated with biotinylated goat anti-rabbit antibody (1:200, Santa Cruz Biotechnology, Santa Cruz, Calif.) for 30 min at room temp. Sections were processed with Vectastain ABC Kit (Vector Laboratories, Burlingame, Calif.) followed by DAB peroxidase kit (Vector Laboratories, Burlingame, Calif.) according to manufacturer's instructions. Slides were then counterstained in hematotoxylin dehydrated and mounted using permanent aqueous medium (Permount, Fisher Scientific).

For TUNEL assay, tissue sections were deparaffinized using standard protocols and permeabilised with proteinase K (10 µg/ml in 10 mM Tris-HCl) for 30 mins at 37° C. Non-specific binding sites were blocked with 1 mg/ml BSA in 50 mM Tris-HCl for 10 mins at 37° C. TUNEL positive cells were detected with Fluorescein In Situ Cell Death Detection Kit (Roche). Nuclei were counterstained with DAPI. To quantitate apoptosis, at least 2 mice per timepoint were examined and a blinded observer counted number of TUNEL positive cells and DAPI positive cells in 4 independent fields/mouse. At least 500 cells were analyzed per condition.

To examine a potential mechanism of decreased hydroxyproline content, the number of apoptotic cells in A12 and vehicle-treated mice was compared. At the early timepoint (d14), there was an increase in TUNEL-positive cells in A12 treated mice (FIG. 9A). At day 28, there were fewer apoptotic cells in A12 treated mice compared to vehicle-treated mice.

Figure 11:
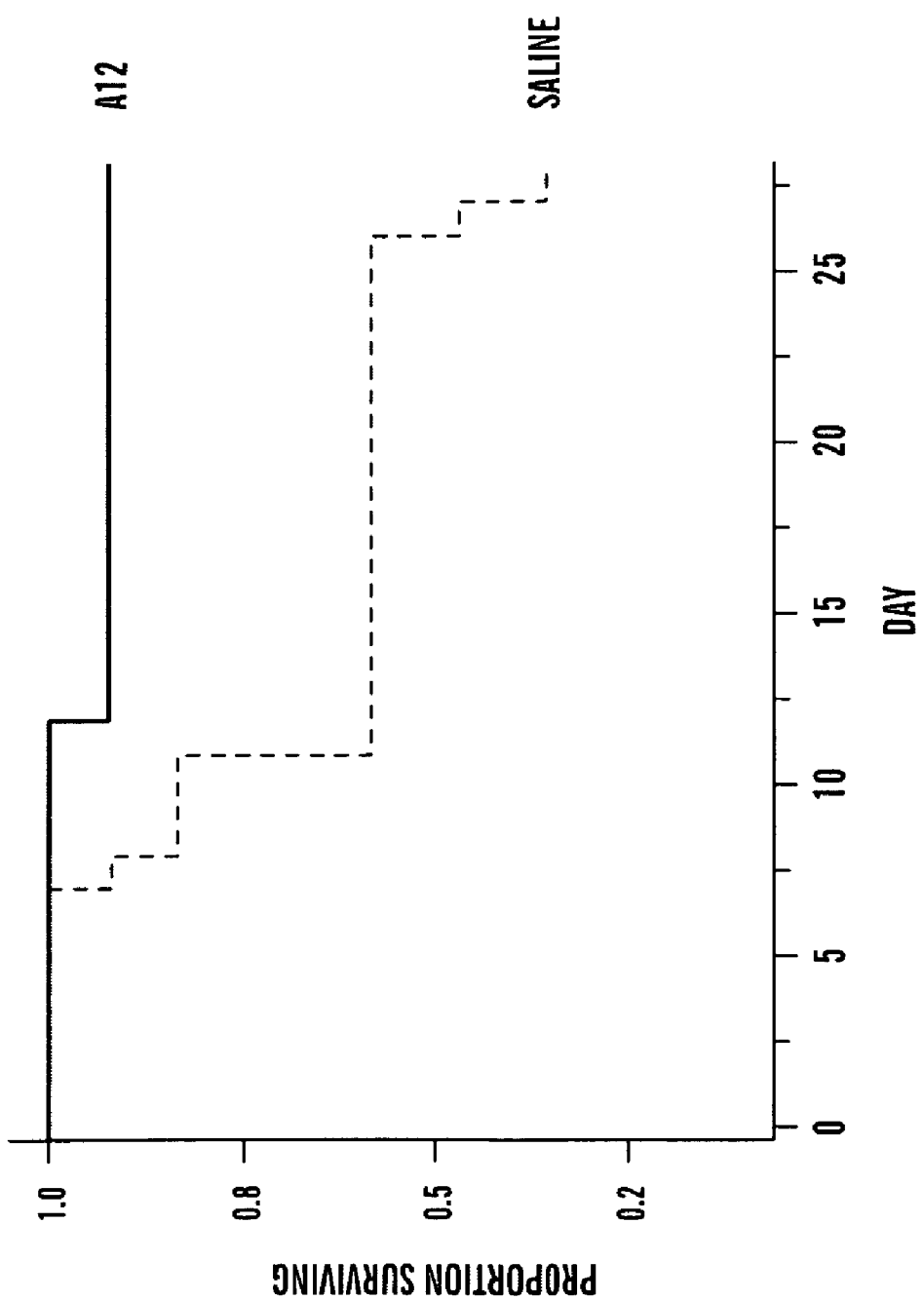
FIG. 11 shows a Kaplan-Meier survival curve from bleomycin treated mice receiving saline or A12 anti-IGF-1R neutralizing antibody.

The proportion of bleomycin-treated mice administered A12 antibody surviving was significantly greater than bleomycin-treated mice receiving saline alone at 7-14 days post-bleomycin treatment (see FIG. 11). A12 treated mice (n=24) showed a statistically significant survival benefit compared to saline control mice (n=24, p=0.01). In the saline control group, most deaths occurred between 7 and 10 days, as expected in this model. Of note, A12 treated mice had significantly greater weight loss compared to saline control mice (20% vs 13% by d14), but had less evidence of respiratory or systemic distress as measured by body condition scoring (Ullman-Cullere and Foltz, *Lab Anim Sci* 49:319-323 (1999)). In the absence of bleomycin, administration of A12 alone had no affect on survival, lung histology, BAL protein concentration or cell count (not shown).

Figure 12:
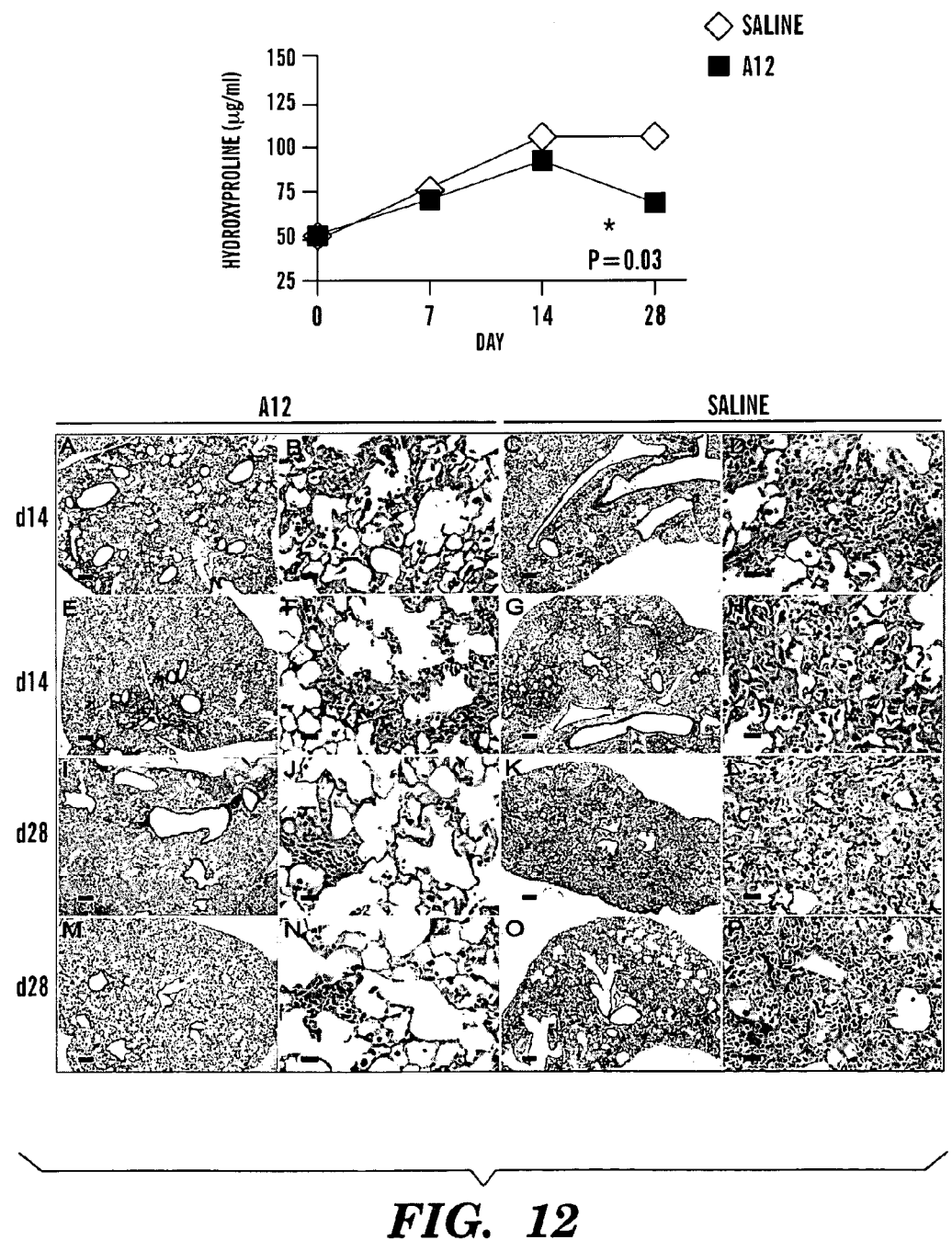
FIG. 12 shows hydroxyproline content and lung histology of bleomycin-treated mice receiving A12 or saline. Hydroxyproline content of left lungs from A12-treated mice and saline-control mice after bleomycin instillation. The data was analyzed using one-way ANOVA with Tukey's HSD post hoc test, and statistical significance (*) was determined at $p<0.01$. Bottom. Histology of A12-treated mice and saline-treated mice at 14 days (A-H) and 28 days (I-P) following bleomycin instillation. Lung sections from A12-treated mice show relatively normal interstitium and less fibrosis (*) compared to saline control mice. Right middle lobe from 2 mice/group shown. Original magnification and scale bar 4×, 200 µM (A, E, C, G, I, M, K, O), 40×, 25 µm (B, F, D, H, J, N, L, P). H&E stain.

While mortality over 7-14 days was significantly reduced by A12 antibody treatment, there was a similar degree of fibrosis over 7-14 days in animals receiving A12 antibody and saline, as reflected by hydroxyproline level (see FIG. 12, days 7 and 14). That is, the inhibition of IGF-1R did not appear to block the initial fibrotic response. However, at 28 days, the animals receiving A12 antibody had significantly lower lung hydroxyproline levels than those receiving saline, indicating enhanced resolution of fibrosis in the antibody-treated animals.

Hydroxyproline content of lungs was measured as a marker of lung fibrosis. There were no significant differences in hydroxyproline content at day 7 and day 14 between the 2 groups (FIG. 12). However, at day 28, there was significantly less hydroxyproline in A12-treated mice compared to control (p=0.03) or compared to d14 measurements (p=0.001), suggesting A12 treatment affected resolution of fibrosis rather than initial establishment of fibrosis.

The mechanism(s) of survival and resolution of fibrosis was further evaluated by looking at BALF total protein (see FIG. 13A) and total cell count (see FIG. 13B) and differential cell count, as well as histological differences (see FIG. 12). There was no significant difference in BALF total protein, total or differential cell count at days 7 and 14. Only subtle histological differences were observed at day 14. Reduced evidence of fibrosis was evident at day 28 in A12-treated animals.

Figure 13A:
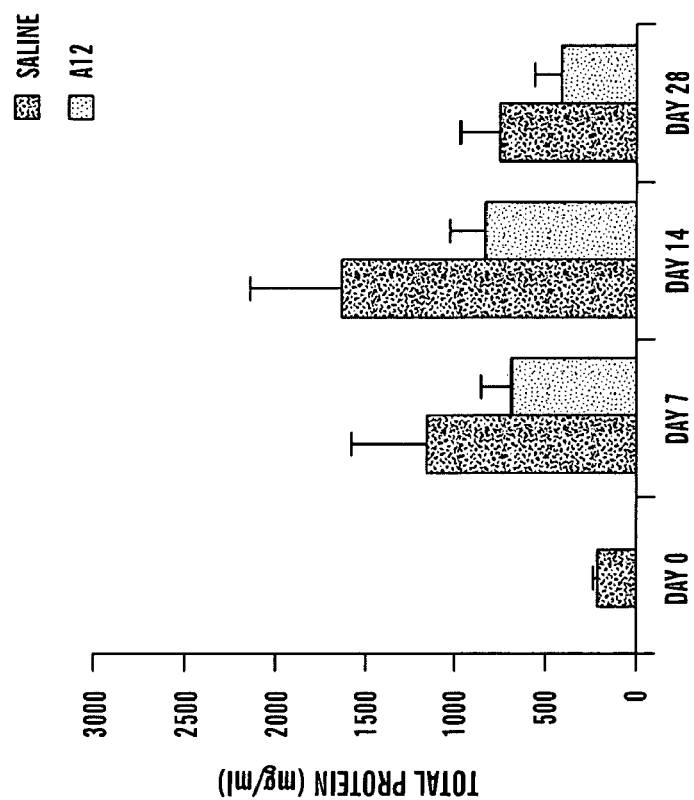
FIG. 13 shows the results of measurements of BALF total protein concentrations (A) and cell count (B) at 0 (baseline), 7, 14, and 28 days after bleomycin instillation in A12 treated mice and saline control mice. Average values ±SEM are shown.

To assess whole lung permeability and degree of inflammation, total protein, cell count and cell differentials were measured in BALF. As expected, bleomycin-treated mice had significantly elevated total protein and cell count compared to untreated (day 0) mice. At the early timepoints (d7, d14), there was no difference in BALF protein concentration in bleomycin-A12 vs. bleomycin-saline treated mice (p>0.3). By 28 days, there was a trend towards decreased BALF protein concentration in A12-treated mice compared to saline treated mice, but this did not achieve statistical significance (p=0.16) (FIG. 13A).

Figure 13B:
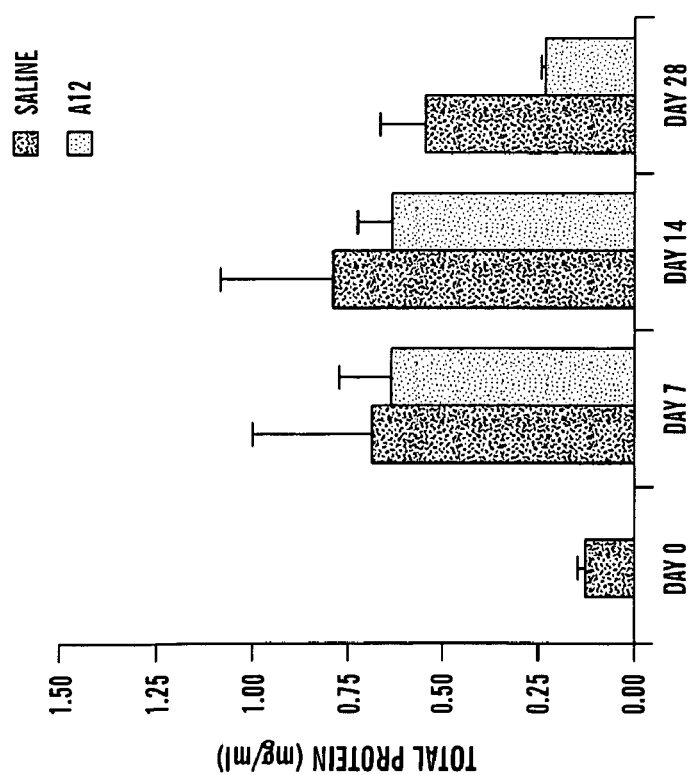

While the total cell counts were not statistically different between A12 and saline treated mice, there was a trend for decreased cells in A12 treated mice (FIG. 13B). There was no difference in the cell differential between the 2 groups at any of the time points tested.

Histology confirmed hydroxyproline measurements (FIG. 12). In all mice, right middle lobe (RML) histology is shown, since the majority of the lobe can be visualized under low magnification, to allow for global assessment of injury and to minimize bias due to the patchy nature of bleomycin injury. At 14 days, both groups showed areas of fibrosis although there seemed to be qualitatively less fibrosis in A12-treated mice (FIG. 12A-H). However, the difference was more pronounced by d 28 (FIG. 12I-P). At d28 after bleomycin instillation, the RML from saline-treated mice were smaller, had more distortion of normal lung architecture, and more areas of airspace obliteration and interstitial thickening, whereas RML from A12-treated mice had better preservation of lung architecture and lung size, and fewer areas of fibrosis.

Figure 14:
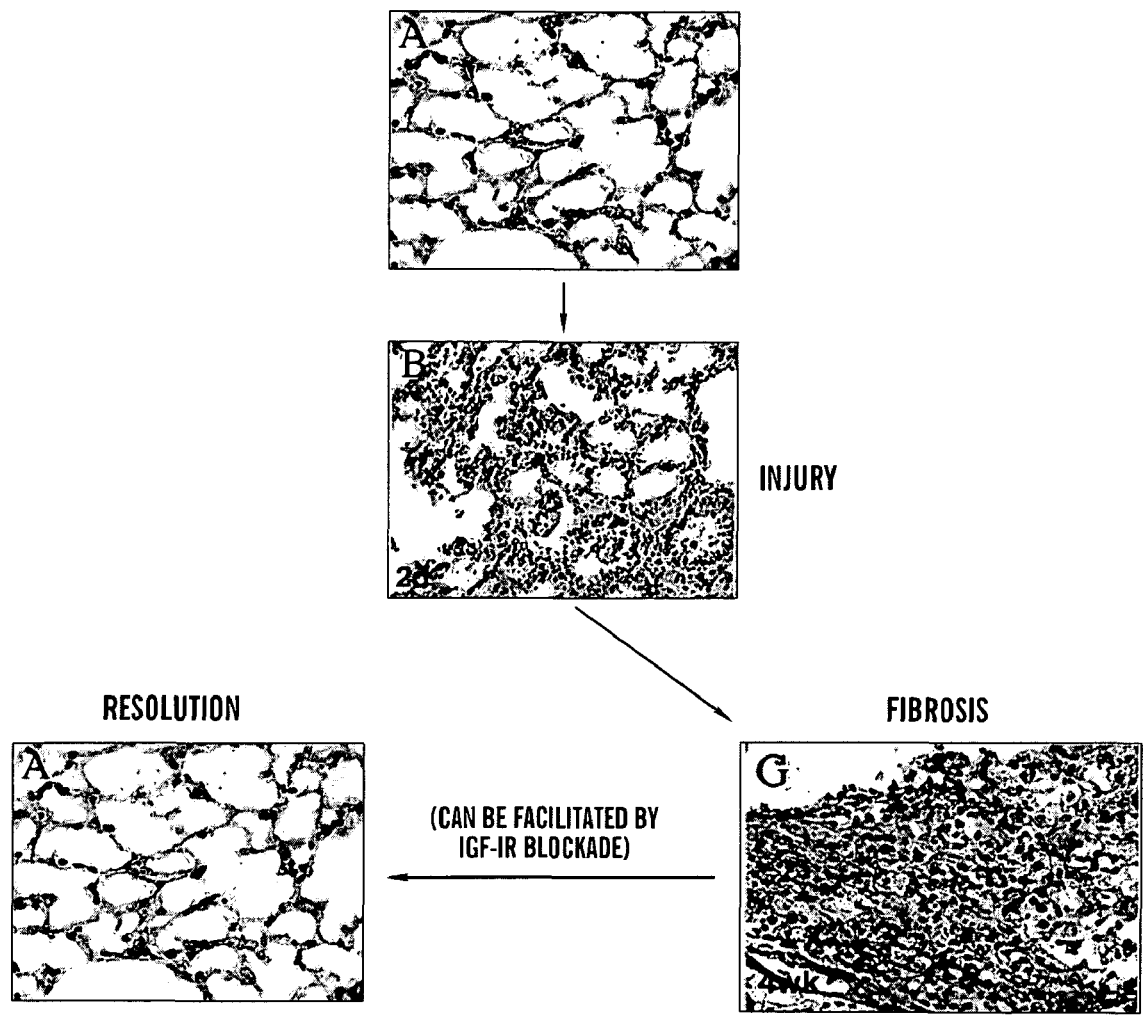
FIG. 14 shows a schematic representation of the course of bleomycin-induced lung injury and recovery using the histology of mouse lung before (panel A, top), and after bleomycin injury. Panel B shows histology at two days post injury. The next panel (following the arrows) shows histology at 4 weeks (28 days) post injury, and the last panel (following the arrows) shows histology after resolution of the injury.

Without wishing to be bound by theory, it is thought that the improved survival and earlier resolution of fibrosis involve separate mechanisms. FIG. 14 shows a histological schematic of the acute injury/recovery process. Panel A (top) illustrates normal lung tissue histology, panel B illustrates acute injury histology at 2 days post-bleomycin, panel C illustrates fibrosis at 28 days, and the final panel illustrates resolution of the fibrosis. It is thought that the improved survival upon IGF-1R inhibition in the bleomycin injury model may be due to reduced acute injury and inflammation (which would be representative of ARDS/acute lung injury in humans), while the enhanced resolution of fibrosis is thought to reflect decreased survival of fibroblasts—i.e., an increase in apoptosis.

Example 14

Evaluation of Signaling Pathways Involved in Fibroblast Responses to IGF-1

Figure 15:
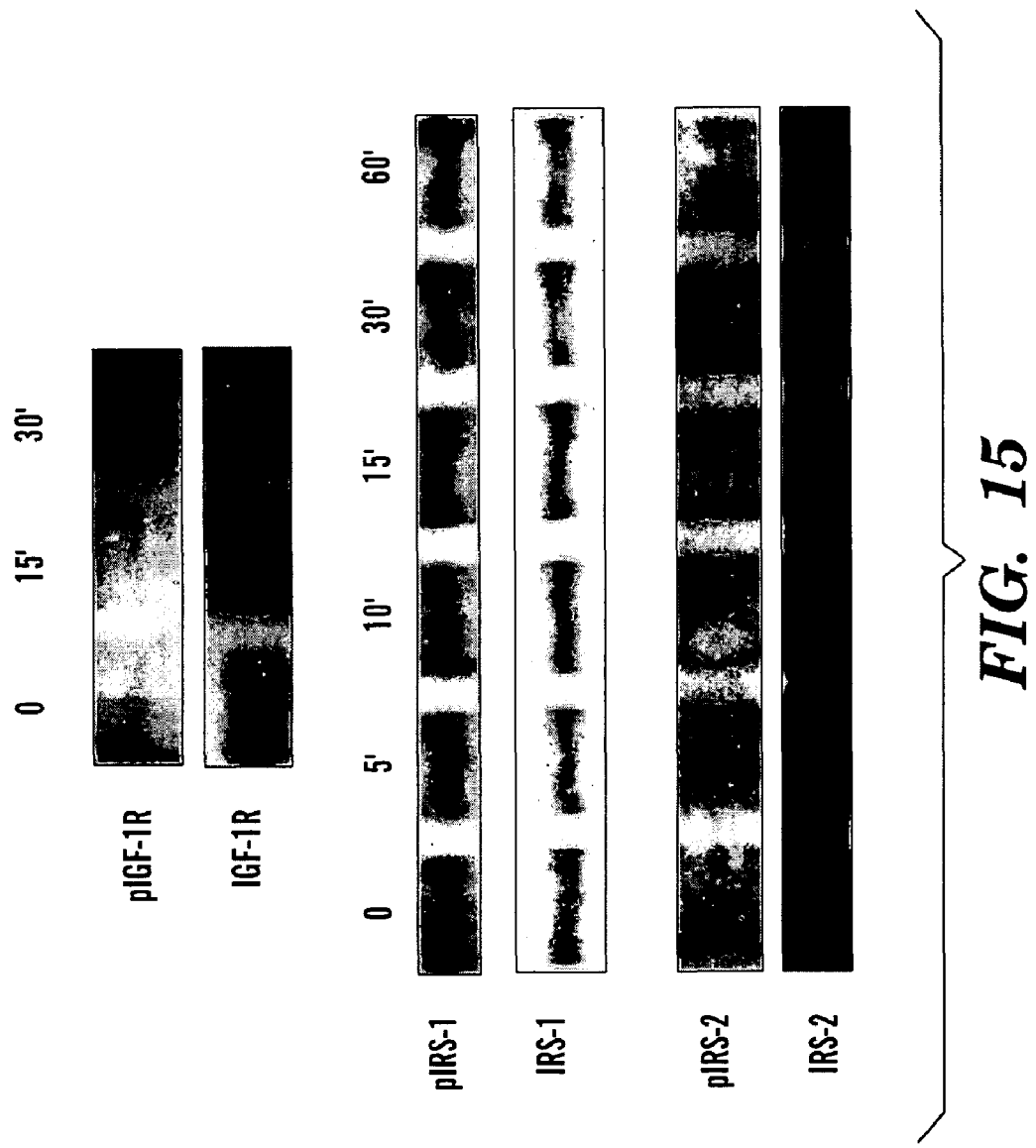
FIG. 15 shows the results of experiments evaluating the signaling pathways used in IGF-stimulated lung fibroblasts. Tyrosine phosphorylation of receptor tyrosine kinase substrates was evaluated. Mouse lung fibroblasts were serum-starved overnight and then stimulated with IGF-1 (100 ng/ml) for indicated times. Cells were lysed, and proteins separated by SDS-PAGE. Each membrane was blotted with indicated phospho-antibody then stripped and reblotted with antibody to total protein. Substrates include IGF-1R, IRS-1 and IRS-2. The tyrosine phosphorylated forms of the substrates are indicated by pIGF-1R, pIRS-1 and pIRS-2, respectively.
Figure 16:
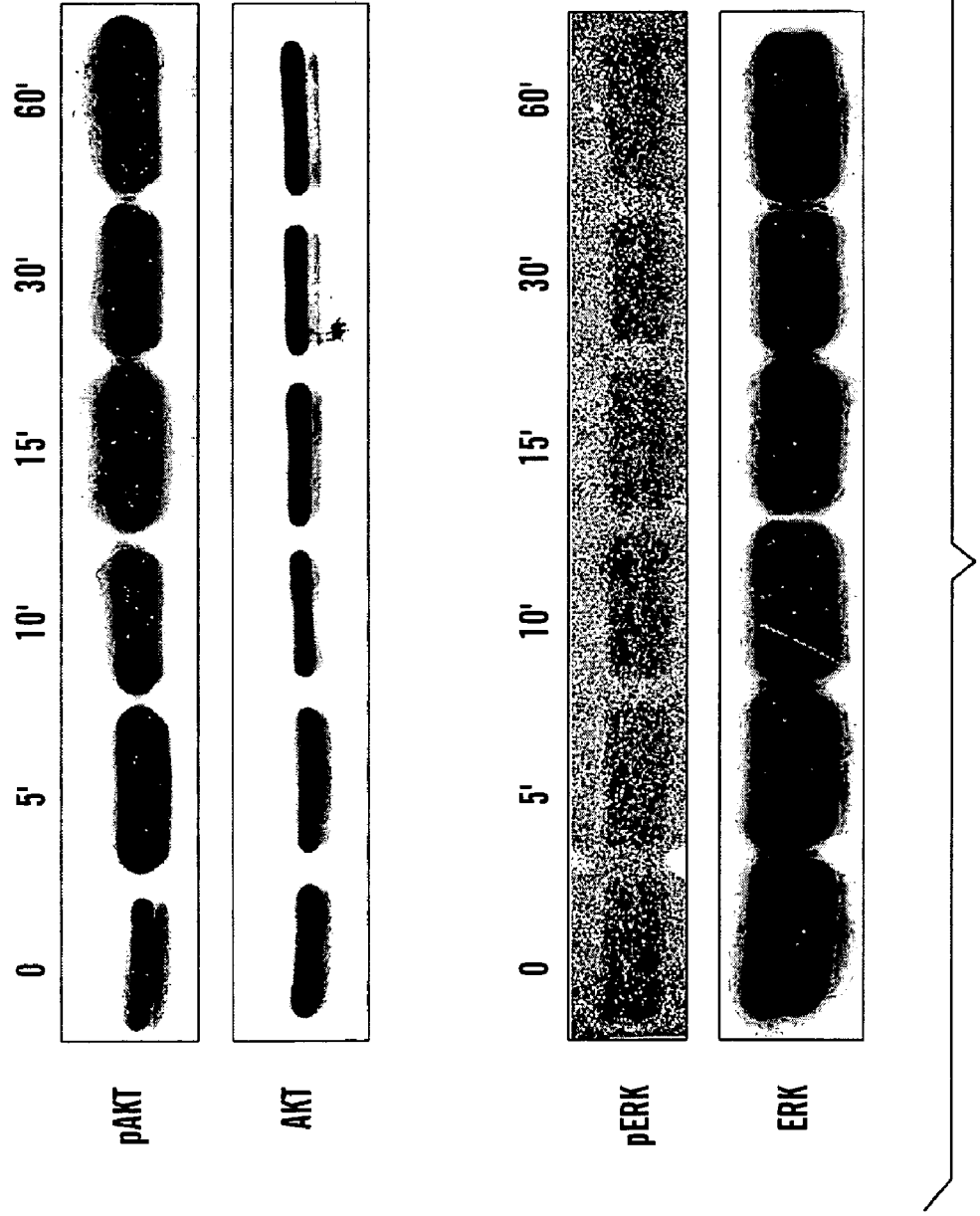
FIG. 16 shows the results of further experiments evaluating the signaling pathways used in IGF-stimulated lung fibroblasts. Tyrosine phosphorylation of receptor tyrosine kinase substrates was evaluated. Substrates include AKT, ERK. The tyrosine phosphorylated forms of the substrates are indicated by pAKT, pERK, respectively.
Figure 17:
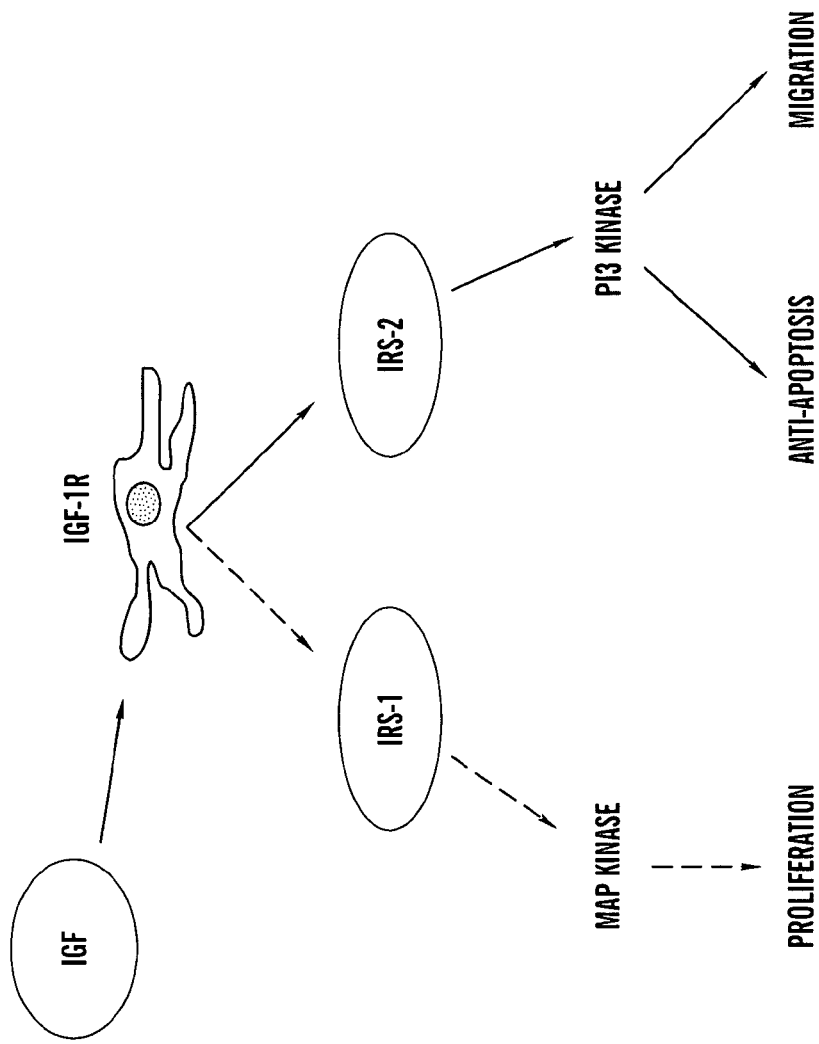
FIG. 17 shows a schematic summarizing the results of signaling pathway evaluations—the IRS-2 and PI3 Kinase pathways are activated by IGF in mouse lung fibroblasts.

To determine the signaling pathways activated by IGF in lung fibroblasts, we first examined the expression and phosphorylation of IGF-1R following stimulation with IGF (FIG. 15). IGF-1R was phosphorylated within 10 minutes of IGF stimulation. We then examined lung fibroblasts for the presence of the major IRS, IRS1, and 2, and examined their phosphorylation following IGF stimulation (FIG. 15). We found that while fibroblasts express both IRS-1 and IRS-2, only IRS-2 was activated following IGF stimulation (FIG. 15). IRS-1 showed constitutive level of phosphorylation that did not change following stimulation with IGF. IRS-2, on the other hand, showed increased phosphorylation by 10 minutes that persisted until 30 minutes, then decreased to baseline levels again. Both PI3 kinase and MAPK pathways have been implicated in IGF signaling in different cell types. We found that Akt, downstream substrate of PI3-kinase, was phosphorylated in response to IGF-1 stimulation by 15 minutes and persisted until 60 minutes (FIG. 16). In contrast, ERK, downstream substrate of MEK ½, is present in lung fibroblasts, but did not undergo phosphorylation following stimulation with IGF-1 (FIG. 16). Thus, in primary mouse lung fibroblasts, it appears that IRS-2 and PI3 kinase are the major pathways activated by IGF-1 under the conditions tested. Taken together, these and other data indicate that IGF activates the IRS-2 and PI3 kinase pathways in lung fibroblasts (summarized schematically in FIG. 17).

As noted above, one of the interesting features about ARDS is that the lung injury resolves in the vast majority of patients. Without wishing to be bound by theory, apoptosis of lung fibroblasts may be an essential part of this resolution and the decrease in IGF-I levels may be an important permissive activity for the apoptosis of fibroblasts to occur (Iredale et al., *J Clin Invest* 102:538-549 (1998); Phan, *Chest* 122:286 S-289S (2002); Uhal, *Chest* 122:293 S-298S (2002)). Further details from the blockade of IGF-1R are provided in Example 15, below.

Example 15

Effects of Blockade of Igf-1 Receptor in the Murine Model of Bleomycin-Induced Lung Injury and Fibrosis For these experiments, the bleomycin-induced lung injury was initiated in the manner described herein above, and the A12 anti-IGF-1R antibody was used for receptor blockade. Mice treated with bleomycin were treated with a monoclonal antibody against the IGF-1 receptor (A12) or vehicle.

For Real-Time PCR, total RNA was isolated from lungs at day 0, d1, d3, d7, d14, d21, and d28 following bleomycin treatment using Qiagen RNeasy Midi Kit per manufacturer's specifications. Total RNA was reverse-transcribed to cDNA using Applied Biosystems High-Capacity cDNA Archive Kit. Real-time PCR was done using ABI 7900HT with the use of pre-designed primer and probes (ABI TaqMan Gene Expression Assays) for HPRT (as endogenous control) and IGF (as target probe). Analysis was done using MS Excel calculating RQ by 2-DDCT. At least 5 mice per timepoint were examined. P values were calculated using Bonferroni correction for multiple comparisons.

For Western Blot analyses, cells were grown to 70% confluence, placed in serum free medium overnight and then IGF-1 (100 ng/ml) was added for 5, 10, 15, 30 and 60 minutes. At indicated time points, cells were washed in ice-cold PBS and lysed in buffer containing 100 mM Tri-HCl (pH 7.4), 150 mM NaCl, 1 mM $CaCl_2$, 0.1% SDS, 1% Triton-X, 0.1% NP-40, 1 mM $NaVa_3$ (sodium vanadate), 1 mM NaF (sodium Fluoride) and protease inhibitor cocktail tablet (Roche). Protein concentrations were determined by the BCA assay (Pierce). Equal amounts of protein were separated by sodium dodecyl sulfate-polyacrylamide gel electrophoresis (SDS-PAGE), and electrophoretically transferred to PVDF membrane. Membranes were blocked with 5% nonfat dry milk/0.05% Tween-20/PBS for 2 hours, incubated with primary antibody for 2 hours at room temperature, washed with 0.05% Tween-20/PBS, incubated with horseradish peroxidase-conjugated secondary antibody (1:5000) for 2 h, washed with 0.05% Tween-20/PBS and then developed with enhanced chemiluminescence (ECL) technique (Amersham, England).

For statistical analyses of the data, means of more than two groups of data were compared using one-way analysis of variance (ANOVA) with Tukey's honestly significant difference (HSD) post hoc test. In some cases, Kaplan-Meier Survival Analysis was performed using JMP IN v5.1; statistical significance was determined using log rank test.

A. Time Course of IGF Expression Following Bleomycin Injury

Figure 18:
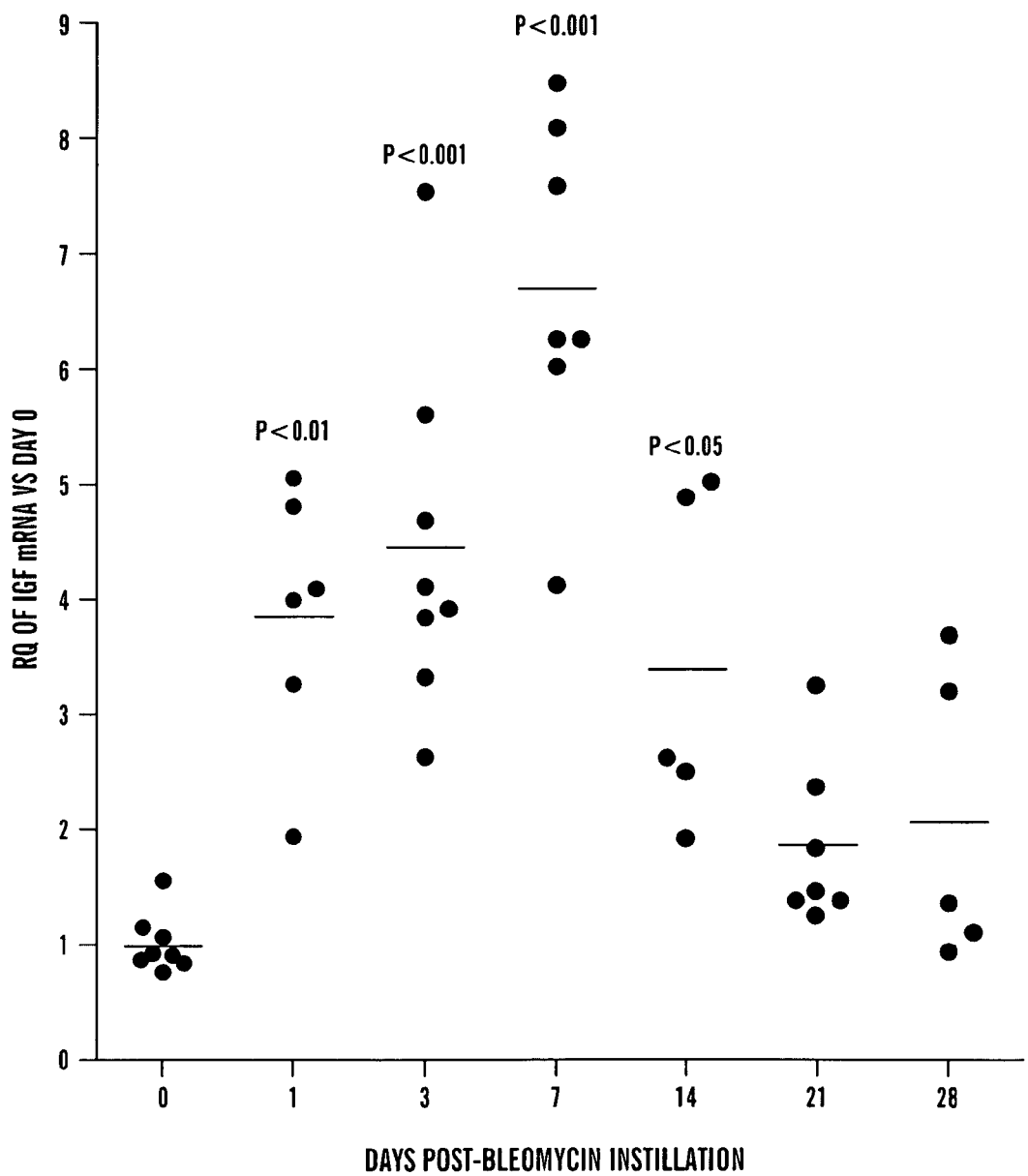
FIG. 18 shows real time PCR analysis of IGF mRNA expression following bleomycin administration. Data were normalized to HPRT expression. Y axis represents fold increase compared to day 0. Each point represents an individual mouse. Mean value is indicated.

The inventors previously demonstrated in patients that IGF was upregulated early in ARDS, and decreased in late ARDS (Schnapp et al., *Am J Pathol* 169:86-95 (2006)). Analysis of IGF expression following bleomycin injury in mice by qRT-PCR revealed significantly increased IGF mRNA expression by day 1 following bleomycin administration that peaked at day 7 (7-fold increase) (FIG. 18). IGF mRNA levels decreased at later time points, but remained elevated compared to baseline levels.

B. Downregulation of IGF-1R in A12-Treated Mice

Figure 19A:
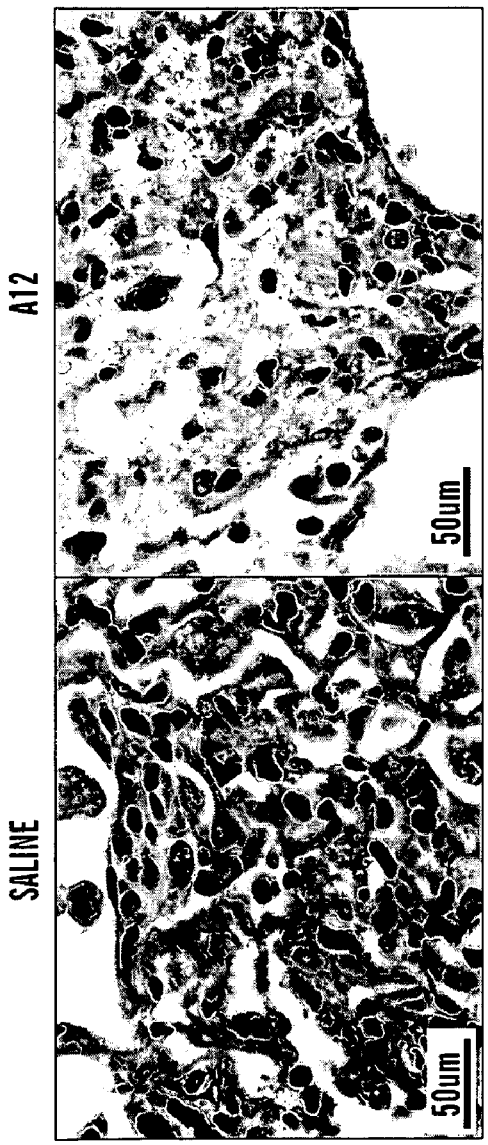
FIG. 19 shows decreased IGF-1R expression following systemic A12 administration. A. IHC for IGF-1R was performed on lungs at day 7 post-bleomycin. B. Western blot analysis for IGF-1R on lungs and spleen lysates at day 14 post-bleomycin.
Figure 19B:
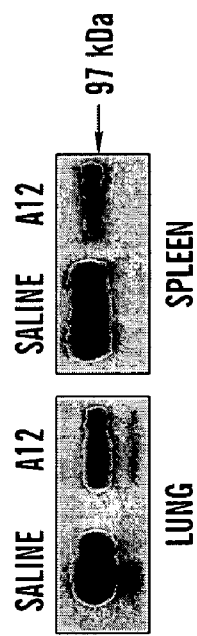

A12 antibody inhibits IGF-1 signaling by two mechanisms: 1) blockade of ligand binding to IGF-1R and 2) rapid induction of internalization and degradation of IGF-1R (Burtrum et al., *Cancer Res* 63:8912-8921 (2003)). Therefore, to verify efficacy of A12 treatment, IGF-1R expression was examined in the lungs of A12-treated mice and saline treated mice at day 7 following bleomycin. A marked decrease in IGF-1R expression was found in A12 treated mice, demonstrating the predicted effect of antibody administration in lung tissue (FIG. 19).

Treatment with A12 antibody improved survival and hastened resolution of fibrosis following bleomycin-induced lung injury. While initial fibrosis was similar in A12 and saline treated mice, there was a significant decrease in hydroxyproline content in A12-treated mice from d14 to day 28. Increased apoptosis in A12-treated mice was observed compared to vehicle-treated mice at day 14. The data also confirmed that A12 treatment induced apoptosis in mouse lung fibroblasts in vitro. An important question in pulmonary fibrosis is whether one can affect matrix remodeling once fibrosis has occurred. It has been proposed that apoptosis of fibrogenic cells (i.e., fibroblasts) is essential for the resolution of lung injury (Iredale et al., *J Clin Invest* 102:538-549 (1998); Phan, *Chest* 122:286 S-289S (2002); Uhal, *Chest* 122:293 S-298S (2002)). Because IGF pathway is a key determinant of cell survival, downregulation of this pathway may be necessary both for normal scarring to resolve and to prevent a prolonged fibrogenic response (i.e., fibrosis). Without wishing to be bound by theory, since the increased apoptosis preceded the improvement in fibrosis at d28, it is possible that this caused the improved fibrosis by eliminating the fibrogenic cells.

IGF regulates a number of cell functions that are relevant to development of fibrosis including proliferation, collagen synthesis and cell survival (Scarpa et al., *Peptides* 26:2201-2210 (2005); Goldstein et al, *Endocrinology* 124:964-970 (1989)). However, the contribution of IGF in animal models of fibrosis has been mixed. In a model of chronic renal failure due to subtotal nephrectomy, blockade of IGF resulted in less compensatory kidney growth, but no difference in renal function or fibrosis (Oldroyd et al., *American journal of physiology* 290:F695-702 (2006)). Transgenic mice expressing IGF-1A splice variant under the SP-C promoter in the lung developed adematous hyperplasia, but not fibrosis (Frankel et al., *Am J Physiol Lung Cell Mol Physiol* 288:L805-812 (2005)). As noted by those authors, lack of fibrosis in their transgenic model may be due to secretion of IGF-1A into the luminal compartment, rather than interstitial compartment; lack of overexpression of IGF-1B splice variant; or decreased bioavailability of IGF by binding to insulin growth factor-like binding proteins (IGFBPs).

IGF-1 was implicated as a fibroblast mitogen in BALF from patients with sarcoidosis (Allen et al., *Am J Respir Cell Mol Biol* 19:250-258 (1998)) and systemic sclerosis (Harrison et al., *Clin Sci (Lond)* 86:141-148 (1994)). IGF did not contribute to fibroblast proliferation in BALF from patients with asbestosis (Mutsaers et al., *The Journal of pathology* 185:199-203 (1998)). In the experiments described herein, IGF-1 mediated cell survival and migration, but not proliferation of normal lung fibroblasts through IGF-1R. The prior studies used either the fetal fibroblast cell line IMR-90 or human fetal embryonic fibroblasts (HFL-1) to examine the proliferative response (Allen et al., *Am J Respir Cell Mol Biol* 19:250-258 (1998); Harrison et al., *Clin Sci (Lond)* 86:141-148 (1994)). In contrast, the studies described herein used early passage primary adult lung fibroblasts, which may account for differences in results. In addition, the mitogenic response to IGF in the earlier studies was determined by immunodepletion of IGF from BALF (Allen et al., *Am J Respir Cell Mol Biol* 19:250-258 (1998); Harrison et al., *Clin Sci (Lond)* 86:141-148 (1994)). Without wishing to be bound by theory, it is thought that activation of fibroblasts by other growth factors or cytokines such as TGFβ1 in BALF may be necessary for the pro-proliferative effect of IGF (Scarpa et al., *Peptides* 26:2201-2210 (2005); Danielpour and Song, *Cytokine & growth factor reviews* 17:59-74 (2006)). TGFβ1, an important mediator of fibrosis, significantly upregulated IGF-1 expression in lung fibroblasts (not shown).

The experiments described herein (see Example 14) confirm that lung fibroblasts express the major components of IGF signaling pathways including IGF-1 Receptor, IRS-1 and IRS-2. Interestingly, only IRS-2 showed increased phosphorylation following IGF-1 stimulation. IRS-1 was present and phosphorylated at baseline and there was no change after IGF-1 stimulation. Furthermore, Akt but not Erk, was phosphorylated in response to IGF stimulation. The signaling response to IGF-1 varies depending on the cell examined (Petley et al., *Hormone and metabolic research Hormon-und Stoffwechselforschung* 31:70-76 (1999)). Both PI3-kinase pathway and MAP kinase pathway are involved in IGF-1R mediated signaling in carcinoma and other cell types (Le-Roith and Roberts, *Cancer Lett* 195:127-137 (2003)). In myeloma cells, both anti-apoptotic signal and pro-proliferative signal from IGF-1 was mediated by PI3-K (Qiang et al., *Blood* 99:4138-4146 (2002)). In myoblasts, IGF-1-induced differentiation was mediated by PI3-K, while proliferation was mediated by MAPK (Coolican et al, *J Biol Chem* 272: 6653-6662 (1997)). In hepatocytes, IGF-mediated cell survival was dependent on IRS-2 (Valverde et al., *Hepatology*

40:1285-1294 (2004)). In our experiments, IGF-1 stimulation selectively activated IRS-2 and PI3 kinase pathway, and not IRS-1 and MAP kinase pathway. Although IGF-1 increases proliferation in many cell types (Maeda et al., *Chest* 109:780-786 (1996); Hoang et al., *Cancer Res* 64:7479-7485 (2004); Coolican et al., *J Biol Chem* 272:6653-6662 (1997); Allen et al., *Am J Respir Cell Mol Biol* 19:250-258 (1998); Harrison et al., *Clin Sci* (*Lond*) 86:141-148 (1994); Qiang et al., *Blood* 99:4138-4146 (2002)), no effect of IGF-1 was seen on lung fibroblast proliferation. These results, however, are consistent with the selective activation of IRS-1 and IRS-2 leading to proliferation and migration respectively in pleural mesothelioma cells (Hoang et al., *Cancer Res* 64:7479-7485 (2004)).

One feature of pulmonary fibrosis is migration of fibroblasts into the intraalveolar space, where they secrete matrix proteins and contribute to the obliteration of normal architecture. It was found in the experiments described herein that IGF-1 induced the migration of fibroblasts, which was inhibited by addition of A12. IGF-1R activation can affect cell migration through several mechanisms including down-regulation of adhesive strength of integrins (Lynch et al., *Mol Biol Cell* 16:51-63 (2005)), redistribution of integrins to leading edge of migrating cells, and disruption of cadherin/catenin complexes (Andre et al., *Int J Cancer* 83:497-505 (1999)). While not wishing to be bound by theory, since the inventors previously detected elevated levels of IGF-1 in ARDS BALF, IGF-1 may provide chemotactic factor for migration of fibroblasts into intraalveolar spaces, which results in deposition of matrix proteins and eradication of airspaces.

While not wishing to be bound by theory, improved survival may involve suppression of the initial inflammatory response by A12 is possible. There was a trend towards decreased BALF cell counts and total protein in A12 treated mice, suggesting less inflammation, but this did not reach statistical significance. No differences were seen in cell differentials at any time points. It is possible that earlier timepoints may have revealed differences in either lung permeability or inflammation that was subsequently reflected in mortality. There was no difference in hydroxyproline content at d7 and d14, suggesting that differences in early fibrosis did not account for decreased mortality of A12 treated mice. Again not wishing to be bound by theory, A12 treatment may affect response to oxidative stress following bleomycin injury, since IGF-1R heterozygote mice are resistant to oxidative stress and have longer life spans (Holzenberger et al., *Nature* 421:182-187 (2003)).

In summary, the data provided herein show that A12 administration improved survival of bleomycin treated mice. In addition, although initial fibrosis was similar in the control and A12-treated mice, A12-treated mice had faster resolution of fibrosis. While not wishing to be bound by theory, it is thought that some of the effects of A12 are due to increased fibroblast apoptosis, which facilitates matrix remodeling and resolution of fibrosis. These data show that the IGF-1R is a target for treatment of lung injury and fibrosis.

The invention claimed is:

1. A method for the treatment of acute lung injury in an individual in need thereof, the method comprising administering an inhibitor of IGF-1R signaling activity to said individual, wherein said inhibitor comprises an antibody or antigen-binding fragment thereof that binds the IGF-1R.

2. The method of claim 1 wherein said antibody or antigen-binding fragment thereof binds to the external domain of IGF-1R and inhibits binding of IGF-I or IGF-II to IGF-1R.

3. The method of claim 1 wherein said antibody or antigen-binding fragment thereof neutralizes IGF-1R signaling activity.

4. The method of claim 1 wherein said antibody or antigen-binding fragment thereof down-modulates IGF-1R.

5. The method of claim 1 wherein said antibody or antigen-binding fragment thereof comprises an antigen-binding domain of the antibody IMC-A12.

6. The method of claim 1 wherein said antibody or antigen-binding fragment thereof binds an epitope that is bound by the antibody IMC-A12.

7. The method of claim 1 wherein said inhibitor of IGF-1R activity is administered systemically.

8. The method of claim 1 wherein said inhibitor of IGF-1R signaling activity is delivered to the lung as an aerosol.

* * * * *

```
SEQUENCE LISTING

<160> NUMBER OF SEQ ID NOS: 5

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gggacccucc uccggagcca g                                            21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcuccggag gagggucccc g                                            21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggucuucuca cacaucggcu u                                            21
```

-continued

```
<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gccgaugugu gagaagaccu u                                              21

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(21)
<223> OTHER INFORMATION: a, c, g, t, unknown or other

<400> SEQUENCE: 5
aannnnnnnn nnnnnnnnnn ntt                                            23
```